United States Patent [19]

Tomita et al.

[11] Patent Number: 4,716,162
[45] Date of Patent: Dec. 29, 1987

[54] FUSED 5 RING HETEROCYCLIC COMPOUNDS, THEIR PREPARATION, AND THEIR ANTI-ARRHYTHMIC AND DIURETIC USE

[75] Inventors: Kuniyuki Tomita; Yasuo Shimoji; Seiji Kumakura; Hiroyuki Koike; Nobuyoshi Iwata; Yasuhiro Morisawa, all of Hiromachi, Japan

[73] Assignee: Sankyo Company, Limited, Tokyo, Japan

[21] Appl. No.: 755,474

[22] Filed: Jul. 16, 1985

[30] Foreign Application Priority Data

Jul. 18, 1984 [JP] Japan ................... 59-148766

[51] Int. Cl.$^4$ ............ A61K 27/00; A61K 31/495; C07D 401/14; C07D 471/04
[52] U.S. Cl. ..................... 514/234; 514/183; 514/214; 514/253; 514/283; 540/461; 540/519; 544/125; 544/361; 546/42; 546/188; 546/200
[58] Field of Search ............ 546/42, 188, 200; 544/125, 361; 260/244.4, 243.3, 245.7, 330.3; 540/461, 519; 514/214, 183, 253, 234, 283

[56] References Cited

U.S. PATENT DOCUMENTS 3,985,751 10/1976 Bruderlein et al. ............... 546/42

OTHER PUBLICATIONS

Aapro et al., Chem. Abst. 99-133362k.
Asselin et al., J. Med. Chem. 19 (6); pp. 792–797, (1976).
Bailey et al., J. Chem. Soc. Perkin Trans. 1 (1), pp. 97–101, (1980).

Primary Examiner—Donald G. Daus
Assistant Examiner—Cecilia Shen
Attorney, Agent, or Firm—Frishauf, Holtz, Goodman & Woodward

[57] ABSTRACT

Fused ring compounds of formula (I):

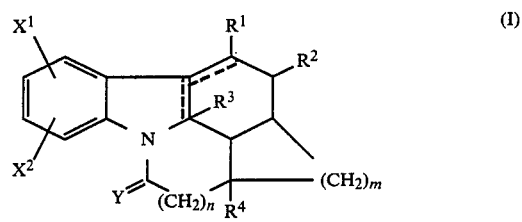

(where $R^1$–$R^4$, $X^1$ and $X^2$ represent hydrogen or various substituents, n and m are 1–3 and 2–7 respectively, the dotted lines are double or single bonds and Y is one oxygen or two hydrogens) have magnificent anti-arrhythmic activity, diuretic activity and the ability to improve brain function.

30 Claims, No Drawings

FUSED 5 RING HETEROCYCLIC COMPOUNDS, THEIR PREPARATION, AND THEIR ANTI-ARRHYTHMIC AND DIURETIC USE

BACKGROUND TO THE INVENTION

The present invention relates to a series of novel fused-ring heterocyclic compounds which we have found to have valuable pharmaceutical activities, in particular anti-arrhythmic and diuretic effects, as well as improving brain function. The invention also provides processes for preparing these new compounds, pharmaceutical compositions containing them and methods of treating mammals, including humans, suffering from arrhythmia, urine retention and brain function disorders.

A variety of compounds are known having these properties. However, the known compounds are structurally unrelated to the compounds of the present invention. So far as we are aware, the closest prior art constitutes the compounds disclosed in J. Chem. Soc., Perkin Trans., 1(1), 97–101 (1980) and J. Med. Chem., 19(6), 792–797 (1976), but the compounds of the J. Chem. Soc. reference contain only 4 fused rings, in contrast to the 5 fused rings of the compounds of the present invention, and are disclosed only in the context of their synthesis and structures, whilst no practical use is suggested. The compounds of the J. Med. Chem. reference contain only 3 fused rings and are discussed as potential antidepressants; one of the synthetic routes for these compounds proceeds via a 4-ring compound, but no therapeutic use is disclosed for this intermediate.

BRIEF SUMMARY OF INVENTION

The compounds of the invention are those compounds of formula (I):

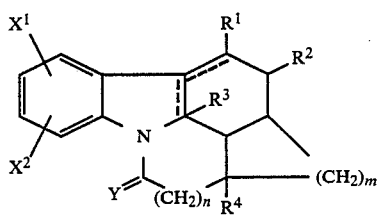

in which:

the dotted lines represent one single carbon-carbon bond and one double carbon-carbon bond or two single carbon-carbon bonds; m is an integer from 2 to 7;

n is an integer from 1 to 3;

Y represents 2 hydrogen atoms or an oxo group;

$R^1$ represents a hydrogen atom or a $C_1$–$C_6$ alkyl group;

$R^2$ represents a hydrogen atom, a carboxy group, a group of formula —NHCOOR$^b$ in which R$^b$ represents a $C_1$–$C_6$ alkyl group, a substituted $C_1$–$C_6$ alkyl group, an aralkyl group wherein the aryl part is $C_6$–$C_{10}$ carbocyclic aryl and the alkyl part is $C_1$–$C_6$ alkyl, a substituted aralkyl group wherein the aryl part is $C_6$–$C_{10}$ carbocyclic aryl and the alkyl part is $C_1$–$C_6$ alkyl, a $C_3$–$C_6$ alkenyl group, a $C_3$–$C_6$ haloalkenyl group, a $C_3$–$C_{10}$ cycloalkyl group or a substituted $C_3$–$C_{10}$ cycloalkyl group, a group of formula —NR$_2$, a quaternary ammonium group of formula —N$^+$(R')$_3$, a group of formula —CONR$_2$, a group of formula —NHNR$_2$, a group of formula —NHCONR$_2$, an aminoalkanoylamino group wherein the alkanoyl part is $C_2$–$C_7$ alkanoyl, a group of formula —CO.NH.NR$_2$ or a group of formula —CO.NH.N=CHR''';

the two atoms or groups represented by R are independently selected from the group consisting of hydrogen atoms, $C_1$–$C_6$ alkyl groups, substituted $C_1$–$C_6$ alkyl groups, aralkyl groups where the aryl part is $C_6$–$C_{10}$ carbocyclic aryl and the alkyl part is $C_1$–$C_6$ alkyl, substituted aralkyl groups where the aryl part is $C_6$–$C_{10}$ carbocyclic aryl and the alkyl part is $C_1$–$C_6$ alkyl, heterocyclic groups and substituted heterocyclic groups;

or the two symbols R, together with the nitrogen atom to which they are attached, represent a nitrogenous heterocyclic group;

the three groups represented by R' are independently selected from the group consisting of $C_1$–$C_6$ alkyl groups, substituted $C_1$–$C_6$ alkyl groups, aralkyl groups where the aryl part is $C_6$–$C_{10}$ carbocyclic aryl and the alkyl part is $C_1$–$C_6$ alkyl and substituted aralkyl groups where the aryl part is $C_6$–$C_{10}$ carbocyclic aryl and the alkyl part is $C_1$–$C_6$ alkyl;

R'' represents a $C_1$–$C_5$ alkyl group or a phenyl group;

$R^3$ represents a hydrogen atom, a $C_1$–$C_3$ alkyl group or a substituted $C_1$–$C_3$ alkyl group;

$R^4$ represents a hydrogen atom, a $C_1$–$C_6$ alkyl group, a $C_3$–$C_6$ alkenyl group, a $C_3$–$C_6$ alkynyl group, an aralkyl group wherein the aryl part is a $C_6$–$C_{10}$ carbocyclic aryl group and the alkyl part is $C_1$–$C_6$ alkyl, or the phenyl group;

$X^1$ and $X^2$ are independently selected from the group consisting of hydrogen atoms, $C_1$–$C_6$ alkyl groups, substituted $C_1$–$C_6$ alkyl groups, $C_1$–$C_6$ alkoxy groups, aralkyloxy groups wherein the aryl part is a $C_6$–$C_{10}$ carbocyclic aryl group and the alkyl part is a $C_1$–$C_6$ alkyl group, hydroxy groups, halogen atoms, trifluoromethyl groups, nitro groups, amino groups, aminoalkanoylamino groups wherein the alkanoyl part is $C_2$–$C_7$ alkanoyl, mono- and di- alkylaminoalkanoylamino groups wherein the alkanoyl part is $C_2$–$C_7$ alkanoyl and the or each alkyl part is $C_1$–$C_6$ alkyl and is substituted or unsubstituted, $C_2$–$C_7$ alkanoyloxy groups, carboxy groups, carbamoyl groups, mono- and di- alkylcarbamoyl groups where the or each alkyl part is $C_1$–$C_6$ alkyl and cyano groups;

the substituents on said alkyl, cycloalkyl, alkoxy, aralkyl and heterocyclic groups are from 1 to 3 substituents selected from the group consisting of halogen atoms, cyano groups, nitro groups, hydroxy groups, $C_1$–$C_4$ alkoxy groups, mercapto groups, $C_1$–$C_4$ alkylthio groups, $C_1$–$C_6$ alkanoyl groups, carboxy groups, alkoxycarbonyl groups where the alkoxy part is $C_1$–$C_4$ alkoxy, amino groups, $C_1$–$C_4$ alkylamino groups, dialkylamino groups where each alkyl part is $C_1$–$C_4$ alkyl, carbamoyl groups, alkylcarbamoyl groups where the alkyl part is $C_1$–$C_4$ alkyl, dialkylcarbamoyl groups where each alkyl part is $C_1$–$C_4$ alkyl, and, only as substituents on substituted alkyl and alkoxy groups, $C_3$–$C_{10}$ cycloalkyl groups, substituted $C_3$–$C_{10}$ cycloalkyl groups, heterocyclic groups and substituted heterocyclic groups, and, only as substituents on cycloalkyl groups and substituted aryl parts of aralkyl groups, $C_1$–$C_4$ alkyl groups and substituted $C_1$–$C_4$ alkyl groups, and, only as substituents on substituted heterocyclic groups, $C_1$–$C_4$ alkyl groups, substituted $C_1$–$C_4$ alkyl groups, $C_6$–$C_{10}$ carbocyclic aryl groups, substituted $C_6$–$C_{10}$ carbocyclic aryl groups, arylalkenoyl groups wherein the aryl part is $C_6$–$C_{10}$ carbocyclic aryl and the alkenoyl part is $C_3$–$C_6$ alkenoyl and substituted arylalkenoyl wherein the aryl part is substituted $C_6$–$C_6$ carbocyclic aryl and the alkenoyl part is $C_3$–$C_6$ alkenoyl;

said heterocyclic groups contain from 5 to 8 ring atoms of which from 1 to 4 are hetero-atoms selected from the group consisting of nitrogen, oxygen and sulfur atoms and the remainder is carbon atoms; said nitrogenous heterocyclic group is a heterocyclic group wherein at least one of said hetero-atoms is nitrogen, the group being bonded to the molecule of said compound via said nitrogen atom;

and pharmaceutically acceptable salts and esters thereof.

The invention also provides a pharmaceutical composition comprising an anti-arrhythmic compound in admixture with a pharmaceutically acceptable carrier or diluent, wherein the anti-arrhythmic compound is selected from the group consisting of compounds of formula (I) and salts and esters thereof.

DETAILED DESCRIPTION OF INVENTION

The compounds of the present invention contain 5 fused rings of which one, depending upon the value of n, may have 6, 7 or 8 ring atoms (n=1, 2 or 3, respectively) and another, depending upon the value of m, may have 5, 6, 7, 8, 9 or 10 ring atoms (m=2, 3, 4, 5, 6 or 7, respectively). In the present specification, the compounds of the invention are named and substituent positions are identified in accordance with the recommendations of the International Union of Pure and Applied Chemistry (IUPAC), Organic Chemistry Division.

For the avoidance of doubt, and as an illustration, compounds of formula (I) where n is 1 and m is 2 have the skeletal structure as shown in formula (II) on which is also shown the numbering applied to ring atoms:

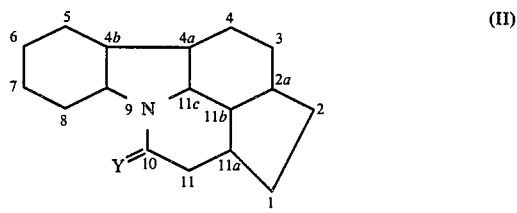
(II)

Compounds where n is 1 and m is 3 have the skeletal structure shown in formula (III), on which is also shown the numbering applied to ring atoms:

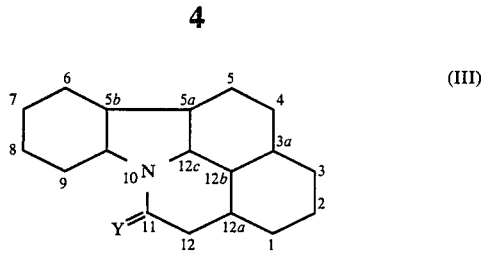
(III)

Compounds having other ring sizes are named and numbered following the same principles.

In the compounds of the invention, $R^1$ can represent a hydrogen atom or a $C_1$–$C_6$ alkyl group, for example a methyl, ethyl, propyl, isopropyl, butyl, isobutyl, sec-butyl, t-butyl, pentyl, isopentyl, neopentyl, t-pentyl, hexyl or isohexyl group, more preferably a $C_1$–$C_3$ alkyl group and most preferably a methyl, ethyl or propyl group. However, the most preferred compounds of the invention are those in which $R^1$ represents a hydrogen atom.

The compounds of the invention may contain one or more carboxy groups depending upon the meanings assigned to $R^2$, $X^1$ and $X^2$ and hence can form salts and esters. There is no particular limitation as to the nature of the salt-forming cation or ester-forming alcohol used to form such salts and esters in the present invention and any such cation or alcohol known for use in this type of compound may equally be employed in the present invention, without restriction. However, as is well-known in the art, where the compounds of the invention are to be employed for therapeutic use, the salt-forming cation or ester-forming alcohol employed should not, or should not to an unacceptable extent, reduce the activity or increase the toxicity of the compounds, as compared with the free acids. Where the compounds of the invention are not intended for therapeutic use, for example where they are intended for use as intermediates in the preparation of other compounds, even this restriction does not apply.

However, a preferred class of compounds of the present invention are those compounds of formula (IV):

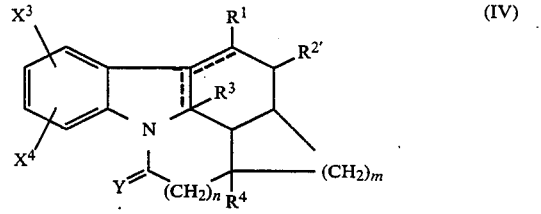
(IV)

wherein $R^1$, $R^3$, $R^4$, Y, n, m and the dotted lines are as defined above;

$R^{2'}$ represents any one of the groups or atoms defined for $R^2$ or a group of formula $COOR^a$ wherein $R^a$ represents a $C_1$–$C_6$ alkyl group, a substituted $C_1$–$C_6$ alkyl group, an aralkyl group wherein the aryl part is $C_6$–$C_{10}$ carbocyclic aryl and is substituted or unsubstituted and the alkyl part is $C_1$–$C_6$ alkyl, a $C_3$–$C_6$ alkenyl group, a $C_3$–$C_6$ haloalkenyl group, a $C_3$–$C_{10}$ cycloalkyl group (which may be monocyclic or polycyclic) or a $C_3$–$C_{10}$ cycloalkyl group having from 1 to 5 $C_1$–$C_4$ alkyl substituents; and $X^3$ and $X^4$ are independently selected from the group consisting of the groups and atoms defined for $X^1$ and $X^2$ and groups of formula $COOR^a$ in which $R^a$ is as defined above, but is preferably a $C_1$–$C_6$ alkyl group or a substituted $C_1$–$C_6$ alkyl group.

Substituents for said substituted alkyl and said substituted aryl groups are as defined above.

In the case of esters of compounds of formula (I), $R^2$ being a carboxy group [i.e. compounds of formula (IV) in which $R^{2'}$ represents a group of formula $COOR^a$], where $R^a$ represents an alkyl group, the alkyl group may have from 1 to 6, preferably from 1 to 4 carbon atoms and may be a straight or branched chain group; examples of such alkyl groups which may be represented by $R^a$ include the methyl, ethyl, propyl, isopropyl, butyl, isobutyl, sec-butyl, t-butyl, pentyl, isopentyl, neopentyl, t-pentyl, hexyl and isohexyl groups. Such alkyl groups may be unsubstituted or may have from 1 to 3 substituents selected from those defined above, preferably having 1 substituent only. Accordingly, preferred alkoxycarbonyl or substituted alkoxycarbonyl groups which may be represented by $COOR^a$ include: the unsubstituted alkoxycarbonyl groups, such as the methoxycarbonyl, ethoxycarbonyl, propoxycarbonyl, isopropoxycarbonyl, butoxycarbonyl or isobutoxycarbonyl groups; haloalkoxycarbonyl groups such as the 2-bromoethoxycarbonyl or 3-chloropropoxycarbonyl groups; and aminoalkoxycarbonyl groups such as 2-aminoethoxycarbonyl, 2-dimethylaminoethoxycarbonyl, 3-aminopropoxycarbonyl, 3-dimethylaminopropoxycarbonyl, 2-(1-pyrrolidinyl)ethoxycarbonyl, 2-piperidinoethoxycarbonyl, 2-morpholinoethoxycarbonyl, 2-(4-methyl-1-piperazinyl)ethoxycarbonyl, 2-[4-(p-methylphenyl)-1-piperazinyl)ethoxycarbonyl, 2-[4-(p-methylphenyl)-1-piperazinyl]ethoxycarbonyl and 2-[4-(3,4,5-trimethoxycinnamoyl)-1-piperazinyl]ethoxycarbonyl groups.

Where the compound of the present invention is an ester of a compound of formula (I), $R^2$ in the compound of formula (I) being a carboxy group [i.e. the compound of formula (IV) where $R^{2'}$ represents a group of formula $COOR^a$] and the ester is an aralkyl ester, the aralkyl group is a group in which the aryl part is a $C_6$–$C_{10}$ carbocyclic aryl group (which may be unsubstituted or substituted by any of the substituents defined above) and the alkyl part is a $C_1$–$C_6$ alkyl group. Examples of such alkyl groups are the groups given in relation to the alkyl groups which may be represented by $R^1$ and preferred such alkyl groups are the methyl, ethyl and propyl groups. Preferred such aryl groups are the phenyl group (which may be substituted as defined above in relation to aryl groups) and the 1- and 2- naphthyl groups. Accordingly, preferred examples of such groups which may be represented by $COOR^a$ are the aralkyloxycarbonyl groups such as the benzyloxycarbonyl, p-nitrobenzyloxycarbonyl and phenethyloxycarbonyl groups.

Where the ester is an alkenyl ester, the alkenyl group has from 3 to 6 carbon atoms and may be a straight or branched chain group, examples of such groups include the 1-propenyl, allyl, isopropenyl, 1-butenyl, 2-butenyl, 2-methyl-2-propenyl, 1-pentenyl, 2-pentenyl, 3-pentenyl, 1-hexenyl, 2-hexenyl and 3-hexenyl groups, of which the allyl and 2-methyl-2-propenyl (=methallyl) groups are preferred. The alkenyl group may be halogen-substituted, i.e. a haloalkenyl group, for example a chloroalkenyl, bromoalkenyl, fluoroalkenyl or iodoalkenyl group, particularly a 3-chloroallyl, 3-bromoallyl or 3-iodoallyl group. Examples of alkenyloxycarbonyl and haloalkenyloxycarbonyl groups which may be represented by $COOR^a$ include the allyloxycarbonyl, methallyloxycarbonyl, chloroallyloxycarbonyl and bromoallyloxycarbonyl groups.

Where $R^a$ represents a $C_3$–$C_{10}$ cycloalkyl group or substituted cycloalkyl group, the cycloalkyl group may be a monocyclic or polycyclic (including bridged cyclic) cycloalkyl system having from 3 to 10 ring carbon atoms; it may be substituted or unsubstituted and, if substituted, has from 1 to 5, preferably from 1 to 3, $C_1$–$C_4$ alkyl substituents. Examples of the alkyl substituents include those $C_1$–$C_4$ alkyl groups amongst the alkyl groups which may be represented by $R^1$ and preferred alkyl substituents are the methyl, ethyl and isopropyl groups, more preferably the methyl group. In the case of the monocyclic cycloalkyl groups, the group preferably has from 3 to 8 ring carbon atoms and examples of these groups include the cyclopropyl, cyclobutyl, cyclopentyl, cyclohexyl, cycloheptyl and cyclooctyl groups, of which the cyclopentyl and cyclohexyl groups (which may have one or more of the aforementioned alkyl, preferably methyl, substituents) are preferred. Other examples of cycloalkyl groups include groups derived from the cyclic terpenes, particularly groups derived from bornane, isobornane and norbornane, of which the 2-bornyl group is preferred.

In the compounds of formula (I) $R^2$ can also represent a carbonylamino group, examples of which include the alkoxycarbonylamino, haloalkoxycarbonylamino, aralkyloxycarbonylamino, aminoalkoxycarbonylamino, alkenyloxycarbonylamino, haloalkenyloxycarbonylamino, cycloalkyloxycarbonylamino and alkyl-substituted cycloalkyloxycarbonylamino groups. Such groups may be represented by the formula $NHCOOR^a$, in which $R^a$ is as defined above and may be any one of the groups exemplified above for $R^a$. Examples of such carbonylamino groups include the lower alkoxycarbonylamino groups and aralkyloxycarbonylamino groups such as the methoxycarbonylamino, ethoxycarbonylamino, t-butoxycarbonylamino, benzyloxycarbonylamino and p-nitrobenzyloxycarbonylamino groups; cycloalkoxycarbonylamino groups such as the cyclopentyloxycarbonylamino, cyclohexyloxycarbonylamino, bornan-2-yloxycarbonylamino and isobornan-2-yloxycarbonylamino groups.

$R^2$ can also represent an amino group of formula —$NR_2$, in which R is as defined above. Where the two symbols R both represent hydrogen atoms, the group is an unsubstituted amino group. Where one or both of the symbols R represents an alkyl, substituted alkyl, aralkyl, substituted aralkyl, heterocyclic or substituted heterocyclic group, the group —$NR_2$ is a substituted amino group. Where the two symbols R together with the nitrogen atom to which they are attached represent a nitrogenous heterocyclic group, this is a group containing from 5 to 8 ring atoms, of which from 1 to 4 are hetero-atoms selected from the group consisting of nitrogen, oxygen and sulfur atoms, at least one of said hetero-atoms being nitrogen.

Examples of such groups which may be represented by $-NR_2$ include: the amino group; amino groups substituted by a lower alkyl or aralkyl group with or without substituent(s), such as the methylamino, dimethylamino, ethylamino, 2-hydroxyethylamino, diethylamino, propylamino, dipropylamino, isopropylamino, diisopropylamino, N,N-methylethylamino, N,N-methylbenzylamino, N-(2-hydroxyethyl)-N-methylamino, N-(3-hydroxypropyl)-N-methylamino, N-(2-methoxyethyl)-N-methylamino, N-(2-carboxyethyl)-N-methylamino and N-(3-carboxypropyl)-N-methylamino groups; cyclic amino groups such as the 1-pyrrolidinyl, morpholino, piperidino, 1-piperazinyl, 4-methyl-1-piperazinyl and 4-phenyl-1-piperazinyl groups.

$R^2$ can also represent a quaternary ammonium group of formula $N^+(R')_3$, wherein the three groups represented by $R'$ are the same or different and each represents a $C_1-C_6$ alkyl group, which may be unsubstituted or may have from 1 to 3 of the substituents defined above, or an aralkyl group where the aryl part is $C_6-C_{10}$ carbocyclic aryl and the alkyl part is $C_1-C_6$ alkyl and which may be unsubstituted or may have from 1 to 3 of the substituents defined above.

Where $R^2$ represents such a quaternary ammonium group, the compound is, of course, completed by the presence of an anion, the nature of which is not critical, provided that, where the compound of the invention is to be employed for therapeutic use, it does not, or does not to an unacceptable extent, reduce the activity or increase the toxicity of the compound as compared with the corresponding compound without the anion. The list of potential anions is considerable, as is well recognized in the art, and a non-limiting sample of suitable anions include the halide (e.g. chloride, iodide, fluoride and bromide), hydroxide, sulfate, hydrogen sulfate, carbonate and hydrogen carbonate anions.

Specific examples of such quaternary ammonium groups include the N,N,N-trimethylammonium bromide, N,N,N-trimethylammonium iodine, N,N,N-triethylammonium chloride, N,N-dimethyl-N-ethylammonium hydroxide, N,N-dimethyl-N-benzylammonium bromide, N-(2-hydroxyethyl)-N,N-dimethylammonium iodide, N-(3-hydroxypropyl)-N,N-dimethylammonium iodide and N-(2-carboxyethyl)-N,N-dimethylammonium iodide groups.

Where $R^2$ represents a group of formula $-CONR_2$, this is a carbamoyl group, a substituted carbamoyl group or a group derived from a heterocyclic-carboxylic acid. The nature of the group or groups which may be represented by the two symbols R has been discussed above and specific examples of such groups of formula $-CONR_2$ include: the carbamoyl group; mono- and di-substituted carbamoyl groups (including, in particular, carbamoyl groups having a single substituent which is an alkyl group preferably $C_2-C_4$, having itself a single substituent of formula $-NR_2$), such as the N-methylcarbamoyl, N,N-dimethylcarbamoyl, N,N-diisopropylcarbamoyl groups; N-(2-chloroethyl)carbamoyl, N-(2-bromoethyl)carbamoyl, N-(3-chloropropyl)carbamoyl, N-(2-hydroxyethyl)carbamoyl, N-(2-ethoxyethyl)carbamoyl, N-(3-propoxypropyl)carbamoyl, N-(2-N,N-dimethylaminoethyl)carbamoyl, N-(2-N,N-diethylaminoethyl)carbamoyl, N-(ethoxycarbonymethyl)carbamoyl, N-(2-cyclohexylethyl)carbamoyl, N-[2-(1-pyrrolidinyl)ethyl]carbamoyl, N-(2-piperidinoethyl)carbamoyl, N-(2-morpholinoethyl)carbamoyl, N-(3-morpholinopropyl)carbamoyl, N-(4-morpholinobutyl)carbamoyl, N-[2-(4-methyl-1-piperazinyl)ethyl]carbamoyl, N-[2-(4-phenyl-1-piperazinyl)ethyl]carbamoyl, N-[2-(4-ethoxycarbonyl-1-piperazinyl)ethyl]carbamoyl, N-benzylcarbamoyl, N-4-methylbenzylcarbamoyl, N-2-chlorobenzylcarbamoyl, N-4-chlorobenzylcarbamoyl, N-2-methoxybenzylcarbamoyl, N-4-methoxybenzylcarbamoyl, N-3,4-dimethoxybenzylcarbamoyl, N-phenethylcarbamoyl, N-4-methylphenethylcarbamoyl, N-4-chlorophenethylcarbamoyl, N-4-methoxyphenethylcarbamoyl, N-3,4-dimethoxyphenethylcarbamoyl, N-3,4,5-trimethoxyphenethylcarbamoyl, N-3-phenylpropylcarbamoyl, N-4-phenylbutylcarbamoyl, N-furfurylcarbamoyl, N-(2-pyridylmethyl)carbamoyl, N-(4-pyridylmethyl)carbamoyl, N-(2-pyrid-2-ylethyl)carbamoyl, N-cyclopentylcarbamoyl, N-cyclohexylcarbamoyl, N-phenylcarbamoyl, N-4-tolylcarbamoyl, N-4-chlorophenylcarbamoyl, N-4-methoxyphenylcarbamoyl, N-2-pyridylcarbamoyl, N-2-furylcarbamoyl, N-morpholinocarbamoyl, N-piperidinocarbamoyl and N-piperazinylcarbamoyl groups; and heterocyclic-carbonyl groups, such as the 1-pyrrolidinylcarbonyl, piperidinocarbonyl, 4-methyl-1-piperazinylcarbonyl and 4-phenyl-1-piperazinylcarbonyl groups.

Where $R^2$ represents a hydrazino or substituted hydrazino group of formula $-NHNR_2$, the two symbols R may represent the same or different groups and atoms, as defined above. Specific examples of such hydrazino and substituted hydrazino groups include: the hydrazino group; and substituted hydrazino groups such as the methylhydrazino, hydroxyethylhydrazino, phenylhydrazino, N-(2-morpholinoethyl)hydrazino, N-[2-(1-pyrrolidinyl)ethyl]hydrazino, N-(2-piperidinoethyl)hydrazino, N-[2-(4-methyl-1-piperazinyl)ethyl]hydrazino and N-(2-pyridiyl)hydrazino groups.

Where $R^2$ represents a ureido or substituted ureido group of formula $-NHCONR_2$, the two symbols R may be the same or different and are as defined above. Examples of such ureido and substituted ureido groups include: the ureido group; and mono- or di-substituted ureido groups, such as the N-ethylaminocarbonylamino, N,N-dimethylaminocarbonylamino, 4-phenyl-1-piperazinylcarbonylamino, and 4-(m-tolyl)-1-piperazinylcarbonylamino groups.

Where $R^2$ represents a carbazoyl or substituted carbazoyl group of formula $-CONHNR_2$, the two symbols R may be the same or different and are as defined above. Specific examples of such carbazoyl and substituted carbazoyl groups include: the carbazoyl group;

mono- and di-substituted carbazoyl groups (including, in particular, carbazoyl groups having a single substituent which is an alkyl group, preferably $C_2$–$C_4$, having itself a single substituent of formula —$NR_2$), such as the N-methylcarbazoyl, N,N-dimethylcarbazoyl, N,N-diisopropylcarbazoyl groups; N-(2-chloroethyl)carbazoyl, N-(2-bromoethyl)carbazoyl, N-(3-chloropropyl)-carbazoyl, N-(2-hydroxyethyl)carbazoyl, N-(2-ethoxyethyl)carbazoyl, N-(3-propoxypropyl)carbazoyl, N-(2-N,N-dimethylaminoethyl)carbazoyl, N-(2-N,N-diethylaminoethyl)carbazoyl, N-(ethoxycarbonylmethyl)-carbazoyl, N-(2-cyclohexylethyl)carbazoyl, N-[2-(1-pyrrolidinyl)ethyl]carbazoyl, N-(2-piperidinoethyl)carbazoyl, N-(2-morpholinoethyl)carbazoyl, N-(3-morpholinopropyl)carbazoyl, N-(4-morpholinobutyl)carbazoyl, N-[2-(4-methyl-1-piperazinyl)ethyl]carbazoyl, N-[2-(4-phenyl-1-piperazinyl)ethyl]carbazoyl, N-[2-(4-ethoxycarbonyl-1-piperazinyl)ethyl]carbazoyl, N-benzylcarbazoyl, N-4-methylbenzylcarbazoyl, N-2-chlorobenzylcarbazoyl, N-4-chlorobenzylcarbazoyl, N-2-methoxybenzylcarbazoyl, N-4-methoxybenzylcarbazoyl, N-3,4-dimethoxybenzylcarbazoyl, N-phenethylcarbazoyl, N-4-methylphenethylcarbazoyl, N-4-chlorophenethylcarbazoyl, N-4-methoxyphenethylcarbazoyl, N-3,4-dimethoxyphenethylcarbazoyl, N-3,4,5-trimethoxyphenethylcarbazoyl, N-3-phenylpropylcarbazoyl, N-4-phenylbutylcarbazoyl, N-furfurylcarbazoyl, N-(2-pyridylmethyl)carbazoyl, N-(4-pyridylmethyl)carbazoyl, N-(2-pyrid-2-ylethyl)carbazoyl, N-cyclopentylcarbazoyl, N-cyclohexylcarbazoyl, N-phenylcarbazoyl, N-4-tolylcarbazoyl, N-4-chlorophenylcarbazoyl, N-4-methoxyphenylcarbazoyl, N-2-pyridylcarbazoyl, N-2-furylcarbazoyl, N-morpholinocarbazoyl, N-piperidinocarbazoyl and N-piperazinylcarbazoyl groups; and heterocyclic-carbamoyl groups, such as the 1-pyrrolidinylcarbamoyl, piperidinocarbamoyl, 4-methyl-1-piperazinylcarbamoyl and 4-phenyl-1-piperazinylcarbamoyl groups.

Where $R^2$ represents a group of formula —CO.NH.N=CHR", R" may represent a $C_1$–$C_5$ alkyl group or a phenyl group, which may be unsubstituted or may have one or more of the substituents heretofore defined in relation to aryl groups. Where R" represents a $C_1$–$C_5$ alkyl group, this may be a straight or branched chain group and examples include the methyl, ethyl, propyl, isopropyl, butyl, isobutyl, sec-butyl, t-butyl, pentyl, isopentyl, neopentyl and t-pentyl groups. Where R" represents a phenyl group, this is preferably the unsubstituted phenyl group. Preferred groups represented by $R^2$ are those in which R' represents a propyl group or a phenyl group.

In the compounds of the invention, $R^3$ may represent a hydrogen atom or a $C_1$–$C_3$ alkyl group.

Where $R^3$ represents an alkyl group, this may be a straight or branched chain group having from 1 to 3, carbon atoms and examples include the methyl, ethyl, propyl and isopropyl groups.

$R^4$ can represent a hydrogen atom, a $C_1$–$C_6$, preferably $C_1$–$C_5$, alkyl group, a $C_3$–$C_6$, preferably $C_3$–$C_5$, alkenyl group, a $C_3$–$C_6$, preferably $C_3$ or $C_4$, alkynyl group, an aralkyl group (which can be substituted or unsubstituted) or the phenyl group.

Where $R^4$ represents a $C_1$–$C_6$ alkyl group, it may be any one of the alkyl groups heretofore given in relation to the alkyl groups which may be represented by $R^1$, but is preferably a methyl, ethyl, propyl, isopropyl, butyl, isobutyl, sec-butyl, t-butyl, pentyl or isopentyl group.

Where $R^4$ represents an alkenyl group, this has from 3 to 6 carbon atoms and may be a straight or branched chain group. Examples of such alkenyl groups include the allyl, 1-propenyl, 2-butenyl and 3-methyl-2-butenyl groups. Where $R^4$ represents an alkynyl group, this likewise has from 3 to 6 carbon atoms and may be a straight or branched chain group. Preferred alkynyl groups include the 1-propynyl, 2-propynyl and 2-butynyl groups.

Where $R^4$ represents an aralkyl group, the aryl part is a $C_6$–$C_{10}$ carbocyclic aryl group, for example a phenyl, 1-naphthyl or 2-naphthyl group and the alkyl part is a $C_1$–$C_6$ alkyl group (e.g. any one of these heretofore described in relation to the alkyl groups which may be represented by $R^1$) but preferably a methyl, ethyl or propyl group. Preferred examples of such aralkyl groups include the benzyl, p-methylbenzyl, p-methoxybenzyl, 3,4-dimethoxybenzyl, p-chlorobenzyl, 2-phenethyl, 2-(p-methoxyphenyl)ethyl, 2-(3,4-dimethoxyphenyl)ethyl, 2-(3,4,5-trimethoxyphenyl)ethyl, α-methylbenzyl and 3-phenylpropyl groups.

$X^1$ and $X^2$ are the same or different and each represents a hydrogen atom, a $C_1$–$C_6$ alkyl group, a substituted $C_1$–$C_6$ alkyl group, a $C_1$–$C_6$ alkoxy group, an aralkyloxy group wherein the aryl part is a $C_6$–$C_{10}$ carbocyclic aryl group and the alkyl part is a $C_1$–$C_6$ alkyl group, a hydroxy group, a halogen atom, a trifluoromethyl group, a nitro group, an amino group, an aminoalkanoylamino group wherein the alkanoyl part is $C_2$–$C_7$ alkanoyl, a mono- or di-alkylaminoalkanoylamino group wherein the alkanoyl part is $C_2$–$C_7$ alkanoyl and the or each alkyl part is $C_1$–$C_6$ alkyl and is substituted or unsubstituted, a $C_2$–$C_7$ alkanoyloxy group, a carboxy group, a carbamoyl group, a mono- or di-alkylcarbamoyl group where the or each alkyl part is $C_1$–$C_6$ alkyl or a cyano group.

Where one or both of $X^1$ and $X^2$ represents a carboxy group, the group may be esterified, to form a group of formula $COOR^a$ and examples of such groups are those given in relation to the corresponding groups which may be represented by $R^{2'}$.

Similarly, many of the other groups which may be represented by $X^1$ and $X^2$ (or $X^3$ and $X^4$) are similar to those groups which may be represented by $R^2$ (or $R^{2'}$) and the description of such groups represented by $R^2$ (or $R^{2'}$) applies mutatis mutandis to the groups represented by $X^1$ and $X^2$ (or $X^3$ and $X^4$). Preferred examples of groups which may be represented by $X^1$, $X^2$, $X^3$ and $X^4$ include: the hydrogen atom; the carboxy group; straight and branched chain $C_2$–$C_7$ alkoxycarbonyl groups, such as the methoxycarbonyl, ethoxycarbonyl, propoxycarbonyl, isopropoxycarbonyl and butoxycarbonyl groups; aralkyloxycarbonyl groups, such as the benzyloxycarbonyl, p-methoxybenzyloxycarbonyl, and p-chlorobenzyloxycarbonyl groups; the cyano group; acyloxy groups, such as the acetoxy, propionyloxy, butyryloxy, and benzoyloxy groups; lower alkanoylamino groups, such as the acetylamino, propionylamino, butyrylamino, and isobutyrylamino groups; the carbamoyl group; substituted carbamoyl groups, such as the N-methylcarbamoyl, N-ethylcarbamoyl, N-propylcarbamoyl, N,N-dimethylcarbamoyl, N,N-diethylcarbamoyl, N,N-dipropylcarbamoyl, N,N-diisopropylcarbamoyl, N,N-dibutylcarbamoyl, N-benzylcarbamoyl, N-ethyl-N-benzylcarbamoyl, and N-(2-chloroethyl)carbamoyl groups; straight or branched chain $C_1$–$C_6$ alkyl groups, such as the methyl, ethyl, propyl, isopropyl, butyl, isobutyl and t-butyl groups; straight or branched chain $C_1$–$C_6$ alkoxy groups, such as the methoxy, ethoxy, propoxy, isopropoxy, butoxy and isobutoxy groups; substituted and unsubstituted aralkyloxy groups, such as the benzyloxy, p-methoxybenzyloxy, p-chlorobenzyloxy, phenethyloxy, and 3-phenylpropoxy groups; the hydroxy group; halogen atoms such as the fluorine, chlorine, bromine and iodine atoms; the trifluoromethyl group; the nitro group; or the amino group.

Y represents two hydrogen atoms or an oxo group, preferably an oxo group.

n represents an integer, 1, 2 or 3, preferably 1 or 2 and more preferably 1.

m represents an integer, 2, 3, 4, 5, 6 or 7, more preferably 2, 3 or 4, still more preferably 2 or 3 and most preferably 3.

The dotted lines may represent one single bond and one double bond or two single bonds. The preferred compounds of the invention are those compounds in which there is a double bond represented by the dotted line within the indolyl part of the molecule; in this case, there is no group represented by $R^3$.

Preferred compounds of the invention are those compounds of formula (IV) in which:

m is 2 or 3;
n is 1;
Y represents an oxo group;
$R^1$ represents a hydrogen atom;
$R^{2'}$ represents a group of formula COOR$^a$, in which R$^a$ represents an aminoalkyl group, or $R^{2'}$ represents a group of formula —NR$_2$, in which the two groups represented by R are independently selected from the group consisting of hydrogen atoms and $C_1$–$C_4$ alkyl groups, an aminoalkanoylamino group, in which the alkanoyl part is a $C_2$–$C_7$ alkanoyl group, a group of formula —CO.NH.NR$_2$, in which the two groups represented by R are independently selected from the group consisting of $C_1$–$C_6$ alkyl groups, or the two groups represented by R together with the nitrogen atom to which they are attached represent a nitrogenous heterocyclic group, or a group of formula —CO.NHNHR, in which R represents a $C_1$–$C_6$ aminoalkyl group, a phenyl group, an aralkyl group in which the aryl part is $C_6$–$C_{10}$ carbocyclic aryl and the alkyl part is $C_1$–$C_4$ alkyl, a heterocyclic group, a hydrogen atom, a $C_1$–$C_4$ alkyl group or a $C_1$–$C_4$ hydroxyalkyl group;

$R^3$ represents a hydrogen atom;
$R^4$ represents a hydrogen atom, a $C_1$–$C_4$ alkyl group or an aralkyl group in which the aryl part is $C_6$–$C_{10}$ carbocyclic aryl and the alkyl part is $C_1$–$C_4$ alkyl; and $X^3$ and $X^4$ are independently selected from the group consisting of hydrogen atoms and hydroxy groups.

Another preferred class of compounds of the present invention are those compounds of formula (V):

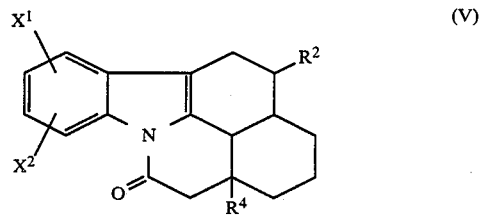

(in which:

$R^2$ represents a 2-(1-piperazinyl)ethoxycarbonyl group, a 2-(1-piperazinyl)ethoxycarbonyl group having an alkyl, phenyl, substituted phenyl or alkoxycarbonyl substituent at the 4-position of the piperazinyl group, an amino group, a dimethylamino group, an aminoacetamido group, an aminoacetamido group having one or two $C_1$–$C_4$ alkyl substituents on the amino group, a carbamoyl group having a single dimethylamino, morpholino, piperidino, 1-pyrrolidinyl or 4-methyl-1-piperazinyl substituent, a carbazoyl group or a carbazoyl group having on the 3-nitrogen atom a substituent selected from the group consisting of methyl, 2-hydroxyethyl, phenyl, benzyl, pyridyl, 2-(1-pyrrolidinyl)ethyl, 2-piperidinoethyl, 2-morpholinoethyl and 2-(4-methyl-1-piperazinyl)ethyl substituents;

$R^4$ represents a hydrogen atom or a methyl, ethyl, propyl, isopropyl, butyl, 4-methoxyphenethyl, 3,4-dimethoxyphenethyl or 3,4,5-trimethoxyphenethyl group; and $X^1$ and $X^2$ are independently selected from the group consisting of hydrogen atoms and hydroxy groups at the 6-, 7- and 8-positions.

More preferably, in the compounds of formula (V) above, either both $X^1$ and $X^2$ represent hydrogen atoms, or $X^2$ represents a hydrogen atom and $X^1$ represents a 6-hydroxy or 7-hydroxy group or $X^1$ represents a 7-hydroxy group and $X^2$ represents an 8-hydroxy group.

Where the compounds of the invention contain one or more carboxy groups, they can form salts with suitable cations. The nature of the cation employed is not critical, provided that, where the compound is to be employed as a pharmaceutical, the cation does not, or does not to an unacceptable extent, reduce the activity or increase the toxicity of the compound, as compared with the free acid. Examples of salts which may be employed in the present invention include: metal salts, particularly alkali metal or alkaline earth metal salts or salts with trivalent metals, such as the lithium, sodium, potassium, calcium, magnesium, aluminum or iron salts; salts with basic amino acids, such as lysine or arginine; ammonium salts; and salts with organic amines, such as cyclohexylamine, diisopropylamine or triethylamine. Of these, the alkali metal and alkaline earth metal salts, such as sodium, potassium and calcium salts, are preferred.

The compounds also contain a basic nitrogen atom and hence can form acid addition salts. The nature of the acid employed to form such salts is not critical, provided that, where the compound of the invention is intended for therapeutic use, the salts are pharmaceutically acceptable, in the sense that the salts have neither reduced activity, or unacceptably reduced activity, nor increased toxicity, or unacceptably increased toxicity, as compared with the free compound of formula (I). Where the compounds are not intended for pharmaceutical use, this restriction does not apply. Examples of suitable acids which can be employed to form pharmaceutically acceptable salts include: mineral acids, such as hydrochloric acid, hydrobromic acid, hydroiodic acid, sulfuric acid and phosphoric acid; organic carboxylic acids, such as formic acid, acetic acid, oxalic acid, malonic acid, maleic acid, fumaric acid, succinic acid, citric acid, tartaric acid, aspartic acid and benzoic acid; and organic sulfonic acids, such as methanesulfonic acid, ethanesulfonic acid, benzenesulfonic acid and p-toluenesulfonic acid.

The compounds of the invention can, depending upon the nature of the substituents, contain several asymmetric carbon atoms and, accordingly, various optical isomers and diastereoisomers may be possible. The present invention envisages both the individual isolated isomers and mixtures (which may be racemates) of these isomers.

Specific examples of compounds of the present invention are given in the following Tables. In these Tables, the following abbreviations are used:

All=allyl;
Brn=2-bornyl;
Bu=butyl;
Bz=benzyl;
Cin=cinnamoyl;
Et=ethyl;
iPr=isopropyl;
Me=methyl;
Mor=morpholino;
mTo=m-tolyl;
Ph=phenyl;
Pid=piperidino;
Pip=1-piperazinyl;
Pr=propyl;
Prl=1-pyrrolidinyl.

Where one of the groups abbreviated as defined above is substituted, this is indicated by preceding the abbreviation for the substituted group by the appropriate designation for the substituent and preceding that by a number identifying the position of attachment of the substituent to the substituted group. In the case of substituted ethyl groups, where no number is given to indicate the position of attachment of the substituent on the ethyl group, then the group is a 2-substituted ethyl group.

As noted above, various of the compounds of the invention can exist in the form of optical isomers and diastereoisomers. In some cases, the configuration of one or more of the asymmetric carbon atoms is specified by "α" or "β". In the case of asymmetric carbon atoms where no such configuration is identified, the atom can be in the α or β configuration or the compound may be a mixture of isomers in the α and β configurations.

It should be noted that, where a configuration is specified in the following Tables for certain of the Compounds, these configurations are indicated solely for the convenience of identifying compounds hereafter by the compound numbers assigned to them in these Tables and that the invention embraces compounds of any configuration (regardless of the configuration specified in these Tables) as well as mixtures of isomers of these compounds.

Compounds of formula (I-1):

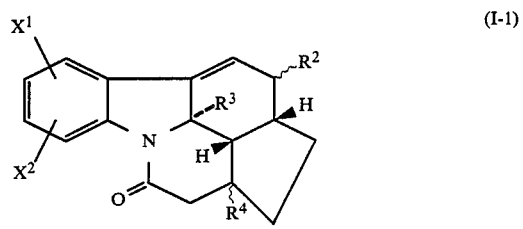

(I-1)

are as defined in Table 1.

TABLE 1

| Cpd No | X¹ | X² | R² | R³ | R⁴ |
|---|---|---|---|---|---|
| 1 | H | H | COOMe(β) | H | H(β) |
| 2 | 8-Me | H | COOMe(β) | H | H(β) |
| 3 | 6-OMe | H | COOMe(β) | H | H(β) |
| 4 | 6-OMe | 7-OMe | COOMe(β) | H | H(β) |
| 5 | 6-Br | H | COOMe(β) | H | H(β) |
| 6 | 6-NO₂ | H | COOMe(β) | H | H(β) |
| 7 | 6-OBz | H | COOMe(β) | H | H(β) |
| 8 | H | H | COOMe(β) | Me | H(β) |
| 9 | 6-OMe | H | COOMe(β) | Me | H(β) |
| 10 | 6-Br | H | COOMe(β) | Me | H(β) |
| 11 | H | H | COOMe(β) | H | Et(β) |
| 12 | H | H | COOMe(α) | H | H(β) |
| 13 | H | H | H | H | H(β) |
| 14 | H | H | COOH(β) | H | H(β) |
| 15 | 8-Me | H | COOH(β) | H | H(β) |
| 16 | 6-OMe | H | COOH(β) | H | H(β) |
| 17 | 6-OMe | 7-OMe | COOH(β) | H | H(β) |
| 18 | 6-Br | H | COOH(β) | H | H(β) |
| 19 | H | H | COOH(β) | CH₃ | H(β) |
| 20 | 6-OMe | H | COOH(β) | CH₃ | H(β) |
| 21 | 6-Br | H | COOH(β) | CH₃ | H(β) |
| 22 | H | H | COOH(β) | H | Et(β) |
| 23 | H | H | COOH(α) | H | H(β) |
| 24 | H | H | COO(2-BrEt)(β) | H | H(β) |
| 25 | H | H | NHCOOBz(β) | Me | H(β) |
| 26 | H | H | NH₂(β) | Me | H(β) |

Compounds of formula (I-2):

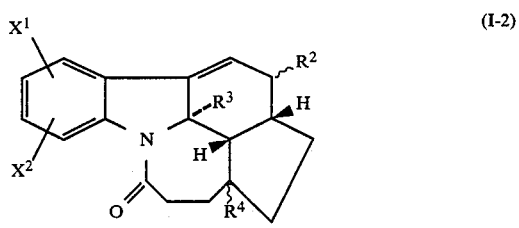

(I-2)

are as defined in Table 2.

TABLE 2

| Cpd No | $X^1$ | $X^2$ | $R^2$ | $R^3$ | $R^4$ |
|---|---|---|---|---|---|
| 27 | H | H | COOMe($\beta$) | H | H($\beta$) |
| 28 | H | H | COOH($\beta$) | H | H($\beta$) |

Compounds of formula (I-3):

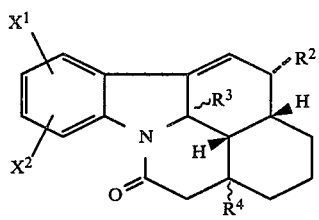

(I-3)

are as defined in Table 3.

TABLE 3

| Cpd No | $X^1$ | $X^2$ | $R^2$ | $R^3$ | $R^4$ |
|---|---|---|---|---|---|
| 29 | H | H | H | H | H($\beta$) |
| 30 | H | H | COOMe($\beta$) | H | H($\beta$) |
| 31 | 7-OBz | H | COOMe($\beta$) | H | H($\beta$) |
| 32 | H | H | COOMe($\beta$) | H | Et($\beta$) |
| 33 | H | H | COOMe($\beta$) | Me | H($\beta$) |
| 34 | H | H | COOH($\beta$) | Me | H($\beta$) |

Compounds of formula (I-4):

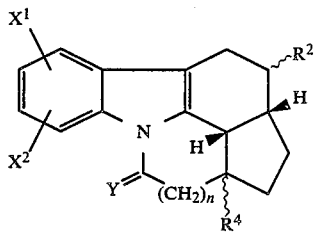

(I-4)

are as defined in Table 4.

TABLE 4

| Cpd No | $X^1$ | $X^2$ | Y | $R^2$ | $R^4$ | n |
|---|---|---|---|---|---|---|
| 35 | H | H | O | COOMe($\beta$) | H($\beta$) | 1 |
| 36 | 6-OMe | H | O | COOMe($\beta$) | H($\beta$) | 1 |
| 37 | 8-Me | H | O | COOMe($\beta$) | H($\beta$) | 1 |
| 38 | 6-Br | H | O | COOMe($\beta$) | H($\beta$) | 1 |
| 39 | 6-OMe | 7-OMe | O | COOMe($\beta$) | H($\beta$) | 1 |
| 40 | H | H | O | COOBz($\beta$) | H($\beta$) | 1 |
| 41 | H | H | $H_2$ | COOMe($\beta$) | H($\beta$) | 1 |
| 42 | H | H | O | H($\beta$) | H($\beta$) | 1 |
| 43 | H | H | O | COOMe($\beta$) | Et($\beta$) | 1 |
| 44 | H | H | $H_2$ | COOH($\beta$) | H($\beta$) | 1 |
| 45 | H | H | O | COOH($\beta$) | H($\beta$) | 1 |
| 46 | H | H | O | COOH($\beta$) | Et($\beta$) | 1 |
| 47 | H | H | O | NHCOOBz($\beta$) | H($\beta$) | 1 |
| 48 | H | H | O | NHCOOMe($\beta$) | H($\beta$) | 1 |
| 49 | 8-Me | H | O | NHCOOBz($\beta$) | H($\beta$) | 1 |
| 50 | 6-OMe | H | O | NHCOOBz($\beta$) | H($\beta$) | 1 |
| 51 | H | H | O | NHCOOBz($\beta$) | Et($\beta$) | 1 |
| 52 | H | H | O | NHCOOBz($\beta$) | H($\beta$) | 2 |
| 53 | H | H | $H_2$ | NHCOOBz($\beta$) | H($\beta$) | 1 |
| 54 | H | H | O | NHCOOBrn($\beta$) | H($\beta$) | 1 |
| 55 | H | H | O | $NH_2$($\beta$) | H(($\beta$) | 1 |
| 56 | 6-OMe | H | O | $NH_2$($\beta$) | H($\beta$) | 1 |
| 57 | 8-Me | H | O | $NH_2$($\beta$) | H($\beta$) | 1 |
| 58 | H | H | O | $NH_2$($\alpha$) | H($\beta$) | 1 |
| 59 | H | H | O | $NH_2$($\beta$) | Et($\beta$) | 1 |
| 60 | H | H | O | $NH_2$($\beta$) | H($\beta$) | 2 |
| 61 | H | H | $H_2$ | $NH_2$($\beta$) | H($\beta$) | 1 |
| 62 | H | H | O | NHPr($\beta$) | H($\beta$) | 1 |
| 63 | 6-OMe | H | O | NHBz($\beta$) | H($\beta$) | 1 |
| 64 | 8-Me | H | O | NHBz($\beta$) | H($\beta$) | 1 |
| 65 | 8-Me | H | O | $N(Me)_2$($\beta$) | H($\beta$) | 1 |

Compounds of formula (I-5):

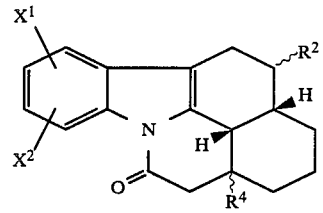

(I-5)

are as defined in Table 5.

TABLE 5

| Cpd No | $X^1$ | $X^2$ | $R^2$ | $R^4$ |
|---|---|---|---|---|
| 66 | H | H | COOEt($\beta$) | H($\beta$) |
| 67 | H | H | COOMe($\beta$) | H($\beta$) |
| 68 | 7-OBz | H | COOMe($\beta$) | H($\beta$) |
| 69 | H | H | COOMe($\beta$) | Et($\beta$) |
| 70 | H | H | COOMe($\beta$) | Me($\beta$) |
| 71 | H | H | COOMe($\beta$) | All($\beta$) |
| 72 | H | H | COOMe($\beta$) | 2-PhEt($\beta$) |
| 73 | H | H | COOH($\beta$) | Et($\beta$) |
| 74 | H | H | COOH($\beta$) | Me($\beta$) |
| 75 | H | H | COOH($\beta$) | All($\beta$) |
| 76 | H | H | COOH($\beta$) | 2-PhEt($\beta$) |
| 77 | H | H | COOH($\beta$) | H($\beta$) |
| 78 | 7-OBz | H | COOH($\beta$) | H($\beta$) |
| 79 | H | H | —$CON(Me)_2$($\beta$) | H($\beta$) |
| 80 | H | H | $CONH_2$($\beta$) | H($\beta$) |
| 81 | H | H | —$CON(iPr)_2$($\beta$) | H($\beta$) |
| 82 | H | H | —COPrl($\beta$) | H($\beta$) |
| 83 | H | H | —CO(4-MePip)($\beta$) | H($\beta$) |
| 84 | H | H | —CO(4-PhPip)($\beta$) | H($\beta$) |
| 85 | H | H | CO(2-BrEt)($\beta$) | H($\beta$) |
| 86 | H | H | NHCOOBz($\beta$) | H($\beta$) |
| 87 | H | H | NHCOOBz($\alpha$) | H($\beta$) |
| 88 | 7-OBz | H | NHCOOBz($\beta$) | H($\beta$) |
| 89 | H | H | NHCOOBz($\beta$) | Et($\beta$) |
| 99 | H | H | NHCOOBz($\beta$) | Me($\beta$) |

TABLE 5-continued

| Cpd No | X¹ | X² | R² | R⁴ |
|---|---|---|---|---|
| 91 | H | H | NHCOOBz(β) | All(β) |
| 92 | H | H | NHCOOBz(α) | All(β) |
| 93 | H | H | NHCOOBz(β) | 2-PhEt(β) |
| 94 | H | H | NHCO(4-mToPip) | H(β) |
| 95 | H | H | NH₂(β) | Me(β) |
| 96 | H | H | NH₂(β) | Pr(β) |
| 97 | H | H | NH₂(β) | All(β) |
| 98 | H | H | NH₂(β) | 2-PhEt(β) |
| 99 | H | H | NH₂(α) | Pr(β) |
| 100 | H | H | —N(Me)₂(β) | H(β) |
| 101 | H | H | —N(Me)₂(β) | Et(β) |
| 102 | H | H | —N(Me)₂(β) | Me(β) |
| 103 | H | H | —N(Me)₂(α) | Pr(β) |
| 104 | H | H | —N(Me)₃⁺I⁻(β) | H(β) |
| 105 | H | H | —N(Me)₃⁺I⁻(β) | Et(β) |
| 106 | H | H | NH₂(β) | H(β) |
| 107 | 7-OH | H | NH₂(β) | H(β) |
| 108 | 7-OMe | H | NH₂(β) | H(β) |
| 109 | H | H | NH₂(α) | H(β) |
| 110 | H | H | NH₂(β) | Et(β) |
| 111 | 6-OH | H | NH₂(β) | H(β) |
| 112 | 6-OH | H | NH₂(β) | Me(β) |
| 113 | 7-OH | 8-OH | NH₂(β) | Me(β) |
| 114 | 7-OH | H | NH₂(α) | Et(β) |
| 115 | 6-OH | H | NH₂(β) | Pr(β) |
| 116 | 7-OH | 8-OH | NH₂(β) | Pr(β) |
| 117 | 6-OH | H | NH₂(β) | iPr(β) |
| 118 | 6-OH | H | NH₂(β) | 4-OMe—PhEt(β) |
| 119 | 7-OH | H | NH₂(β) | 4-OMe—PhEt(β) |
| 120 | 6-OH | H | NH₂(β) | 3,4-diOMe—PhEt(β) |
| 121 | 7-OH | H | NH₂(β) | 3,4-diOMe—PhEt(β) |
| 122 | 6-OH | H | NH₂(β) | 3,4,5-triOMe—PhEt(β) |
| 123 | 6-OH | H | NMe₂(β) | Me(β) |
| 124 | 7-OH | H | NMe₂(β) | Me(β) |
| 125 | 6-OH | H | NMe₂(β) | Et(β) |
| 126 | 7-OH | H | NMe₂(β) | Et(β) |
| 127 | 6-OH | H | NMe₂(β) | 3,4-diOMe—PhEt(β) |
| 128 | 7-OH | H | NMe₂(β) | 3,4-diOMe—PhEt(β) |
| 129 | 6-OH | H | NMe₂(β) | 4-OMe—PhEt(β) |
| 130 | 7-OH | H | NMe₂(β) | 4-OMe—PhEt(β) |
| 131 | 6-OH | H | NHCOCH₂NEt₂(β) | Et(β) |
| 132 | 7-OH | H | NHCOCH₂NEt₂(β) | Et(β) |
| 133 | 6-OH | H | CONHNMe₂(β) | Et(β) |
| 134 | 7-OH | H | CONHNMe₂(β) | Et(β) |
| 135 | 6-OH | H | CONHNMe₂(β) | 4-OMe—PhEt(β) |
| 136 | 6-OH | H | CONHNMe₂(β) | 3,4-diOMePhEt(β) |
| 137 | 6-OH | H | CONHNH₂(β) | Et(β) |
| 138 | 7-OH | H | CONHNH₂(β) | Et(β) |
| 139 | 6-OH | H | CONHNH₂(β) | 3,4-diOMe—PhEt(β) |
| 140 | 6-OH | H | COO(4-MePip—Et)(β) | Et(β) |
| 141 | 6-OH | H | OH—Et—NHNHCO—(β) | Et(β) |
| 142 | 7-OH | H | OH—Et—NHNHCO—(β) | Et(β) |
| 143 | 6-OH | H | OH—Et—NHNHCO—(β) | 3,4-diOMe—PhEt(β) |
| 144 | 6-OH | H | CONHNHPh(β) | Et(β) |
| 145 | 6-OH | H | CONHNH(Prl—Et)(β) | Me(β) |
| 146 | 7-OH | H | CONHNH(Prl—Et)(β) | Et(β) |
| 147 | 6-OH | H | CONHNH(Prl—Et)(β) | 3,4-diOMe—PhEt(β) |
| 148 | 6-OH | H | CONHNH(Pid—Et)(β) | Me(β) |
| 149 | 6-OH | H | CONHNH(Pid—Et)(β) | 4-OMe—PhEt(β) |
| 150 | 6-OH | H | CONHNH(Pid—Et)(β) | 3,4-diOMe—PhEt(β) |
| 151 | 6-OH | H | CONHNH(4-MePip—Et)(β) | Et(β) |
| 152 | 6-OH | H | CONHNH(4-MePip—Et)(β) | 3,4-diOMe—PhEt(β) |
| 153 | 6-OH | H | CONHNHMe(β) | Et(β) |
| 154 | 6-OH | H | CONHNHMe(β) | 3,4-diOMe—PhEt(β) |
| 155 | 7-OBz | H | COOAll(β) | Ph(β) |
| 156 | 7-OBz | H | COOH(β) | Ph(β) |
| 157 | 7-OBz | H | NHCOOBz(β) | Ph(β) |
| 158 | 7-OBz | H | NH₂(β) | Ph(β) |
| 159 | 7-OBz | H | CONH(Prl—Et)(β) | Et(β) |
| 160 | 7-OBz | H | CONHNH(Prl—Et)(β) | Et(β) |
| 161 | 7-OH | H | CONH(Prl—Et)(β) | Et(β) |
| 162 | 7-OH | H | NH₂(β) | Ph(β) |
| 163 | 7-OBz | H | COOMe(β) | Me(β) |
| 164 | 7-OBz | H | COOMe(β) | Et(β) |
| 165 | 7-OBz | H | COOMe(β) | Pr(β) |
| 166 | 7-OBz | H | COOMe(β) | 2-PhEt(β) |
| 167 | 6-OBz | H | COOMe(β) | Et(β) |
| 168 | 6-OBz | H | COOMe(β) | 2-PhEt(β) |
| 169 | 7-OBz | 8-OBz | COOMe(β) | Et(β) |
| 170 | 7-OBz | 8-OBz | COOMe(β) | 2-PhEt(β) |

TABLE 5-continued

| Cpd No | $X^1$ | $X^2$ | $R^2$ | $R^4$ |
|---|---|---|---|---|
| 171 | 7-OBz | H | COOH($\beta$) | Me($\beta$) |
| 172 | 7-OBz | H | COOH($\beta$) | Et($\beta$) |
| 173 | 7-OBz | H | COOH($\beta$) | Pr($\beta$) |
| 174 | 7-OBz | H | COOH($\beta$) | iPr($\beta$) |
| 175 | 7-OBz | H | COOH($\beta$) | Bu($\beta$) |
| 176 | 7-OBz | H | COOH($\beta$) | 2-PhEt($\beta$) |
| 177 | 7-OBz | H | COOH($\beta$) | Bz($\beta$) |
| 178 | 7-OBz | H | COOH($\beta$) | 3,4-diOMePhEt($\beta$) |
| 179 | 6-OBz | H | COOH($\beta$) | Et($\beta$) |
| 180 | 6-OBz | H | COOH($\beta$) | 2-PhEt($\beta$) |
| 181 | 7-OBz | 8-OBz | COOH($\beta$) | Et($\beta$) |
| 182 | 7-OBz | 8-OBz | COOH($\beta$) | 2-PhEt($\beta$) |
| 183 | 7-OBz | H | NHCOOBz($\beta$) | Me($\beta$) |
| 184 | 7-OBz | H | NHCOOBz($\beta$) | Et($\beta$) |
| 185 | 7-OBz | H | NHCOOBz($\beta$) | Pr($\beta$) |
| 186 | 7-OBz | H | NHCOOBz($\beta$) | iPr($\beta$) |
| 187 | 7-OBz | H | NHCOOBz($\beta$) | Bu($\beta$) |
| 188 | 7-OBz | H | NHCOOBz($\beta$) | 2-PhEt($\beta$) |
| 189 | 7-OBz | H | NHCOOBz($\beta$) | Bz($\beta$) |
| 190 | 7-OBz | H | NHCOOBz($\beta$) | 3,4-diOMePhEt($\beta$) |
| 191 | 6-OBz | H | NHCOOBz($\beta$) | Et($\beta$) |
| 192 | 6-OBz | H | NHCOOBz($\alpha$) | Et($\beta$) |
| 193 | 6-OBz | H | NHCOOBz($\beta$) | 2-PhEt($\beta$) |
| 194 | 7-OBz | 8-OBz | NHCOOBz($\beta$) | Et($\beta$) |
| 195 | 7-OBz | 8-OBz | NHCOOBz($\beta$) | 2-PhEt($\beta$) |
| 196 | 7-OH | H | NH$_2$($\beta$) | Me($\beta$) |
| 197 | 7-OH | H | NH$_2$($\beta$) | Et($\beta$) |
| 198 | 7-OH | H | NH$_2$($\beta$) | Pr($\beta$) |
| 199 | 7-OH | H | NH$_2$($\beta$) | iPr($\beta$) |
| 200 | 7-OH | H | NH$_2$($\beta$) | Bu($\beta$) |
| 201 | 7-OH | H | NH$_2$($\beta$) | 2-PhEt($\beta$) |
| 202 | 7-OH | H | NH$_2$($\beta$) | Bz($\beta$) |
| 203 | 7-OH | H | NH$_2$($\beta$) | 3,4-diOMePhEt($\beta$) |
| 204 | 6-OH | H | NH$_2$($\beta$) | Et($\beta$) |
| 205 | 6-OH | H | NH$_2$($\alpha$) | Et($\beta$) |
| 206 | 6-OH | H | NH$_2$($\beta$) | 2-PhEt($\beta$) |
| 207 | 7-OH | 8-OH | NH$_2$($\beta$) | Et($\beta$) |
| 208 | 7-OH | 8-OH | NH$_2$($\beta$) | 2-PhEt($\beta$) |
| 209 | H | H | H | Et($\beta$) |
| 210 | 7-OH | H | COO(4-MePip—Et)($\beta$) | Et($\beta$) |
| 211 | 6-OH | H | CONHN=CHPr($\beta$) | Et($\beta$) |
| 212 | 6-OH | H | CONHN=CHPr | Et |
| 213 | 6-OH | H | CONHN=CHPh($\beta$) | Et($\beta$) |
| 214 | 6-OH | H | CONHN=CHPh | Et |
| 215 | H | H | COOAll($\beta$) | Et($\beta$) |
| 216 | 7-OBz | H | COOAll($\beta$) | Et($\beta$) |
| 217 | 7-OBz | H | COOAll($\beta$) | Pr($\beta$) |
| 218 | 7-OBz | H | COOAll($\beta$) | iPr($\beta$) |
| 219 | 7-OBz | H | COOAll($\beta$) | Bu($\beta$) |
| 220 | 7-OBz | H | COOAll($\beta$) | Bz($\beta$) |
| 221 | 7-OBz | H | COOAll($\beta$) | 3,4-diOMe—PhEt($\beta$) |

Compounds of formula (I-6):

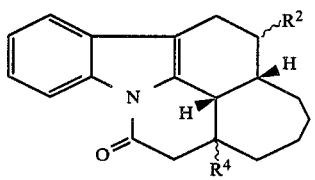

(I-6)

are as defined in Table 6.

TABLE 6

| Cpd No | $R^2$ | $R^4$ |
|---|---|---|
| 222 | COOMe($\beta$) | H($\beta$) |
| 223 | COOMe($\beta$) | H($\alpha$) |
| 224 | NHCOOBz($\beta$) | H($\beta$) |
| 225 | NHCOOBz($\beta$) | H($\alpha$) |
| 226 | NHCOOBz($\alpha$) | H($\beta$) |
| 227 | NHCOOBz($\alpha$) | H($\alpha$) |
| 228 | NH$_2$($\beta$) | H($\beta$) |
| 229 | NH$_2$($\beta$) | H($\alpha$) |
| 230 | NH$_2$($\alpha$) | H($\beta$) |
| 231 | NH$_2$($\alpha$) | H($\alpha$) |

Compounds of formula (I-7)

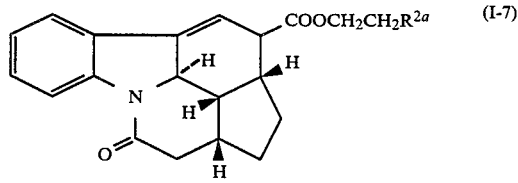

(I-7)

are as defined in Table 7.

TABLE 7

| Cpd No | R²ᵃ |
|---|---|
| 232 | Prl |
| 233 | Pid |
| 234 | Mor |
| 235 | 4-MePip |
| 236 | 4-mToPip |
| 237 | 4-(3,4,5-triMeO—Cin)Pip |

Compounds of formula (I-8):

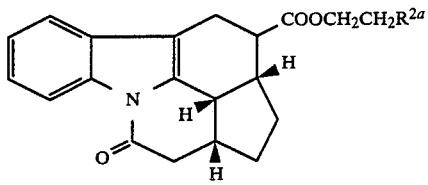

are as defined in Table 8.

TABLE 8

| Cpd No | R²ᵃ |
|---|---|
| 238 | Prl |
| 239 | Pid |
| 240 | Mor |
| 241 | 4-MePip |
| 242 | 4-mToPip |
| 243 | 4-(3,4,5-triMeO—Cin)-Pip |

Compounds of formula (I-9):

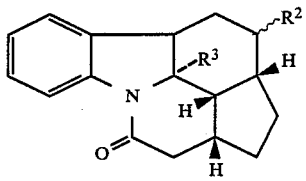

are as defined in Table 9.

TABLE 9

| Cpd No | R² | R³ |
|---|---|---|
| 244 | COOH(β) | H |
| 245 | COOMe(β) | H |
| 246 | NH₂(β) | Me |

Other examples of compounds of the invention are:
247. 1,2,2aβ,3α,11,11aβ,11bβ,11cα-Octahydro-6,7-dimethoxy-3β-[4-(3,4,5-trimethoxycinnamoyl)1-piperazinylcarbonyl]cyclopenta[d,e]indolo[3,2,1-i,j]quinolin-10-one
248. 4β-Amino-12aβ-ethyl-6-hydroxy-5α-methyl-2,3,3aβ,4α,5β,12,12aβ,12bβ-octahydrobenzo[d,e]indolo[3,2,1-i,j]quinolin-11(1H)-one
249. 4β-Amino-12aβ-ethyl-6-hydroxy-5β-methyl-2,3,3aβ,4α,5β,12,12aβ,12bβ-octahydrobenzo[d,e]indolo[3,2,1-i,j]quinolin-11(1H)-one Of the compounds listed above, preferred compounds are those of formula (I-5), particularly Compounds No. 107, 111-154, 196-199, 204, 205 and 207.

Certain of the intermediate compounds employed in preparing the compounds of the invention are also novel and certain of these intermediates are defined by the following formulae (VI-10) and (VI-11), as defined in the following Tables 10 and 11:

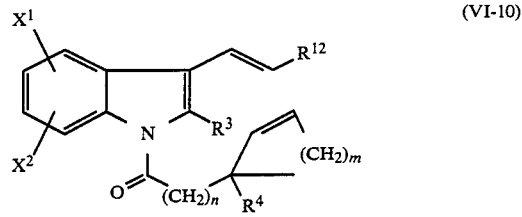

TABLE 10

| Cpd. No. | X¹ | X² | R³ | R⁴ | R¹² | n | m |
|---|---|---|---|---|---|---|---|
| P-1 | H | H | H | H | COOMe | 1 | 2 |
| P-2 | 7-Me | H | H | H | COOMe | 1 | 2 |
| P-2 | 5-OMe | H | H | H | COOMe | 1 | 2 |
| P-4 | 5-OMe | 6-OMe | H | H | COOMe | 1 | 2 |
| P-5 | 5-Br | H | H | H | COOMe | 1 | 2 |
| P-6 | 5-NO₂ | H | H | H | COOMe | 1 | 2 |
| P-7 | 5-OBz | H | H | H | COOMe | 1 | 2 |
| P-8 | H | H | Me | H | COOMe | 1 | 2 |
| P-9 | 5-OMe | H | Me | H | COOMe | 1 | 2 |
| P-10 | 5-Br | H | Me | H | COOMe | 1 | 2 |
| P-11 | H | H | H | Et | COOMe | 1 | 2 |
| P-12 | H | H | H | H | COOMe | 2 | 2 |
| P-13 | H | H | H | H | COOMe | 1 | 3 |
| P-14 | 5-OMe | H | H | H | COOMe | 1 | 3 |
| P-15 | H | H | H | Et | COOMe | 1 | 3 |
| P-16 | H | H | Me | H | COOMe | 1 | 3 |
| P-17 | H | H | H | H | H | 1 | 3 |
| P-18 | H | H | H | H | COOEt | 1 | 3 |
| P-19 | 5-OBz | H | H | H | COOMe | 1 | 3 |
| P-20 | H | H | H | Me | COOMe | 1 | 3 |
| P-21 | H | H | H | All | COOMe | 1 | 3 |
| P-22 | H | H | H | PhEt | COOMe | 1 | 3 |
| P-23 | H | H | H | H | COOMe | 1 | 4 |

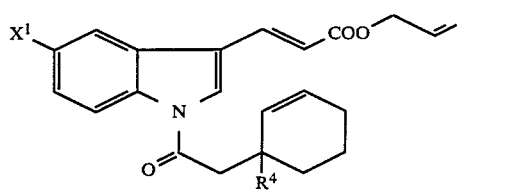

TABLE 11

| Cpd No | X¹ | R⁴ |
|---|---|---|
| P-24 | H | Et |
| P-25 | OBz | Et |
| P-26 | OBz | Pr |
| P-27 | OBz | iPr |
| P-28 | OBz | Bu |
| P-29 | OBz | Bz |
| P-30 | OBz | 3,4-diOMe—PhEt |

Another example of an intermediate of formula (VII) as shown hereafter where Y represents two hydrogen atoms is:

P-31. Methyl 3-{1-[2-(2-cyclopenten-1-yl)ethyl]indol-3-yl}acrylate.

Certain of the compounds of the invention, specifically compounds of formula (Ia):

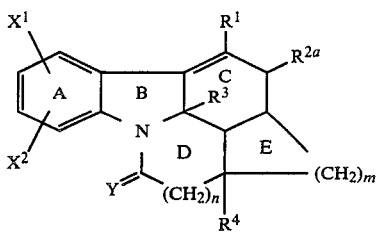

(in which $R^1$, $R^3$, $R^4$, $X^1$, $X^2$, Y, m and n are as defined above and $R^{2a}$ represents a hydrogen atom, a $C_2$-$C_7$ alkoxycarbonyl group, a $C_2$-$C_7$ alkoxycarbonyl group in which the alkyl part has from 1 to 3 of the substituents defined above, an aralkyloxycarbonyl group in which the aryl part is a $C_6$-$C_{10}$ carbocyclic aryl group and the alkyl part is a $C_1$-$C_6$ alkyl group, an aralkyloxycarbonyl group in which the alkyl part is a $C_1$-$C_6$ alkyl group and the aryl part is a $C_6$-$C_{10}$ carbocyclic aryl group having from 1 to 3 substituents as defined above, an alkenyloxycarbonyl group in which the alkenyl part is a $C_3$-$C_6$ alkenyl group, or a haloalkenyloxycarbonyl group in which the alkenyl part is a $C_3$-$C_6$ alkenyl group), and esters thereof where $X^1$ or $X^2$ represents a carboxy group, may be prepared by the intramolecular cyclization of a compound of formula (VII):

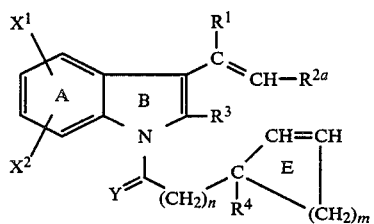

(in which $R^1$, $R^{2a}$, $R^3$, $R^4$, $X^1$, $X^2$, Y, m and n are as defined above) or an ester thereof.

The resulting compound of formula (Ia) or ester thereof may then be subjected, in any appropriate order, to one or more of the following reactions to prepare the appropriate other compounds of formula (I); when $R^{2a}$ represents an ester group (i.e. one of the aforementioned oxycarbonyl groups), converting this to the corresponding carboxylic acid, carboxylic acid amide, substituted alkoxycarbonyl, urethane, urea or amino group; reducing the double bond in the ring "C"; or, where $R^3$ represents a hydrogen atom, isomerizing that double bond to the position between the two carbon atoms common to the rings marked "B" and "C".

Preferred substituents represented by $R^{2a}$ in the compounds of formulae (Ia) and (VII) include the various oxycarbonyl groups defined in relation to the group represented by $R^{2'}$ in the compounds of formula (IV). However, preferred substituents include the hydrogen atom and the methoxycarbonyl, ethoxycarbonyl, benzyloxycarbonyl, p-nitrobenzyloxycarbonyl, allyloxycarbonyl, 2-methyl-2-propenyloxycarbonyl and 2-chloroallyloxycarbonyl groups.

The intramolecular cyclization reaction to prepare the compound of formula (Ia) from the compound of formula (VII) may be carried out under conditions well-known for such cyclization reactions, in the presence or absence of a catalyst and in the presence or absence of a solvent.

Where a solvent is employed for this reaction, the nature of the solvent is not critical, provided that it does not adversely affect the reaction. Examples of preferred solvents include: hydrocarbons, particularly aromatic and cycloaliphatic hydrocarbons, such as benzene, toluene, xylene, mesitylene, tetrahydronaphthalene, decahydronaphthalene and biphenyl; halogenated hydrocarbons, such as methylene chloride, chloroform, chlorobenzene and o-dichlorobenzene; ethers, such as diethyl ether, tetrahydrofuran, dioxane or diphenyl ether; amides, such as dimethylformamide or dimethylacetamide; dialkylaniline derivatives, such as N,N-dimethylaniline or N,N-diethylaniline; and liquid heat transfer media, such as that sold under the trade mark "Dowtherm".

Where a catalyst is employed, suitable catalysts include metal and metalloid compounds, particularly halides, such as aluminum chloride, zinc chloride, stannic chloride, ferric chloride, titanium tetrachloride, ethylaluminum chloride, dimethylaluminum chloride, diethylaluminum chloride and boron trifluoride.

The reaction is preferably carried out under atmospheric or superatmospheric pressure and at ambient or elevated temperature (suitably at about the boiling point of the solvent employed). Most preferably, a high boiling point solvent is chosen from those referred to above and the reaction is carried out under reflux of this solvent, for example at a temperature of about 160° C. The time required for the reaction will vary, depending upon many factors, including the nature of the reagents, the presence or absence of a solvent and the presence or absence of a catalyst, but a period within the range from 5 minutes to 100 hours will normally suffice.

After completion of the reaction, the compound of formula (Ia) may be recovered from the reaction mixture by conventional means; alternatively, the compound may be employed, without intermediate isolation, in the subsequent reaction or reactions.

The compound of formula (Ia):

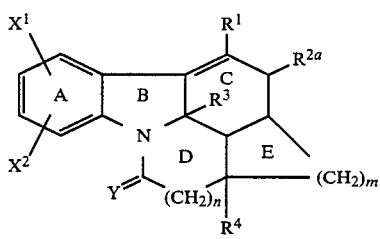

(in which $R^3$ represents a hydrogen atom) and its esters may be isomerized to give a compound of formula (Ib):

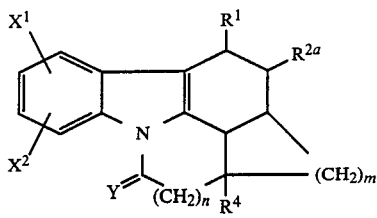

(in which $R^1$, $R^{2a}$, $R^4$, $X^1$, $X^2$, Y, m and n are as defined above) and its esters by treating the compound of formula (Ia) in a solvent in the presence or absence of a catalyst.

The reaction is preferably carried out in the presence of a catalyst, and suitable catalysts include metallic catalysts, such as palladium-on-carbon, metallic silver, metallic palladium, tris(triphenylphosphine)rhodium chloride, rhodium chloride, cupric chloride, iron pentacarbonyl or ruthenium chloride; or acidic catalysts (including Lewis acids), such as hydrochloric acid, sulfuric acid, nitric acid, phosphoric acid, acetic acid, methanesulfonic acid, p-toluenesulfonic acid or aluminum chloride; however, hydrochloric acid is most preferred.

There is no particular limitation on the nature of the solvent employed in this reaction, provided that it does not adversely affect the reaction. Suitable solvents include, for example: hydrocarbons, preferably aromatic hydrocarbons, such as benzene, toluene, xylene or mesitylene; alcohols, such as methanol, ethanol or propanol; ethers, such as tetrahydrofuran or dioxane; and amides, such as dimethylformamide or dimethylacetamide. The reaction may be carried out at ambient temperature or at elevated temperature, preferably under reflux by heating the reaction mixture at the boiling point of the solvent employed. The time required for the reaction will vary depending upon many factors, including the nature of the reagents, the presence or absence of a solvent and the temperature, but a period of from 1 minute to 10 hours will normally suffice.

The compounds of formulae (Ia) or (Ib) and their esters, preferably the compound of formula (Ia), may be reduced to give a compound of formula (Ic):

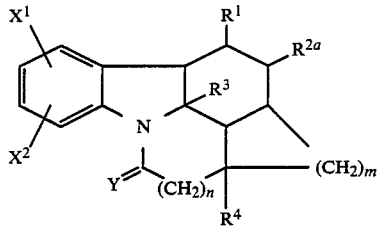

(in which $R^1$, $R^{2a}$, $R^3$, $R^4$, $X^1$, $X^2$, Y, m and n are as defined above) and its esters by catalytic hydrogenation.

The reaction may be carried out under conditions appropriate to conventional catalytic hydrogenation reactions, and will normally be effected at about ambient temperature. Catalysts commonly used in catalytic hydrogenation may be employed, including, for example: palladium-on-carbon, Raney nickel or platinum oxide. The reaction is preferably effected in the presence of a solvent, the nature of which is not critical, provided that it has no adverse effect upon the reaction. Suitable solvents include: alcohols, such as methanol or ethanol; ethers, such as tetrahydrofuran or dioxane; and amides, such as dimethylformamide or dimethylacetamide. The time required for the reaction will vary, depending upon many factors, but a period of from 10 minutes to 5 hours will normally suffice.

Where the group represented by $R^{2a}$ is an oxycarbonyl group (i.e. an alkoxycarbonyl group in which the alkyl part may be substituted or unsubstituted, an aralkyloxycarbonyl group in which the aryl part may be substituted or unsubstituted or an alkenyloxycarbonyl group in which the alkenyl part may be substituted or unsubstituted), this may be converted to a free carboxy group by various de-esterification reactions, including many conventional de-esterification reactions, depending upon the nature of the ester group which it is desired to remove.

Preferred reactions include hydrolysis, reductive elimination and catalytic elimination in the presence of a 0-valent palladium complex. The product is a compound of formula (Id):

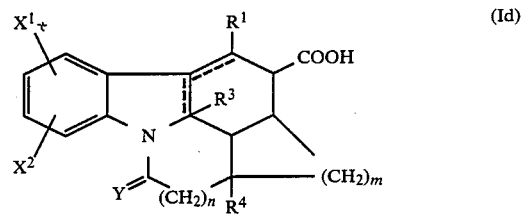

(in which $R^1$, $R^3$, $R^4$, $X^1$, $X^2$, Y, m, n and the dotted line are as defined above). The starting material for this reaction may be any of the compounds of formulae (Ia), (Ib) and (Ic) where $R^{2a}$ represents a group of formula —COOR$^a$ or an ester thereof (if $X^1$ or $X^2$ represents a carboxyl group).

Where $R^a$ represents a $C_1-C_6$ alkyl group (which may be unsubstituted or may have from 1 to 3 substituents as defined above), the hydrolysis of the ester to give the corresponding acid of formula (Id) may be carried out by means conventional for the hydrolysis of alkyl esters, for example by contacting the compound of formula (Ia), (Ib) or (Ic) with a hydroxide for an alkali metal, for example sodium hydroxide or potassium hydroxide. The reaction is preferably effected in the presence of a solvent, the nature of which is not critical, provided that it does not adversely affect the reaction. We prefer to employ a mixture of water and an organic solvent, for example: an alcohol, such as methanol or ethanol; or an ether, such as tetrahydrofuran or dioxane. The reaction temperature is not particularly critical, and, for convenience, we prefer to carry out the reaction at ambient temperature or at an elevated temperature up to the boiling point of the solvent employed. The time required for the reaction will vary depending upon many factors, primarily the reaction temperature, but a period of from 5 minutes to 2 days will normally suffice.

Where the compound of formula (Ia), (Ib) or (Ic) is a compound in which $R^a$ represents an aralkyl group, the de-esterification reaction is preferably carried out by the catalytic hydrogenation conventional for this type of de-esterification. The reaction is preferably effected at ambient temperature, employing a catalyst in the atmosphere of hydrogen. Suitable catalysts include: palladium-on-carbon, platinum oxide and Raney nickel. The reaction is preferably effected in the presence of a solvent, the nature of which is not critical, provided that it has no adverse effect upon the reaction. Suitable solvents include: alcohols, such as methanol or ethanol; ethers, such as tetrahydrofuran or dioxane; and amides, such as dimethylformamide or dimethylacetamide. The time required for the reaction will vary depending upon many factors, including the nature of the starting material, the nature of the catalyst and the reaction temperature, but a period of from 10 minutes to 5 hours will normally suffice.

Where the group represented by $R^a$ is an alkenyl group or substituted alkenyl group, this may be removed by contacting the compound of formula (Ia), (Ib) or (Ic) with a catalytic amount of a zero-valent palladium complex in the presence of a proton-donating compound and a ligand for palladium.

Suitable proton-donating compounds which may be employed in this reaction include: carboxylic acids, such as formic acid, acetic acid, propionic acid, butyric acid, isobutylic acid, 2-ethylhexanoic acid, cyclohexanecarboxylic acid, benzoic acid or anisic acid; alkali metal salts, for example the sodium or potassium salts, of these acids; phenols, such as phenol itself or cresol; alkali metal salts, such as the sodium salt or potassium salt, of these phenols; and the compounds having an active methylene group, such as diethyl malonate, ethyl cyanoacetate, malonitrile or methyl acetoacetate. The amount of proton-donating compound is preferably from 1 to 3 moles per mole of the compound of formula (Ia), (Ib) or (Ic).

The ligand for palladium may be chosen from any such compound commonly used in the field of organometallic complex chemistry. Suitable ligands which may be employed in this reaction include trivalent phosphorus compounds, such as triphenylphosphine, tributylphosphine or triethyl phosphite, of which triphenylphosphine is most preferred. The amount of ligand employed is preferably from 1 to 10 moles per mole of palladium complex.

Examples of suitable zero-valent palladium complexes include tetrakis(triphenylphosphine)palladium(O), palladium(O) bis(dibenzylideneacetone) and the like. The amount of such complex employed is preferably from 0.1 to 10 mole percent of the amount of the compound of formula (Ia), (Ib) or (Ic).

The reaction is preferably effected in the presence of a solvent, the nature of which is not critical, provided that it does not have any adverse effect upon the reaction. Suitable solvents include, for example: hydrocarbons, which may be aliphatic, cycloaliphatic or aromatic, such as hexane or benzene; halogenated hydrocarbons, such as methylene chloride or chloroform; ethers, such as diethyl ether, tetrahydrofuran or dioxane; alcohols, such as methanol, ethanol or t-butanol; ketones, such as acetone or methyl ethyl ketone; esters, such as methyl acetate or ethyl acetate; amides, such as dimethylformamide or dimethylacetamide; and dimethyl sulfoxide. A single one of these solvents or a mixture of any two or more of them may be employed.

The reaction is preferably effected under an atmosphere of an inert gas, such as nitrogen, and at a relatively low temperature, for example from 0° to 40° C. The reaction may be effected either with stirring or by simply standing the mixture. The time required for the reaction will depend upon many factors, notably the reaction temperature, but also the nature of the reagents and other reaction conditions; however a period of from 30 minutes to 24 hours will normally suffice.

The carboxylic acid of formula (Id):

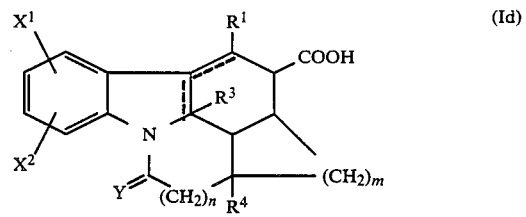

(in which $R^1$, $R^3$, $R^4$, $X^1$, $X^2$, Y, m, n and the dotted lines are as defined above), or a reactive derivative thereof, may be reacted with an amine of formula (VIII):

HNR$_2$           (VIII)

(in which the two symbols R are the same or different and are as defined above) to prepare a compound of formula (Ie):

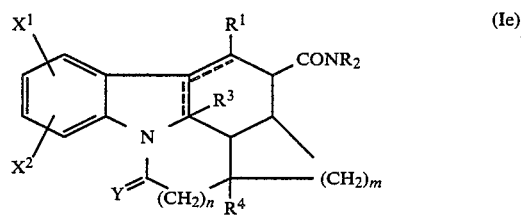

(in which R, $R^1$, $R^3$, $R^4$, $X^1$, $X^2$, Y, m, n and the dotted lines are as defined above).

In the resulting compound of formula (Ie), the group represented by —CONR$_2$ is an optionally substituted carbamoyl group, such as those heretofore defined in relation to the group $R^2$, for example a carbamoyl, N,N-dimethylcarbamoyl, 1-pyrrolidinylcarbonyl or 4-methyl-1-piperazinylcarbonyl group.

This reaction is preferably effected in the presence of a solvent and in the presence of a condensing agent or a base.

Where the free carboxylic acid of formula (Id) is employed, the reaction is preferably effected in the presence of a solvent and of a condensing agent. Suitable condensing agents include, for example: dicyclohexylcarbodiimide, N,N'-carbonyldiimidazole, N,N'- carbonyl-s-triazine, N-hydroxyphthalimide or diethyl phosphorocyanidate, of which diethyl phosphorocyanidate is preferred. The reaction is also preferably carried out in the presence of a base, preferably an organic amine, such as triethylamine or 4-dimethylaminopyridine. The nature of the solvent employed in the reaction is not critical, provided that it has no adverse effect on the reaction. Suitable solvents include, for example: ethers, such as tetrahydrofuran, dioxane or diethyl ether; amides, such as dimethylformamide or dimethylacetamide; halogenated hydrocarbons, such as methylene chloride or chloroform; and aromatic hydrocarbons, such as benzene or toluene.

The reaction temperature is not particularly critical, but we normally find it convenient to carry out the reaction at ambient temperature or at an elevated temperature, e.g. about the boiling point of the solvent employed. The time required for the reaction will vary, depending upon many factors, notably the reaction temperature, but a period of from 1 hour to 2 days will normally suffice.

On the other hand, when an acid halide, for example the acid chloride, is employed as a reactive derivative of the carboxylic acid of formula (Id), the condensation of the acid halide with the amine compound of formula (VIII) is preferably effected in the presence of a solvent and optionally in the presence of a base. Suitable bases include those mentioned in relation to the reaction of the free carboxylic acid of formula (Id) with the amine (VIII). The nature of the solvent employed is not particularly critical, provided that the solvent has no adverse effect upon the reaction. However, suitable solvents include, for example: halogenated hydrocarbons, such as methylene chloride, chloroform, carbon tetrachloride or 1,2-dichloroethane; and aromatic hydrocarbons, such as benzene or toluene. The reaction temperature is likewise not critical, but, for convenience, we normally prefer to carry out the reaction at about ambient temperature or at around the boiling point of the solvent employed. The time required for the reaction will vary, depending upon many factors, notably the reaction temperature, but a period of from 5 minutes to 2 days will normally suffice.

Carboxylic acid halides, particularly chlorides, for use in this reaction can be prepared from the free carboxylic acid of formula (Id) by conventional means by contacting the carboxylic acid (Id) with a halogenating agent, such as thionyl chloride or oxalyl chloride.

An aminoalkyl ester of formula (If):

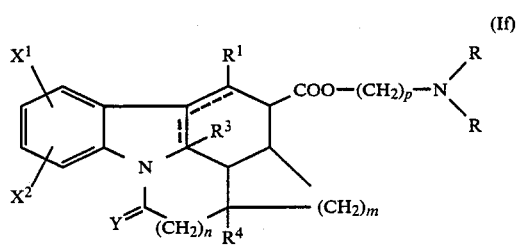

(in which $R^1$, $R^3$, $R^4$, $X^1$, $X^2$, Y, m, n, the dotted lines and the two symbols R are as defined above and p is one of the integers 1, 2, 3, 4, 5 or 6) may be prepared by treating the carboxylic acid of formula (Id) with a haloalkanol of formula (IX):

$$HO-(CH_2)_p-X^5 \quad (IX)$$

(in which $X^5$ represents a halogen atom, such as chlorine, bromine or iodine, and p is as defined above) to give a haloalkyl ester of formula (Ig):

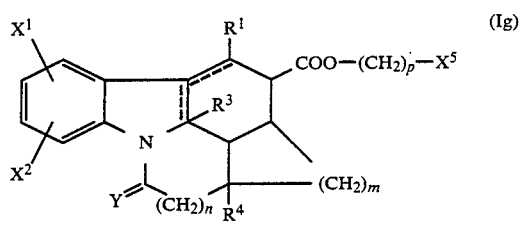

(in which $R^1$, $R^3$, $R^4$, $X^1$, $X^2$, $X^5$, Y, m, n, p and the dotted lines are as defined above), and then treating this haloalkyl ester (Ig) with an amine of formula (VIII):

$$HNR_2 \quad (VIII)$$

preferably in the presence of a solvent and of a condensing agent or base.

In the above formulae, p is preferably one of the integers 2 or 3.

The first condensation reaction of the carboxylic acid of formula (Id) with the haloalkanol (IX) is effected in a solvent and in the presence of a condensing agent. Suitable condensing agents include, for example: hydrogen chloride, sulfuric acid, dicyclohexylcarbodiimide, N,N'-carbonyldiimidazole and diethyl phosphorocyanidate, of which dicyclohexylcarbodiimide is preferred. The reaction may also be carried out, if required, in the presence of a base, for example: an organic base, such as triethylamine or 4-dimethylaminopyridine; or an alkali metal carbonate or hydrogen carbonate, such as sodium carbonate or sodium hydrogen carbonate. The solvent employed in this reaction is not particularly critical, provided that it does not adversely affect the reaction. Suitable solvents include, for example: aromatic hydrocarbons, such as benzene, toluene or xylene; ethers, such as tetrahydrofuran or dioxane; and amides, such as dimethylformamide. Of these, dioxane is preferred. The reaction temperature is not particularly critical, but we normally find it convenient to carry out the reaction at ambient temperature or at an elevated temperature, suitably around the boiling point of the solvent employed. The time required for the reaction will vary, depending upon many factors, notably the reaction temperature, but a period of from 10 minutes to 2 days will normally suffice.

The reaction of the resulting haloalkyl ester of formula (Ig) with the amine of formula (VIII) is effected in a solvent and optionally in the presence of a base. Suitable bases include: organic bases, such as triethylamine or pyridine; and alkali metal carbonates and hydrogen carbonates, such as sodium carbonate or sodium hydrogen carbonate. The nature of the solvent employed in this reaction is not critical, provided that it has no adverse effect upon the reaction. Suitable solvents include, for example: aromatic hydrocarbons, such as benzene, toluene or xylene; ethers, such as tetrahydrofuran or dioxane; amides, such as dimethylformamide; dimethyl sulfoxide; and esters of aliphatic carboxylic acids, such as methyl acetate or ethyl acetate. The reaction temperature is not particularly critical, but we normally find it convenient to carry out the reaction at around ambient temperature or at an elevated temperature, e.g. around the boiling point of the solvent employed. The time required for the reaction will vary, depending upon many factors, notably the reaction temperature, but a period of from 30 minutes to 24 hours will normally suffice.

The carboxylic acid of formula (Id) or a reactive derivative thereof can be used to prepare urethane and urea derivatives, for example as illustrated in the following reaction scheme:

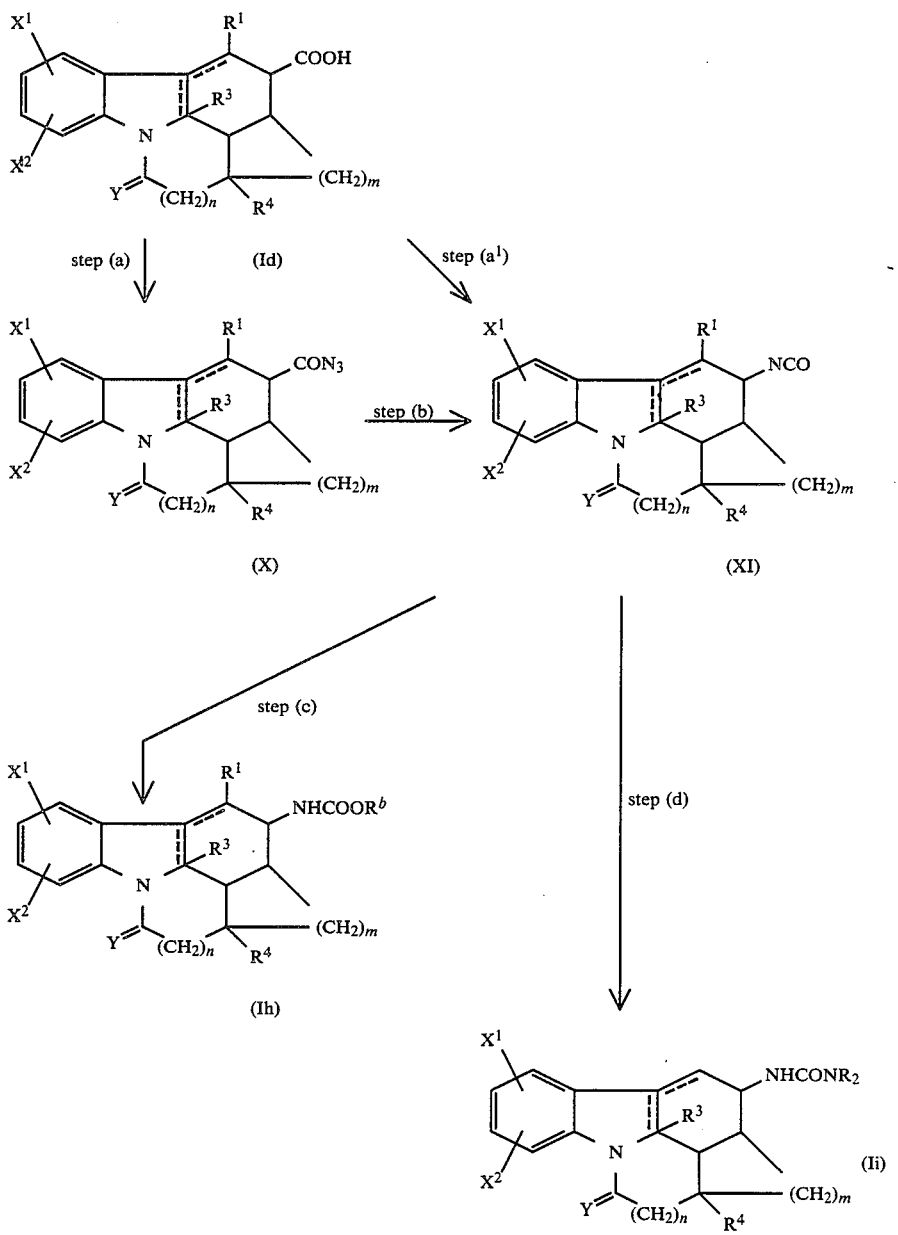

In the above formulae, $R^1$, $R^3$, $R^4$, $X^1$, $X^2$, Y, n, m, the dotted lines and the two symbols R are as defined above. $R^b$ represents an alkyl group, a substituted alkyl group, a $C_3$-$C_6$ alkenyl group, a $C_3$-$C_6$ haloalkenyl group, an aralkyl group, which may be substituted or unsubstituted, or a cycloalkyl group (which may be a terpenyl group). Accordingly, the group of formula —NHCOOR$^b$ can be any one of the protected carboxyamino groups defined in relation to $R^2$ in the compound of formula (I), for example a methoxycarbonylamino, benzyloxycarbonylamino, p-nitrobenzyloxycarbonylamino or isoborn-2-yloxycarbonylamino group. The group represented by the formula —NH.CO.NR$_2$ is a ureido group or a mono- or di-substituted ureido group as defined for $R^2$ of the compound of formula (I), for example a ureido group, an N,N-dimethylaminocarbonylamino group or a 4-phenyl-1-piperazinylcarbonylamino group.

In the above reaction scheme, in step (a) a carboxylic acid azide of formula (X) is prepared by contacting an acid halide of the compound of formula (Id) with sodium azide. The reaction is preferably effected in the presence of a solvent, the nature of which is not critical, provided that it has no adverse effect upon the reaction. We prefer to employ a 2-phase system comprising water and an essentially water-immiscible organic solvent, for example: a ketone, such as acetone or methyl ethyl ketone; an ether, such as tetrahydrofuran or dioxane; an ester of an aliphatic carboxylic acid, such as methyl acetate or ethyl acetate; a halogenated hydrocarbon, such as methylene chloride or chloroform; or an aromatic hydrocarbon, such as benzene, toluene or xylene. The reaction is preferably effected with ice-cooling or at about ambient temperature and the time required for the reaction, which will depend primarily upon the reaction temperature, is usually from 5 minutes to 3 hours.

The carboxylic acid azide of formula (X) can also be prepared by contacting sodium azide with a mixed acid anhydride. This mixed acid anhydride can be prepared by contacting the carboxylic acid of formula (Id) with ethyl chloroformate in the presence of a base, such as triethylamine. The solvents, reaction temperatures and times required are essentially the same as those discussed above in relation to the use of acid chloride.

The reaction product of step (a) is normally and preferably employed without intermediate isolation for the reaction in step (b).

In step (b) an isocyanate of formula (XI) is prepared by submitting the carboxylic acid azide of formula (X) to a Curtius rearrangement reaction, such as is well-known in the art. The reaction is effected in the presence of a solvent, the nature of which is not critical, provided that it has no adverse effect upon the reaction. Suitable solvents include, for example: aromatic hydrocarbons, such as benzene, toluene, xylene or mesitylene; halogenated hydrocarbons, such as chloroform or 1,2-dichloroethane; ethers, such as tetrahydrofuran or dioxane; ketones, such as acetone or methyl ethyl ketone; and aliphatic carboxylic acid amides, such as dimethylformamide or dimethylacetamide.

The reaction is preferably effected at elevated temperature, for example by heating up to the boiling point of the solvent employed. The time required for the reaction will vary, depending upon many factors, notably the reaction temperature, but a period of from 5 minutes to 6 hours will normally suffice.

The isocyanate compound of formula (XI) can also be prepared in step (a') directly from the carboxylic acid of formula (Id) by heating the carboxylic acid with diphenylphosphoryl azide, in the presence of an organic base, such as triethylamine. The solvents, reaction temperatures and times are essentially the same as those used in the Curtius rearrangement reaction.

In steps (c) and (d), the urethane derivative of formula (Ih) and the urea derivative of formula (Ii) are prepared by contacting the isocyanate compound of formula (XI) with, respectively, an alcohol of formula (XII):

$R^b$—OH  (XII)

or an amine of formula (VIII):

HNR$_2$  (VIII)

The reaction is preferably effected in the presence of a solvent, the nature of which is not critical, provided that it has no adverse effect upon the reaction. Suitable solvents include: aromatic hydrocarbons, such as benzene, toluene or xylene; halogenated hydrocarbons, such as methylene chloride or chloroform; ethers, such as tetrahydrofuran or dioxane; and amides, such as dimethylformamide or dimethylacetamide. The reaction temperature is not particularly critical and, for convenience, we normally prefer to carry out the reaction at ambient temperature or by heating the reaction mixture to about the boiling point of the solvent employed. The time required for the reaction will vary depending upon many factors, notably the reaction temperature, but a period of from 5 minutes to 5 hours will normally suffice.

An amino compound of formula (Ij):

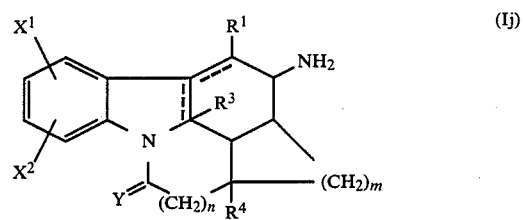

(in which $R^1$, $R^3$, $R^4$, $X^1$, $X^2$, Y, n and m and the dotted lines are as defined above) can be prepared by the catalytic reduction of a urethane derivative of formula (Ih'):

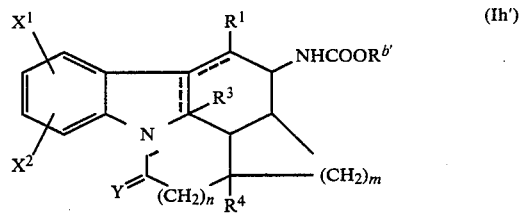

(in which $R^1$, $R^3$, $R^4$, $X^1$, $X^2$, Y, n and m and dotted lines are as defined above). The reaction is preferably effected in a solvent, employing a catalyst in an atmosphere of hydrogen.

In the above formula, $R^{b'}$ preferably represents an aralkyl group (which may be substituted or unsubstituted) for example a benzyl or p-nitrobenzyl group.

The reaction is carried out under the same conditions as conventional catalytic reduction reactions, preferably at about ambient temperature. Suitable catalysts include, for example: palladium-on-carbon, platinum oxide, Raney nickel, platinum black, rhodium-on-carbon and rhodium/alumina. There is no particular limitation on the nature of the solvent to be employed in this reaction, provided that it has no adverse effect upon the reaction. Suitable solvents include, for example: alcohols, such as methanol or ethanol; ethers, such as tetrahydrofuran or dioxane; amides, such as dimethylformamide or dimethylacetamide; and lower aliphatic acids, such as acetic acid. The reaction is commonly and preferably conducted at atmospheric pressure and at ambient temperature. The time required for the reaction will vary, depending upon many factors, but a period of from 10 minutes to 5 hours will normally suffice.

The amino compound of formula (Ij) can also be prepared by reacting the urethane compound of formula (Ih') in which $R^{b'}$ represents a benzyl group with a mixture of trifluoroacetic acid and thioanisole or dimethyl sulfide at about ambient temperature.

The amino compound of formula (Ij) can also be obtained by reacting the urethane compound of formula (Ih) in which $R^b$ represents a t-butoxy group with a catalytic amount of an acid. Suitable acids include, for example: such mineral acids as hydrochloric acid; such carboxylic acids as trifluoroacetic acid; and such organic sulfonic acids as p-toluenesulfonic acid. The reaction is preferably effected in the presence of a solvent, the nature of which is not critical, provided that it has no adverse effect upon the reaction. Suitable solvents include, for example: alcohols, such as methanol or ethanol; ethers, such as tetrahydrofuran or dioxane; halogenated hydrocarbons, preferably halogenated aliphatic hydrocarbons, such as methylene chloride or chloroform; and aromatic hydrocarbons, such as benzene or toluene. There is no particular limitation on the reaction temperature, but, for convenience, we normally prefer to carry out the reaction at about ambient temperatue or at the boiling point of the solvent employed. The time required for the reaction will vary, depending upon many factors, notably the reaction temperature, but a period of from 10 minutes to 2 days will normally suffice.

The amino compound of formula (Ij) may be converted to the corresponding mono- or di-substituted amino compound or the corresponding quaternary ammonium salt by conventional means, by reacting the compound of formula (Ij) with an alkyl halide or aralkyl halide (wherein the alkyl or aralkyl groups, respectively, may be substituted or unsubstituted).

The reaction is preferably effected in the presence of a solvent, the nature of which is not critical, provided that it has no adverse effect upon the reaction. Suitable solvents include, for example: ethers, such as tetrahydrofuran or dioxane; alcohols, such as methanol, ethanol or propanol; halogenated hydrocarbons, preferably halogenated aliphatic hydrocarbons, such as methylene chloride, chloroform or 1,2-dichloroethane; aromatic hydrocarbons, such as benzene, toluene or xylene; amides, such as dimethylformamide or dimethylacetamide; and esters of aliphatic carboxylic acids, such as methyl acetate or ethyl acetate.

The reaction temperature is not particularly critical, but we normally find it convenient to carry out the reaction at an elevated temperature, e.g. up to about the boiling point of the solvent employed. The time required for the reaction may vary over a wide range depending upon many factors, notably the reaction temperature, but a period of from 30 minutes to 3 days will normally suffice.

The dimethylamino compound can also be prepared by a conventional alternative reaction, in which the amino compound of formula (Ij) is heated with formalin in formic acid.

At the end of any of the stages of the reactions described above, the desired compounds may be isolated and purified by conventional procedures, such as extraction, recrystallization or the various chromatography techniques, including column chromatography and preparative thin layer chromatography.

The starting materials of formula (VII) employed in the preparation of the compounds of the invention can be prepared by a variety of conventional means. The most convenient method is to react an alkali metal salt of a compound of formula (XX):

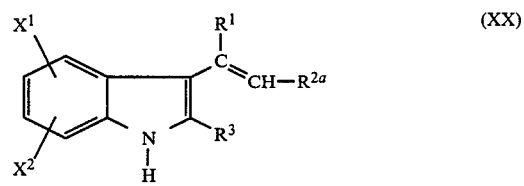

(in which $R^1$, $R^{2a}$, $R^3$, $X^1$ and $X^2$ are as defined above) with a reactive derivative of a compound of formula (XXI):

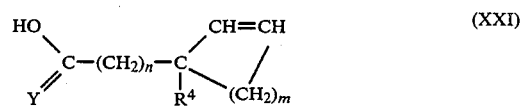

(in which $R^4$, Y, n and m are as defined above).

Where Y in said compound of formula (XXI) is an oxo group, the compound of formula (XXI) is a carboxylic acid and preferred reactive derivatives include, for example: acid halides, such as the acid chloride or acid bromide; and mixed acid anhydrides, for example that prepared by reacting the carboxylic acid with ethyl chloroformate in the presence of a base, such as triethylamine. Where Y represents two hydrogen atoms, the compound is an alcohol derivative and the preferred reactive derivative is a halide, such as the chloride, bromide or iodide.

This type of condensation between a cyclic amine and a reactive derivative of an acid or of an alcohol is well-known and is carried out under conditions conventional for this type of reaction.

The compounds of the present invention have a variety of valuable therapeutic effects. Thus, they have outstanding anti-arrhythmic effect, have a diuretic effect and improve brain function. They can, therefore, be used in the therapy of arrhythmia, urine retention and brain dysfunctions, both in humans and in many other animals. Examples of the activity of the compounds of the invention are illustrated as follows:

A. Anti-arrhythmic effect

The test was performed according to the method of L. H. Opie et al [Cardiovascular Research, 12, 212 (1978)] using male rats of Sprague-Dawley strain weighing between 230 and 330 g. The antiarrhythmic effect was estimated by the ability of the test compound administered intravascularly to protect against the arrhythmias induced by ischemic cardiac dysfunction caused by ligation of the coronary arteries of a perfusing heart.

The test compounds were dissolved in dimethyl sulfoxide, and the required amount of injectible solution was prepared by mixing this with Krebs-Henseleit solution. The degree of protecting effect is reported as the concentration ($ED_{70}$) required for 70% suppression of the arrhythmias during ligation and after re-perfusion. The results obtained are summarized in Table 12.

For comparison, the known compounds, Lidocaine and Disopyramide, were also tested, and these results are also shown in Table 12.

The compounds of the invention are identified by the numbers assigned to them in the foregoing Tables 1 to 9.

TABLE 12

| Cpd No | $ED_{70}$ (g/ml) |
| --- | --- |
| 26 | $9 \times 10^{-7}$ |
| 35 | $4.2 \times 10^{-6}$ |
| 55 | $6.4 \times 10^{-7}$ |
| 59 | $2.3 \times 10^{-7}$ |
| 65 | $3 \times 10^{-7}$ |
| 106 | $1 \times 10^{-6}$ |
| 110 | $1.6 \times 10^{-7}$ |
| 228 | $9 \times 10^{-7}$ |
| Lidocaine | $5 \times 10^{-6}$ |
| Disopyramide | $1 \times 10^{-5}$ |

B. Diuretic effect

The diuretic test was performed on groups of 5 male mice of the DDY strain, each weighing between 26 and 30 g. The test solutions were prepared by dissolving the test compounds in physiological saline containing 0.3% w/v carboxymethylcellulose and were administered orally to the animals. The urine volume and sodium ion concentration were estimated by the filter paper method [Mineshita et al: Pharmacometrics, 4, 33 (1970)]. In Table 13, the increase of the urine volume and sodium ion concentration are shown as a percentage of the values of a control group to which no active compound was administered.

TABLE 13

| Cpd No | Dose (p.o.) | Urine Volume (%) | $\delta Na^+$ (%) |
| --- | --- | --- | --- |
| 14 | 100 mg/kg | 231 | 245 |
| 18 | 100 mg/kg | 86 | 168 |

C. Improvement of brain function

A test for recovery of brain function was performed using rats with ischemic brains. The bilaterial carotid arteries of male rats of the Wistar strain were ligated under anesthesia with thiopental (50 mg/kg, intraperitoneally) and the test compounds and a 0.5% w/v carboxymethylcellulose solution (vehicle) were intraperitoneally administered at the same time. The time until recovery of the righting relex was measured to give an index of the brain function. Table 14 shows a comparison between the results obtained for the groups given the test compounds and a control group given only the vehicle. The known compound, Pentoxifylline, was tested in the same way, for comparison.

TABLE 14

| Cpd No | Dose (i.p.) | Ratio to Control |
| --- | --- | --- |
| 18 | 10 mg/kg | 0.84 |
|  | 30 mg//kg | 0.68 |
| (Reference Compound) Pentoxifylline | 30 mg/kg | 0.82 |

D. Anti-arrhythmic effect

Test procedures: (Block's method)

Onto a 2 liter desiccator were placed 150 ml of chloroform and this was stirred with a magnetic stirrer while being heating by an incandescent lamp. When the desiccator was saturated with chloroform gas, mice (ICR strain, body weight between 20 and 25 g) were placed therein for 2 minutes and then the chest was opened. Silver dipolar electrodes were contacted with the ventricles and electrocardiograms were taken for 1 minute. Within 10-20 minutes, the test compound was administered intraperitoneally in a carboxymethyl-cellulose solution as vehicle. When the heart beat rate in the ventricle was reduced to less than 400 beats/minute as measured by the electrocardiogram, such a test compound was evaluated as effective (+). [See, Alan J. Block, Life Sciences, 28, 2623–2629, 1981]

| Cpd No | $ED_{50}$% (mg/kg) |
| --- | --- |
| 96 | 3.6 |
| 110 | 14.0 |
| 146 | 22.5 |
| 162 | 12.0 |
| 197 | 22.5 |
| 198 | 4.2 |
| 204 | 6.0 |
| 205 | 10.0 |
| 207 | 7.0 |
| Quinidine (control) | 48.0 |

The invention, therefore, also provides a method of treating arrhythmia in a mammal (which may be human or non-human) by administering to said mammal an anti-arrhythmic compound, wherein the anti-arrhythmic compound is selected from the group consisting of compounds of formula (I) and pharmaceutically acceptable salts and esters thereof.

The compounds of the invention may be formulated, for therapeutic use, into various conventional formulations, the precise formulation chosen being dependent upon the route of administration. For example, for oral administration, the compounds can be formulated as tablets, capsules, powders or syrups. For parenteral administration, they can be formulated with injectible media for subcutaneous or intravenous injections. They can also be formulated as suppositories. The compounds will be mixed with various conventional carriers and diluents, for example: solubilizing agents, suspending agents, excipients, binders, disintegrating agents and optionally other therapeutically active compounds. The dosage will vary, depending upon the symptoms, age and body weight of the patient, as well as the nature and severity of the disorder, but a suitable dose for an adult human patient would be within the range from 20 to 200 mg per day, which can be administered as a single dose or in divided doses, e.g. 2 or 3 doses.

The preparation of various of the compounds of the invention is illustrated in the following Examples, whilst the preparation of certain starting materials is illustrated in the following Preparations. Various of the compounds of the invention are identified hereafter by the numbers assigned to them in the foregoing Tables 1 to 9, whilst certain of the intermediate compounds are identified by the numbers assigned to them in the foregoing Tables 10 and 11.

PREPARATION 1

Methyl (E)-3-[1-(2-cyclopenten-1-yl)acetyl-1H-indol-3-yl]acrylate (Compound No. P-1)

To a solution of 4.02 g of methyl (E)-3-(indol-3-yl)acrylate in 40 ml of N,N-dimethylformamide was added 0.96 g of 55% w/w suspension of sodium hydride in mineral oil, and the mixture was stirred at ambient temperature for 1 hour. The acid chloride prepared from 3.78 g of (2-cyclopenten-1-yl)acetic acid was added thereto, whilst ice-cooling, and the mixture was stirred for a further 2 hours. The reaction mixture was then poured into ice-water and extracted with methylene chloride. The extract was dried over anhydrous magnesium sulfate, and the solvent was removed by evaporation under reduced pressure to give a residue, which was purified by silica gel column chromatography, using a 1:1 by volume mixture of ethyl acetate and hexane as eluent, followed by recrystallization from hexane, to afford 5.05 g of the title compound as pale yellow needles melting at 105°–106.5° C.

Elemental Analysis: Calculated for $C_{19}H_{19}NO_3$: C, 73.77%; H, 6.19%; H, 4.53%. Found: C, 73.78%; H, 6.10%; N, 4.53%.

Infrared Absorption Spectrum (KBr) $\nu_{max}$cm$^{-1}$: 1710.

Nuclear Magnetic Resonance Spectrum (CDCl$_3$) δ ppm: 3.83 (3H, singlet); 5.7–5.95 (2H, multiplet); 8.4–8.65 (1H, multiplet).

Mass Spectrum (m/e): 309 (M+).

PREPARATION 2

Methyl (E)-3-[1-(2-cyclohexen-1-yl)acetyl-1H-indol-3-yl]acrylate (Compound No. P-13)

To a solution of 2.012 g of methyl (E)-3-(indol-3-yl)acrylate in 20 ml of N,N-dimethylformamide was added 0.48 g of a 55% w/w suspension of sodium hydride in mineral oil, and the mixture was stirred at ambient temperature for 0.5 hours. The acid chloride prepared from 2.10 g of (2-cyclohexen-1-yl)acetic acid was added, whilst ice-cooling, to the reaction mixture, and the mixture was stirred for a further 1 hour. It was then treated by the same procedures as described in Preparation 1, to afford 2.05 g of the title compound as pale yellow needles melting at 111°–113° C.

Elemental Analysis: Calculated for $C_{20}H_{21}NO_3$: C, 74.28%; H, 6.55%; N, 4.33%. Found: C, 74.26%; H, 6.51%; N, 4.33%.

Infrared Absorption Spectrum (KBr) $\nu_{max}$cm$^{-1}$: 1710.

Nuclear Magnetic Resonance Spectrum (CDCl$_3$) δ ppm: 3.80 (3H, singlet); 5.50–5.90 (2H, multiplet); 8.40–8.65 (1H, multiplet).

Mass Spectrum (m/e): 323 (M+).

Compounds No. P-2 to P-12 and P-14 to P-23 as shown in Table 10 and P-31 were prepared by the same procedures as described in Preparations 1 and 2.

Compound No. P-2, melting at 97°–99° C.
Compound No. P-3, melting at 127°–129° C.
Compound No. P-4, melting at 154.5°–155.5° C.
Compound No. P-5, melting at 160°–161.5° C.
Compound No. P-6, melting at 195°–197° C.
Compound No. P-7, melting at 133°–135° C.
Compound No. P-8, melting at 90°–93° C.
Compound No. P-9, melting at 75°–77° C.
Compound No. P-10, melting at 87°–89° C.
Compound No. P-11, melting at 82°–86° C.
Compound No. P-12, melting at 86°–87° C.
Compound No. P-14, melting at 134°–136° C.
Compound No. P-15, melting at 74°–76° C.
Compound No. P-16, a pale yellow oil
Compound No. P-17, a pale yellow oil
Compound No. P-18, melting at 88°–90° C.
Compound No. P-19, melting at 139°–141° C.
Compound No. P-20, melting at 104°–106° C.
Compound No. P-21, melting at 44°–46° C.
Compound No. P-22, a pale yellow oil
Compound No. P-23, melting at 103°–105° C.
Compound No. P-31, melting at 84°–86° C.

PREPARATION 3

Allyl (E)-3-(5-benzyloxy-1H-indol-3-yl)acrylate 17.45 g of a 55% w/w suspension of sodium hydride in mineral oil were suspended in 400 ml of toluene; to the resulting suspension were added 400 ml of allyl alcohol, whilst ice-cooling and under a nitrogen atmosphere. 122.93 g of methyl (E)-3-(5-benzyloxy-1H̄-indol-3-yl)acrylate were added thereto, and the mixture was heated under reflux for 10 minutes. The reaction mixture was then washed, in turn, with a saturated aqueous solution of citric acid, with a saturated aqueous solution of sodium hydrogen carbonate, with water and with a saturated aqueous solution of sodium chloride, and then dried over anhydrous magnesium sulfate. It was then condensed by evaporation under reduced pressure. The residue was purified by silica gel column chromatography using 20% v/v ethyl acetate in hexane as eluent, to give 100.12 g of the title compound as crystals melting at 73°–77° C.

PREPARATION 4

Allyl (E)-3-[5-benzyloxy-1-(1-ethyl-2-cyclohexen-1-yl)acetyl-1H-indol-3-yl]acrylate (Compound No. P-25)

23.34 g of allyl (E)-3-(5-benzyloxy-1H̄-indol-3-yl)acrylate (prepared as described in Preparation 3) were dissolved in 100 ml of N,N-dimethylformamide, and 3.36 g of a 55% w/w suspension of sodium hydride in mineral oil were added thereto. The mixture was then stirred for 30 minutes at room temperature, after which 14 g of (1-ethyl-2-cyclohexen-1-yl)acetyl chloride were added, whilst ice-cooling, and the mixture was stirred for a further 30 minutes. The reaction mixture was then poured into ice-water and extracted with methylene chloride. The extract was dried over anhydrous magnesium sulfate and condensed by evaporation under reduced pressure. The resulting residue was purified by silica gel column chromatography using a 1:9 by volume mixture of ethyl acetate and hexane as eluent, and the product was recrystallized from diisopropyl ether, to give 24.48 g of the title compound as colorless needles melting at 68°–72° C.

Elemental Analysis: Calculated for $C_{31}H_{33}NO_4$: C, 76.99%; H, 6.88%; N, 2.90%. Found: C, 77.02%; H, 6.93%; N, 2.74%.

Infrared Absorption Spectrum (KBr) $\nu_{max} cm^{-1}$: 1690.

Nuclear Magnetic Resonance Spectrum (CDCl$_3$) δ ppm: 8.47 (1H, doublet, J=9 Hz).

Mass Spectrum (m/e): 483 (M+).

Following essentially the same procedures as are described in Preparations 3 and 4, the following intermediate compounds were also prepared:
Compound No. P-24, an oil
Compound No. P-26, an oil
Compound No. P-27, an oil
Compound No. P-28, an oil
Compound No. P-29, a paste
Compound No. P-30, an oil

EXAMPLE 1

Methyl 1,2,2aβ,3α, 11,11aβ,11bβ,11cα-octahydro-10-oxo-10H-cyclopenta[d,e]indolo[3,2,1-i,j]quinoline-3β-carboxylate (Compound No. 1)

619 g of methyl (E)-3-[1-(2-cyclopenten-1-yl)acetyl-1H-indol-3-yl]acrylate (Compound No. P-1, prepared as described in Preparation 1) were added to 20 ml of mesitylene, and the mixture was heated under reflux for 4 hours. The reaction mixture was then condensed by evaporation under reduced pressure, and the residue was purified by silica gel column chromatography, eluted with a 1:1 by volume mixture of ethyl acetate and hexane. The product was recrystallized from a mixture of methylene chloride and hexane, to give 433 mg of the title compound as colorless plates melting at 154°–156° C.

Elemental Analysis: Calculated for $C_{19}H_{19}NO_3$: C, 73.77%; H, 6.19%; N, 4.53%. Found: C, 73.64%; H, 6.16%; N, 4.53%.

Infrared Absorption Spectrum (KBr) $\nu_{max} cm^{-1}$: 1730, 1665.

Nuclear Magnetic Resonance Spectrum (CDCl$_3$) δ ppm: 3.80 (3H, singlet); 6.13 (1H, triplet, J=3 Hz); 8.03 (1H, doublet, J=8 Hz).

Mass Spectrum (m/e): 309 (M+).

EXAMPLE 2

Methyl 1,2,2aβ,3β,11,11aβ,11bβ,11cα-octahydro-10-oxo-10H-cyclopenta[d,e]indolo[3,2,1-i,j]quinoline-3α-carboxylate (Compound No. 12)

6.19 g of methyl (Z)-3-[1-(2-cyclopenten-1-yl)acetyl-1H-indol-3-yl]acrylate (prepared following the procedure described in Preparation 1, but employing the Z-isomer of the acrylate starting material) were added to 50 ml of mesitylene and the mixture was heated under reflux for 17 hours. The crystalline substance which separated from the reaction mixture was collected by filtration and recrystallized from a mixture of methylene chloride and hexane, to give 4.00 g of the title compound as colorless needles melting at 186°–188° C.

Elemental Analysis: Calculated for $C_{19}H_{19}NO_3$: C, 73.77%; H, 6.19%; N, 4.53%. Found: C, 73.83%; H, 6.27%; N, 4.55%.

Infrared Absorption Spectrum (KBr) $\nu_{max} cm^{-1}$: 1730, 1660.

Nuclear Magnetic Resonance Spectrum (CDCl$_3$) δ ppm: 3.70 (3H, singlet); 5.87 (1H, quartet, J=3 Hz); 8.03 (1H, doublet, J=8 Hz).

Mass Spectrum (m/e): 309 (M+).

Compounds No. 2–11 and 13 as shown in Table 1, 27 as shown in Table 2 and 29–33 as shown in Table 3 were prepared by the same procedures as described in Examples 1 and 2.
Compound No. 2, melting at 177°–179° C.
Compound No. 3, melting at 188.5°–190.5° C.
Compound No. 4, melting at 218°–220° C.
Compound No. 5, melting at 184°–186° C.
Compound No. 6, melting at 198°–202° C.
Compound No. 7, melting at 209°–210° C.
Compound No. 8, melting at 139°–141° C.
Compound No. 9, melting at 111°–113° C.
Compound No. 10, melting at 141°–143° C.
Compound No. 11, melting at 129°–131° C.
Compound No. 13, melting at 157°–159° C.
Compound No. 27, melting at 153.5°–160.5° C.
Compound No. 29, melting at 190°–191° C.
Compound No. 30, melting at 172°–175° C.
Compound No. 31, melting at 143°–145° C.
Compound No. 32, melting at 120°–122° C.
Compound No. 33, melting at 154°–156° C.

EXAMPLE 3

1,2,2aβ,3α,11,11aβ,11bβ,11cα-Octahydro-10-oxo-10H-cyclopenta[d,e]indolo[3,2,1-i,j]quinoline-3α-carboxylic acid (Compound No. 14)

1.547 g of methyl 1,2,2aβ,3α,11,11aβ,11bβ,11cα-octahydro-10-oxo-10H-cyclopenta[d,e]indolo[3,2,1-i,j]quinoline-3β-carboxylate (prepared as described in Example 1) was added to 16 ml of methanol, and a solution of 0.34 g of potassium hydroxide in 4 ml of water was subsequently added to the resulting mixture. The mixture was then heated under reflux for 30 minutes. At the end of this time, the reaction mixture was poured into ice-water and acidified by the addition of hydrochloric acid. The crystalline substance which separated was collected by filtration, washed and recrystallized from 70% v/v aqueous ethanol, to give 0.951 g of the title compound as colorless scales melting at 214°–216° C. (with decomposition).

Elemental Analysis: Calculated for $C_{18}H_{17}NO_3$: C, 73.20%; H, 5.80%; N, 4.74%. Found: C, 73.25%; H, 5.81%; N, 4.71%.

Infrared Absorption Spectrum (KBr) $\nu_{max}$cm$^{-1}$: 1700, 1665.

Nuclear Magnetic Resonance Spectrum (CDCl$_3$) δ ppm: 6.23 (1H, triplet, J=3 Hz); 7.9 (1H, doublet, J=8 Hz).

Mass Spectrum (m/e): 295 (M+).

Compounds No. 15–23 as shown in Table 1, No. 28 as shown in Table 2, No. 34 as shown in Table 3, No. 44 as shown in Table 4 and No. 73–78 and 171–182 as shown in Table 5 were prepared by the same procedures as described in Example 3.

Compound No. 15, melting at 221°–223° C.
Compound No. 16, melting at 226°–228° C.
Compound No. 17 hemihydrate, melting at 190°–192° C. (with decomposition)
Compound No. 18, melting at 264°–265° C. (with decomposition)
Compound No. 19, melting at 200°–203° C.
Compound No. 20, melting at 240°–243° C.
Compound No. 21, melting at 250°–253° C.
Compound No. 22, melting at 206.5°–208.5° C.
Compound No. 23, melting at 214°–216° C. (with decomposition)
Compound No. 28, melting at 235°–236° C.
Compound No. 34, melting at 199°–201° C.
Compound No. 44, melting at 176°–178° C. (with decomposition)
Compound No. 73, melting at 222°–227° C.
Compound No. 74, melting at 238°–246° C.
Compound No. 75, melting at 213°–220° C.
Compound No. 76, melting at 130°–150° C. (with decomposition)
Compound No. 77, melting at 225°–227° C. (with decomposition)
Compound No. 78, melting at 188.5°–191° C.
Compound No. 171, melting at 240°–248° C.
Compound No. 172, melting at 240°–242° C.
Compound No. 173, melting at 272°–275° C. (with decomposition)
Compound No. 174, melting at 240°–243° C.
Compound No. 175, melting at 235°–240° C. (with decomposition)
Compound No. 176, melting at 241°–243° C. (with decomposition)
Compound No. 177, melting at 279°–281° C. (with decomposition)
Compound No. 178, melting at 288°–289° C. (with decomposition)
Compound No. 179, melting at 115°–120° C.
Compound No. 180, melting at 250°–253° C.
Compound No. 181, melting at 238°–240° C. (with decomposition)
Compound No. 182, melting at 260°–268° C.

EXAMPLE 4

2-Bromoethyl 1,2,2aβ,3α,11,11aβ,11bβ,11cα-octahydro-10-oxo-10H-cyclopenta[d,e]indolo[3,2,1-i,j]quinoline-3β-carboxylate (Compound No. 24)

To 100 ml of dioxane were added 2.953 g of 1,2,2aβ,3α,11,11aβ,11bβ,11cα-octahydro-10-oxo-10H-cyclopenta[d,e]indolo[3,2,1-i,j]quinoline-3β-carboxylic acid (prepared as described in Example 3), 2.27 g of dicyclohexylcarbodiimide, 122 mg of 4-(dimethylamino)pyridine and 1.4 g of 2-bromoethanol. The mixture was stirred at ambient temperature for 8 hours and then allowed to stand overnight. The insolubles which had separated were removed by filtration, and the filtrate was condensed by evaporation under reduced pressure. The residue was purified by silica gel column chromatography, using a 3:7 by volume mixture of ethyl acetate and hexane as eluent, and the product was recrystallized from a mixture of ethyl acetate and diisopropyl ether, to give 1.55 g of the title compound as colorless needles melting at 136.5°–138.5° C.

Elemental Analysis: Calculated for $C_{20}H_{20}BrNO_3$: C, 59.71%; H, 5.01%; N, 3.48%. Found: C, 59.91%; H, 5.22%; N, 3.49%.

Infrared Absorption Spectrum (KBr) $\nu_{max}$cm$^{-1}$: 1735, 1665.

Nuclear Magnetic Resonance Spectrum (CDCl$_3$) δ ppm: 3.57 (2H, triplet, J=6 Hz); 4.52 (2H, triplet, J=6 Hz); 6.20 (1H, triplet, J=3 Hz); 8.08 (1H, doublet, J=8 Hz).

Mass Spectrum (m/e): 401 (M+).

EXAMPLE 5

2-(1-Pyrrolidinyl)ethyl 1,2,2aβ,3α,11,11aβ,11bβ,11cα-octahydro-10-oxo-10H-cyclopenta[d,e]indolo[3,2,1-i,j]quinoline-3β-carboxylate (Compound No. 232)

To 20 ml of toluene were added 0.805 g of 2-bromoethyl 1,2,2aβ,3α,11,11aβ,11bβ,11cα-octahydro-10-oxo-10H-cyclopenta[d,e]indolo[3,2,1-i,j]quinoline-3β-carboxylate (prepared as described in Example 4) and 0.43 g of pyrrolidine, and the mixture was heated under reflux for 5 hours. The reaction mixture was then washed first with a saturated aqueous solution of sodium hydrogen carbonate and then with water, after which it was dried over anhydrous magnesium sulfate. The mixture was then condensed by evaporation under reduced pressure. The residue was purified by silica gel column chromatography, using ethyl acetate as eluent, and the product was recrystallized from a mixture of ethyl acetate and hexane, to give 0.339 g of the title compound as colorless powdery crystals melting at 130°–132° C.

Elemental Analysis: Calculated for $C_{24}H_{28}N_2O_3$: C, 73.44%; H, 7.19%; N, 7.14%. Found: C, 73.36%; H, 7.13%; N, 7.18%.

Infrared Absorption Spectrum (KBr) $\nu_{max}$cm$^{-1}$: 1730, 1710, 1665.

Nuclear Magnetic Resonance Spectrum (CDCl$_3$) δ ppm: 2.78 (2H, triplet, J=6 Hz); 4.34 (2H, triplet, J=6 Hz); 6.17 (1H, triplet, J=3 Hz); 8.08 (1H, doublet, J=8 Hz).

Mass Spectrum (m/e): 392 (M+).

Compounds No. 233–237 as shown in Table 7 were prepared by the same procedures as described in Example 5.

Compound No. 233, melting at 119°–121° C.
Compound No. 234 maleate, melting at 170°–172° C. (with decomposition)

Compound No. 235, melting at 111°–115° C.
Compound No. 236 maleate, melting at 140°–143° C. (with decomposition)
Compound No. 237 maleate, melting at 168°–170° C. (with decomposition)

EXAMPLE 6

3β-Benzyloxycarbonylamino-1,2,2aβ,3α,11,-11aβ,11bβ,11cα-octahydro-11-cα-methylcyclopenta-[d,e]indolo[3,2,1-i,j]quinolin-10-one (Compound No. 25)

To a suspension of 3 g of 1,2,2aβ,3α,11,11aβ,11bβ,1-1cα-octahydro-11cα-methyl-10-oxo-10H-cyclopenta[d,e]indolo[3,2,1-i,j]quinoline-3β-carboxylic acid (Compound No. 19, prepared following the procedure described in Example 3) in 20 ml of methylene chloride were added 2 ml of oxalyl chloride, and the mixture was heated under reflux for 1 hour. The reaction mixture was then condensed by evaporation under reduced pressure, and the residue was dissolved in 50 ml of methylene chloride. The resulting solution was added, whilst ice-cooling, to a solution of 3 g of sodium azide in 20 ml of water, and the mixture was stirred for 30 minutes. The organic layer was separated, dried over anhydrous magnesium sulfate, and condensed by evaporation under reduced pressure. The residue was dissolved in 20 ml of dioxane and heated under reflux for 1 hour; 4 ml of benzyl alcohol were added thereto, and the reflux heating was continued for a further 10 hours. The reaction mixture was then condensed by evaporation under reduced pressure, and the residue was purified by silica gel column chromatography, using a 1:3 by volume mixture of ethyl acetate and hexane as eluent. The product was then recrystallized from a mixture of methylene chloride and hexane, to give 2.5 g of the title compound as colorless prisms melting at 187°–189° C.

Elemental Analysis: Calculated for $C_{26}H_{26}N_2O_3$: C, 75.34%; H, 6.32%; N, 6.76%. Found: C, 74.97%; H, 6.35%; N, 6.64%.

Infrared Absorption Spectrum (KBr) $v_{max}cm^{-1}$: 3320, 1720, 1640.

Nuclear Magnetic Resonance Spectrum (perdeuterated dimethylformamide) δ ppm: 1.32 (3H, singlet); 5.15 (2H, singlet); 5.85 (1H, doublet, J=2 Hz); 7.98 (1H, doublet, J=8 Hz).

Mass Spectrum (m/e): 414 (M+).

EXAMPLE 7

3β-Amino-1,2,2aβ,3α,11,11aβ,11bβ,11cα-octahydro-11cα-methylcyclopenta[d,e]indolo[3,2,1-i,j]quinolin-10-one hydrochloride (hydrochloride of Compound No. 26)

A solution of 2 g of 3β-benzyloxycarbonylamino-1,2,2aβ,3α,11,11aβ,11bβ,11cα-octahydro-11cα-methylcyclopenta[d,e]indolo[3,2,1-i,j]quinolin-10-one (prepared as described in Example 6) and 10 ml of thioanisole in 50 ml of trifluoroacetic acid was stirred at ambient temperature for 4 hours. The reaction mixture was then condensed by evaporation under reduced pressure, and the residue was dissolved in methanol. Methanolic hydrogen chloride was added to this solution, and the resulting mixture was condensed by evaporation under reduced pressure. The residue was recrystallized from a mixture of methanol and acetone, to give 1.2 g of the title compound as yellow needles melting at 275° C. (with decomposition).

Elemental Analysis: Calculated for $C_{18}H_{20}N_2O.HCl$: C, 68.24%; H, 6.68%; N, 8.84%; Cl, 11.19%. Found: C, 67.89%; H, 6.77%; N, 8.70%; Cl, 11.09%.

Infrared Absorption Spectrum (KBr) $v_{max}cm^{-1}$: 1630.

Nuclear Magnetic Resonance Spectrum (perdeuterated dimethylformamide) δ ppm: 1.35 (3H, singlet); 6.14 (1H, doublet, J=2 Hz); 7.95 (1H, doublet, J=8 Hz).

EXAMPLE 8

Methyl 1,2,2aβ,3α,4,11,11aβ,11bβ-octahydro-10-oxo-10H-cyclopenta[d,e]indolo[3,2,1-i,j]quinoline-3β-carboxylate (Compound No. 35)

To a solution of 0.2 g of methyl 1,2,2aβ,3α,11,-11aβ,11bβ,11cα-octahydro-10-oxo-10H-cyclopenta[d,e]indolo[3,2,1-i,j]quinoline-3β-carboxylate (prepared as described in Example 1) in 10 ml of dioxane was added 0.5 ml of 15% w/w ethanolic hydrogen chloride, and the mixture was heated under reflux for 30 minutes. The reaction mixture was then condensed by evaporation under reduced pressure, and the residue was recrystallized from diisopropyl ether, to give 0.152 g of the title compound as colorless prisms melting at 124°–126° C.

Elemental Analysis: Calculated for $C_{19}H_{19}NO_3$: C, 73.77%; H, 6.19%; N, 4.53%. Found: C, 73.74%; H, 5.90%; N, 4.45%.

Infrared Absorption Spectrum (KBr) $v_{max}cm^{-1}$: 1740, 1700.

Nuclear Magnetic Resonance Spectrum (CDCl₃) δ ppm: 3.73 (3H, singlet); 8.3–8.5 (1H, multiplet).

Mass Spectrum (m/e): 309 (M+).

Compounds No. 36–39 and 41–43 as shown in Table 4 and No. 69–72 as shown in Table 8 were prepared by the same procedures as described in Example 8.

Compound No. 36, melting at 110°–112° C.
Compound No. 37, melting at 117°–120° C.
Compound No. 38, melting at 122°–129° C.
Compound No. 39, melting at 127°–129° C.
Compound No. 41, melting at 91°–92° C.
Compound No. 42, melting at 116°–120° C.
Compound No. 43, melting at 122°–123.5° C.
Compound No. 69, melting at 140°–141° C.
Compound No. 70, melting at 125°–127° C.
Compound No. 71, melting at 111°–113° C.
Compound No. 72, melting at 137°–140° C.

EXAMPLE 9

Methyl 1,2,3,3aβ,4α,5,11,12,12aβ,12bβ-decahydro-11-oxobenzo[d,e]indolo[3,2,1-i,j]quinoline-4-carboxylate (Compound No. 67)

A mixture of 56.4 g of methyl (E)-3-[1-(2-cyclohexen-1-yl)acetyl-1H-indol-3-yl]acrylate (prepared as described in Preparation 2) and 200 ml of mesitylene was heated under reflux for 24 hours. The reaction mixture was then condensed by evaporation under reduced pressure, and the residue was purified by silica gel column chromatography using methylene chloride as eluent. The product was recrystallized from a mixture of dioxane and hexane, to give 40.15 g of the title compound as colorless prisms melting at 156°–158° C.

Elemental Analysis: Calculated for $C_{20}H_{21}NO_3$: C, 74.28%; H, 6.55%; N, 4.33%. Found: C, 74.27%; H, 6.52%; N, 4.37%.

Infrared Absorption Spectrum (KBr) $\nu_{max}cm^{-1}$: 1735, 1700.

Nuclear Magnetic Resonance Spectrum (CDCl$_3$) δ ppm: 3.70 (3H, singlet); 8.3–8.5 (1H, multiplet).

Mass Spectrum (m/e): 323 (M+).

Compounds No. 40 as shown in Table 4, No. 66 and 68 as shown in Table 5 and No. 222 and 223 as shown in Table 6 were prepared by the same procedure as described in Example 9.

Compound No. 40, melting at 91°–93° C.
Compound No. 66, melting at 124°–126° C.
Compound No. 68, melting at 143°–144° C.
Compound No. 222, melting at 160°–161° C.
Compound No. 223, melting at 194°–196° C.

EXAMPLE 10

11aβ-Ethyl-1,2,2aβ,3α,4,11,11aβ,11bβ-octahydro-10-oxo-10H-cyclopenta[d,e]indolo[3,2,1-i,j]quinoline-3β-carboxylic acid (Compound No. 46)

To a solution of 7.11 g of 11aβ-ethyl-1,2,2aβ,3α,11,-11aβ,11bβ,11cα-octahydro-10-oxo-10H̲-cyclopenta[d-,e]indolo[3,2,1-i,j]quinoline-3β-carboxylic acid (Compound No. 30, prepared following the procedure described in Example 3) in 100 ml of dioxane was added 1 ml of 15% w/w ethanolic hydrogen chloride, and the mixture was heated under reflux for 30 minutes. The reaction mixture was then condensed by evaporation under reduced pressure, and the residue was recrystallized from a mixture of ethanol and diisopropyl ether, to give 6.78 g of the title compound as colorless needles melting at 216°–217° C.

Elemental Analysis: Calculated for $C_{20}H_{21}NO_3$: C, 74.28%; H, 6.55%; N, 4.33%. Found: C, 73.93%; H, 6.53%; N, 4.29%.

Infrared Absorption Spectrum (KBr) $\nu_{max}cm^{-1}$: 1690.

Nuclear Magnetic Resonance Spectrum (CDCl$_3$) δ ppm: 8.15–8.40 (1H, multiplet).

Mass Spectrum (m/e): 323 (M+).

Compound No. 45 as shown in Table 4 was prepared by the same procedure as described in Example 10.
Compound No. 45, melting at 212°–215° C.

EXAMPLE 11

2,3,3aβ,4α,5,12,12aβ,12bβ-Octahydro-4β-dimethylaminocarbonylbenzo[d,e]indolo[3,2,1-i,j]quinolin-11(1H)-one (Compound No. 79)

To a solution of 0.5 g of 1,2,3,3aβ,4α,5,11,12,-12aβ,12bβ-decahydro-11-oxobenzo[d,e]indolo[3,2,1-i,j]quinoline-4β-carboxylic acid (Compound No. 29—prepared following the procedure described in Examples 1 and 2) in 10 ml of methylene chloride was added 1 ml of oxalyl chloride, and the mixture was allowed to stand overnight, after which it was condensed by evaporation under reduced pressure. The residue was dissolved in benzene, and then a solution of dimethylamine in benzene was added thereto. The mixture was allowed to stand overnight, after which it was condensed by evaporation under reduced pressure. The resulting residue was recrystallized from ethyl acetate, to give 0.3 g of the title compound as colorless needles melting at 188°–190° C.

Elemental Analysis: Calculated for $C_{21}H_{24}N_2O_2$: C, 74.97%; H, 7.19%; N, 8.33%. Found: C, 74.90%; H, 7.18%; N, 8.31%.

Nuclear Magnetic Resonance Spectrum [(CD$_3$)$_2$SO] δ ppm: 3.30 (6H, singlet); 8.1–8.4 (1H, multiplet).

Mass Spectrum (m/e): 336 (M+).

Compounds No. 80 and 81 as shown in Table 5 were prepared by the same procedures as described in Example 11.

Compound No. 80, melting at 230° C.
Compound No. 81, melting at 275°–277° C.

EXAMPLE 12

2,3,3aβ,4α,5,12,12aβ,12bβ-Octahydro-4β-(1-pyrrolidinyl)carbonylbenzo[d,e]indolo[3,2,1-i,j]quinolin-11(1H)-one (Compound No. 82)

A solution of 0.9 g of 1,2,3,3aβ,4α,5,11,12,12aβ,12bβ-decahydro-11-oxobenzo[d,e]indolo[3,2,1-i,j]quinoline-4β-carboxylic acid (Compound No. 29—prepared following the procedures described in Examples 1 and 2), 0.6 g of diethyl phosphorocyanidate, 0.4 g of triethylamine and 0.22 g of pyrrolidine in 50 ml of N,N-dimethylformamide was allowed to stand overnight. The reaction mixture was then poured into ice-water and extracted with methylene chloride. The extract was then dried over anhydrous magnesium sulfate. The solvent was removed from the extract by evaporation under reduced pressure. The residue was washed with diethyl ether and then recrystallized from a mixture of ethyl acetate and acetone, to give 0.4 g of the title compound as colorless prisms melting at 195°–198° C.

Elemental Analysis: Calculated for $C_{23}H_{26}N_2O_2$: C, 76.21%; H, 7.23%; N, 7.73%. Found: C, 76.07%; H, 7.19%; N, 7.68%.

Nuclear Magnetic Resonance Spectrum [(CD$_3$)$_2$SO] δ ppm: 8.15–8.45 (1H, multiplet).

Mass Spectrum (m/e): 362 (M+).

Compounds No. 83 and 84 as shown in Table 5 and No. 240 were prepared by the same procedures as described in Example 12.

Compound No. 83 hydrochloride, melting at 200° C. (with decomposition)
Compound No. 84, melting at 205° C.
Compound No. 247 hemihydrate, melting at 145°–155° C.

EXAMPLE 13

2-Bromoethyl 1,2,2aβ,3α,4,11,11aβ,11bβ-octahydro-10-oxo-10H-cyclopenta[d,e]indolo[3,2,1-i,j]quinoline-3β-carboxylate (Compound No. 85)

A solution of 21.86 g of 1,2,2aβ,3α,4,11,11aβ,11bβ-octahydro-10-oxo-10H̲-cyclopenta[d,e]indolo[3,2,1-i,j]quinoline-3β-carboxylic acid (Compound No. 45—prepared following the procedures described in Example 10), 16.79 g of dicyclohexylcarbodiimide, 0.9 g of 4-dimethylaminopyridine and 10.17 g of 2-bromoethanol in 100 ml of dioxane was stirred at ambient temperature for 8 hours and then allowed to stand overnight. The insolubles which had separated were removed by filtration, and the filtrate was condensed by evaporation under reduced pressure. The residue was purified by silica gel column chromatography, using a 3:7 by volume mixture of ethyl acetate and hexane as eluent, and the product was recrystallized from diisopropyl ether, to give 14 g of the title compound as pale yellow prisms melting at 89°–91° C.

Elemental Analysis: Calculated for $C_{20}H_{20}BrNO_3$: C, 59.71%; H, 5.01%; N, 3.48%; Br, 19.86%. Found: C, 60.05%; H, 5.10%; N, 3.52%; Br, 19.83%.

Infrared Absorption Spectrum (KBr) $\nu_{max}cm^{-1}$: 1720, 1700.

Nuclear Magnetic Resonance Spectrum (CDCl$_3$) δ ppm: 8.25–8.50 (1H, multiplet).

EXAMPLE 14

2-(1-Pyrrolidinyl)ethyl 1,2,2aβ,3α,4,11,11aβ,11bβ-octahydro-10-oxo-10H-cyclopenta[d,e]indolo[3,2,1-i,j]quinoline-3β-carboxylate (Compound No. 238)

A solution of 0.805 g of 2-bromoethyl 1,2,2aβ,3α,4,11,11aβ,11bβ-octahydro-10-oxo-10H-cyclopenta[d,e]indolo[3,2,1-i,j]quinoline-3β-carboxylate (prepared as described in Example 13) and 0.43 g of pyrrolidine in 20 ml of toluene was heated under reflux for 4 hours. The reaction mixture was then washed first with a saturated aqueous solution of sodium hydrogen carbonate and then with water, and was then dried over anhydrous magnesium sulfate. The solvent was then removed by evaporation under reduced pressure. The residue was purified by silica gel column chromatography, eluted with a 1:9 by volume mixture of ethanol and ethyl acetate, to give 0.579 g of the title compound as a colorless oily substance.

Elemental Analysis: Calculated for $C_{24}H_{28}N_2O_3$: C, 73.44%; H, 7.19%; N, 7.14%. Found: C, 72.90%; H, 7.23%; N, 6.94%.

Infrared Absorption Spectrum (KBr) $\nu_{max}cm^{-1}$: 1730, 1700.

Nuclear Magnetic Resonance Spectrum (CDCl$_3$) δ ppm: 2.72 (2H, triplet, J=6 Hz); 4.27 (2H, triplet, J=6 Hz); 8.3–8.5 (1H, multiplet).

Mass Spectrum (m/e): 392 (M+).

Compounds No. 210 as shown in Table 5 and No. 239–243 as shown in Table 8 were prepared by the same procedures as described in Example 14.

Compound No. 210, a pale brown amorphous substance
Compound No. 239, melting at 74.5°–76.5° C.
Compound No. 240, melting at 58°–62° C.
Compound No. 241, melting at 123.5°–126.5° C.
Compound No. 242, a pale yellow oil
Compound No. 243, a pale yellow oil.

EXAMPLE 15

3β-Benzyloxycarbonylamino-1,2,2aβ,3α,4,11,11aβ,11bβ-octahydrocyclopenta[d,e]indolo]3,2,1-i,j]quinolin-10-one (Compound No. 47)

To a suspension of 1.477 g of 1,2,2aβ,3α,11,11aβ,11bβ,11cα-octahydro-10-oxo-10H-cyclopenta[d,e]indolo[3,2,1-i,j]quinoline-3β-carboxylic acid (prepared as described in Example 3) in 20 ml of methylene chloride was added 0.53 ml of oxalyl chloride, and the mixture was heated under reflux for 30 minutes. The reaction mixture was then condensed by evaporation under reduced pressure, and the residue was dissolved in 20 ml of acetone. A solution of 0.49 g of sodium azide in 5 ml of water was added, whilst ice-cooling, to the resulting solution, and the mixture was stirred for 30 minutes. The reaction mixture was then poured into water and extracted with methylene chloride. The extract was dried over anhydrous magnesium sulfate, and the solvent was removed by evaporation under reduced pressure. The residue was dissolved in 20 ml of dioxane and, after heating the solution under reflux for 30 minutes, 2 ml of benzyl alcohol were added thereto and the reflux heating was continued for a further 2 hours. The reaction mixture was then condensed by evaporation under reduced pressure. The residue was purified by silica gel column chromatography using a 1:2 by volume mixture of ethyl acetate and hexane as eluent, and the product was recrystallized from a mixture of ethyl acetate and hexane, to afford 0.983 g of the title compound as colorless needles melting at 172°–173° C.

Elemental Analysis: Calculated for $C_{25}H_{24}N_2O_3$: C, 74.98%; H, 6.04%; N, 7.00%. Found: C, 75.04%; H, 5.84%; N, 6.85%.

Infrared Absorption Spectrum (KBr) $\nu_{max}cm^{-1}$: 3220, 1705, 1690.

Nuclear Magnetic Resonance Spectrum (CDCl$_3$) δ ppm: 5.13 (2H, singlet); 8.2–8.45 (1H, multiplet).

Mass Spectrum (m/e): 400 (M+).

Compounds No. 48–54 as shown in Table 4, No. 86–93 as shown in Table 5 and No. 224–227 as shown in Table 6 were prepared by the same procedures as described in Example 15.

Compound No. 48, melting at 192°–194° C. (with decomposition)
Compound No. 49, melting at 187°–188° C.
Compound No. 50, melting at 159.5°–162.5° C.
Compound No. 51, melting at 152°–153° C.
Compound No. 52, melting at 167°–168° C.
Compound No. 53, melting at 120°–122° C.
Compound No. 54, melting at 207°–208° C.
Compound No. 86, melting at 170°–173° C.
Compound No. 87, melting at 248°–249° C.
Compound No. 88, melting at 165°–168° C.
Compound No. 89, melting at 178°–179° C.
Compound No. 90, melting at 184°–186° C.
Compound No. 91, melting at 136°–139° C.
Compound No. 92, melting at 209°–211° C.
Compound No. 93, melting at 213°–217° C. (with decomposition)
Compound No. 224, melting at 199°–200° C.
Compound No. 225, melting at 224°–225° C.
Compound No. 226, melting at 217°–218° C.

Compound No. 227, melting at 251°–252° C.

EXAMPLE 16

2,3,3aβ,4α,5,12,12aβ,12bβ-Octahydro-4β-[4-(m-tolyl)-1-piperazinyl]carbonylaminobenzo[d,e]indolo[3,2,1-i,j]quinolin-11-(1H)-one (Compound No. 94)

To a suspension of 3.094 g of 1,2,3,3aβ,4α,5,11,12,-12aβ,12bβ-decahydro-11-oxobenzo[d,e]indolo[3,2,1-i,j]quinoline-4β-carboxylic acid (Compound No. 29—prepared following the procedures described in Examples 1 and 2) in 100 ml of methylene chloride was added 1.3 ml of oxalyl chloride, and the mixture was heated under reflux for 30 minutes. The reaction mixture was then condensed by evaporation under reduced pressure, and the resulting residue was dissolved in 50 ml of acetone. A solution of 0.98 g of sodium azide in 10 ml of water was then added to the solution thus obtained, whilst ice-cooling, and the mixture was stirred for 30 minutes. The reaction mixture was then poured into water and extracted with methylene chloride. The extract was dried over anhydrous magnesium sulfate and the solvent was removed by evaporation under reduced pressure. The residue was dissolved in 50 ml of dioxane and, after heating the solution under reflux for 30 minutes, 2.12 g of 1-(m-tolyl)piperazine were added thereto and the reflux heating was continued for a further 2 hours. The reaction mixture was then condensed by evaporation under reduced pressure, and the residue was crystallized by adding a small amount of ethyl acetate. The resulting crystalline substance was separated by filtration and recrystallized from a mixture of N,N-dimethylformamide and diethyl ether, to give 1.73 g of the title compound as a colorless crystalline powder melting at 249°–251° C. (with decomposition).

Elemental Analysis: Calculated for $C_{30}H_{34}N_4O_2$: C, 74.66%; H, 7.10%; N, 11.61%. Found: C, 74.36%; H, 7.12%; N, 11.71%.

Infrared Absorption Spectrum (KBr) $\nu_{max}$cm$^{-1}$: 3400, 1685, 1640.

Nuclear Magnetic Resonance Spectrum (CF$_3$COOD) δ ppm: 8.25–8.45 (1H, multiplet).

Mass Spectrum (m/e): 482 (M+).

EXAMPLE 17

3β-Amino-1,2,2aβ,3α,4,11,11aβ,11bβ-octahydrocyclopenta[d,e]indolo[3,2,1-i,j]quinolin-10-one maleate (maleate of Compound No. 55)

A solution of 10 g of 3β-benzyloxycarbonylamino-1,2,2aβ,3α,4,11,11aβ,11bβ-octahydrocylopenta[d,e]indolo[3,2,1-i,j]quinolin-10-one (prepared as described in Example 15) in 150 ml of N,N-dimethylformamide was hydrogenated by bubbling hydrogen gas through the solution in the presence of 10% w/w palladium-on-carbon. After completion of the hydrogenation reaction, the reaction mixture was filtered and the filtrate was condensed by evaporation under reduced pressure. The residue was converted to the maleate by conventional means, and the salt was recrystallized from a mixture of ethanol and ethyl acetate, to give 7.22 g of the title compound as colorless scaly crystals melting at 197°–198° C. (with decomposition).

Elemental Analysis: Calculated for $C_{21}H_{22}N_2O_5$: C, 65.96%; H, 5.80%; N, 7.33%. Found: C, 65.79%; H, 5.72%; N, 7.12%.

Infrared Absorption Spectrum (KBr) $\nu_{max}$cm$^{-1}$: 3430, 1700.

Nuclear Magnetic Resonance Spectrum [(CD$_3$)$_2$SO] δ ppm: 8.15–8.40 (1H, multiplet).

Mass Spectrum (m/e): 266 (M+).

Compounds No. 56–61 as shown in Table 4, No. 95–99, 106 and 108–110 as shown in Table 5 and No. 228–231 as shown in Table 6 were prepared by the same procedures as described in Example 17.

Compound No. 56 maleate, melting at 195° C. (with decomposition)
Compound No. 57 maleate, melting at 202° C. (with decomposition)
Compound No. 58 maleate, melting at 197° C. (with decomposition)
Compound No. 59 maleate, melting at 195° C. (with decomposition)
Compound No. 60 maleate, melting at 205° C. (with decomposition)
Compound No. 61, melting at 184° C. (with decomposition)
Compound No. 95 maleate, melting at 212°–213° C.
Compound No. 96 maleate, melting at 221°–222° C.
Compound No. 97, melting at 170°–172° C.
Compound No. 98 maleate, melting at 216°–217° C. (with decomposition)
Compound No. 99 maleate, melting at 221°–222° C.
Compound No. 106 maleate, melting at 221°–222° C. (with decomposition)
Compound No. 108, melting at 177.5°–179.5° C.
Compound No. 109 maleate, melting at 228° C. (with decomposition)
Compound No. 110 maleate, melting at 216°–216.5° C. (with decomposition)
Compound No. 228 maleate, melting at 221° C. (with decomposition)
Compound No. 229 maleate, melting at 216° C. (with decomposition)
Compound No. 230 maleate, melting at 239° C. (with decomposition)
Compound No. 231 maleate, melting at 214°–215° C. (with decomposition).

EXAMPLE 18

1,2,2aβ,3α,4,11,11aβ,11bβ-Octahydro-3β-propylaminocyclopenta[d,e]indolo[3,2,1-i,j]quinolin-10-one maleate (maleate of Compound No. 62)

The free base isolated by conventional means from 1.912 g of 3β-amino-1,2,2aβ,3α,4,11,11aβ,11bβ-octahydrocyclopenta[d,e]indolo[3,2,1-i,j]quinolin-10-one maleate (prepared as described in Example 17) was dissolved in 20 ml of benzene, and 3.4 g of propyl iodide and 5 ml of a saturated aqueous solution of sodium hydrogen carbonate were added thereto. The mixture was then heated under reflux for 72 hours. Ethyl acetate was then added to the reaction mixture, and the organic layer was washed with water and dried over anhydrous magnesium sulfate. The solvent was then removed by evaporation under reduced pressure. The residue was purified by silica gel column chromatography, using a 9:1 by volume mixture of methylene chloride and ethanol as eluent. The product was converted into the maleate by conventional means, and this was recrystallized from a mixture of ethanol and diisopropyl ether, to give 1.206 g of the title compound as a colorless crystalline powder melting at 155°–157° C.

Elemental Analysis: Calculated for $C_{24}H_{28}N_2O_5$: C, 67.91%; H, 6.65%; N, 6.60%. Found: C, 67.66%; H, 6.60%; N, 6.63%.

Infrared Absorption Spectrum (KBr) $\nu_{max}cm^{-1}$: 1710.

Nuclear Magnetic Resonance Spectrum [$(CD_3)_2SO$] $\delta$ ppm: 8.15–8.40 (1H, multiplet).

Mass Spectrum (m/e): 308 (M+).

Compounds No. 63 and 64 as shown in Table 4 were prepared by the same procedures as described in Example 18.

Compound No. 63, melting at 167.5°–169.5° C.

Compound No. 64 maleate, melting at 218°–220° C. (with decomposition).

EXAMPLE 19

1,2,2aβ,3α,4,11,11aβ,11bβ-Octahydro-3β-dimethylaminocyclopenta[d,e]indolo[3,2,1-i,j]quinolin-10-one maleate (maleate of Compound No. 65)

To the free base isolated by conventional means from 1.912 g of 3β-amino-1,2,2aβ,3α,4,11,11aβ,11bβ-octahydrocyclopenta[d,e]indolo[3,2,1-i,j]quinolin-10-one maleate (prepared as described in Example 17) were added 1.6 g of formic acid and 1.2 g of formalin, and the mixture was heated under reflux for 2 hours. The reaction mixture was then poured onto ice-water, neutralized with sodium hydrogen carbonate and extracted with methylene chloride. The extract was dried over anhydrous magnesium sulfate, and the solvent was removed by evaporation under reduced pressure. The residue was converted into the maleate by conventional means, and this was recrystallized from a mixture of ethanol and ethyl acetate, to give 0.864 g of the title compound as a colorless crystalline powder melting at 194°–196° C. (with decomposition).

Elemental Analysis: Calculated for $C_{23}H_{26}N_2O_5$: C, 67.96%; H, 6.45%, N, 6.89%. Found: C, 67.23%; H, 6.45%; N, 6.80%. Infrared Absorption Spectrum (KBr) $\nu_{max}cm^{-1}$: 1700.

Nuclear Magnetic Resonance Spectrum [$(CD_3)_2SO$] $\delta$ ppm: 2.91 (6H, singlet); 8.20–8.40 (1H, multiplet).

Mass Spectrum (m/e): 294 (M+).

EXAMPLE 20

2,3,3aβ,4α,5,12,12aβ,12bβ-Octahydro-4β-dimethylaminobenzo[d,e]indolo[3,2,1-i,j]quinolin-11(1H)-one hydrochloride hemihydrate (hydrochloride hemihydrate of Compound No. 100)

To the free base isolated by conventional means from 1.189 g of 4β-amino-2,3,3aβ,4α,5,12,12aβ,12bβ-octahydrobenzo[d,e]indolo[3,2,1-i,j]quinolin-11(1H)-one maleate (Compound No. 106—prepared following the procedure of Example 17) were added 3 ml of formic acid and 3 ml of formalin, and the mixture was heated under reflux for 3 hours. The reaction mixture was then poured into ice-water, neutralized with sodium hydrogen carbonate and extracted with methylene chloride. The extract was dried over anhydrous magnesium sulfate, and the solvent was removed by evaporation under reduced pressure. The residue was converted into the hydrochloride by conventional means, and this (as the hemihydrate) was recrystallized from a mixture of ethanol and ethyl acetate to give 0.701 g of the title compound as a colorless crystalline powder melting at 223° C. (with decomposition).

Elemental Analysis: Calculated for $C_{20}H_{24}N_2O \cdot HCl \cdot \frac{1}{2}H_2O$: C, 67.88%; H, 7.41%; N, 7.92%; Cl, 10.02%. Found: C, 67.60%; H, 7.36%; N, 7.27%; Cl, 9.44%.

Infrared Absorption Spectrum (KBr) $\nu_{max}cm^{-1}$: 1738, 1700.

Nuclear Magnetic Resonance Spectrum [$(CD_3)_2SO$] $\delta$ ppm: 8.15–8.40 (1H, multiplet).

Mass Spectrum (m/e): 308 (M+).

Compounds No. 101–103 as shown in Table 5 were prepared by the same procedures as described in Examples 19 and 20.

Compound No. 101 tartrate, melting at 80°–95° C. (with decomposition)

Compound No. 102 hydrochloride, melting at 296°–298° C. (with decomposition)

Compound No. 103 hydrochloride, melting at 261°–263° C.

EXAMPLE 21

4β-Amino-2,3,3aβ,4α,5,12,12aβ,12bβ-octahydro-7-hydroxybenzo[d,e]indolo[3,2,1-i,j]quinolin-11(1H)-one (Compound No. 107)

A solution of 1.093 g of 7-benzyloxy-4β-benzyloxycarbonylamino-2,3,3aβ,4α,5,12,12aβ,12bβ-octahydrobenzo[d,e]indolo[3,2,1-i,j]quinolin-11(1H)-one (Compound No. 88, prepared following the procedures of Example 15) in 20 ml of N,N-dimethylformamide was hydrogenated by bubbling hydrogen through the solution in the presence of 10% w/w palladium-on-carbon. After completion of the hydrogenation reaction, the reaction mixture was filtered and the filtrate was condensed by evaporation under reduced pressure. The residue was recrystallized from ethanol to give 0.303 g of the title compound as colorless needles melting at 235°–236° C.

Elemental Analysis: Calculated for $C_{33}H_{32}N_2O_4$: C, 72.95%; H, 6.80%; N, 9.45%. Found: C, 72.90%; H, 6.76%; N, 9.44%.

Infrared Absorption Spectrum (KBr) $\nu_{max}cm^{-1}$: 3330, 3260, 1682.

Nuclear Magnetic Resonance Spectrum [$(CD_3)_2SO$] $\delta$ ppm: 8.05 (1H, doublet, J=8 Hz).

Mass Spectrum (m/e): 296 (M+).

Compounds No. 196–208 as shown in Table 5 were prepared by the same procedures as described in Example 21.

Compound No. 196, melting at 292°–294° C. (with decomposition)

Compound No. 197 hemihydrate, melting at 270°–273° C. (with decomposition)

Compound No. 198, melting at >300° C.

Compound No. 199 hemihydrate, melting at 306°–308° C. (with decomposition)

Compound No. 200, melting at 287°–290° C. (with decomposition)

Compound No. 201 hydrate, melting at 274°-275° C. (with decomposition)

Compound No. 202 hemihydrate, melting at 282°-284° C. (with decomposition)

Compound No. 203 hemihydrate, melting at 274°-276° C. (with decomposition)

Compound No. 204, melting at 288°-290° C. (with decomposition)

Compound No. 205, melting at 275°-277° C. (with decomposition)

Compound No. 206, melting at 250°-252° C. (with decomposition)

Compound No. 207 hemihydrate, melting at >300° C.

EXAMPLE 22

2,3,3aβ,4α,5,12,12aβ,12bβ-Octahydro-4β-trimethylammoniobenzo[d,e]indolo[3,2,1-i,j]quinolin-11-(1H)-one iodide (Compound No. 104)

To the free base isolated by conventional means from 2.38 g 4β-amino-2,3,3aβ,4α,5,12,12aβ,12bβ-octahydrobenzo[d,e]indolo[3,2,1-i,j]quinolin-11(1H)-one maleate (maleate of Compound No. 122—prepared following the procedures of Example 17) in 80 ml of toluene were added 17.04 g of methyl iodide and 80 ml of a saturated aqueous solution of sodium hydrogen carbonate, and the mixture was heated under reflux for 16 hours. The crystals which had separated were collected by filtration, washed with water, and recrystallized from a mixture of ethanol and water, to give 1.76 g of the title compound as colorless needles melting at 275°-277° C. (with decomposition).

Elemental Analysis: Calculated for $C_{21}H_{27}IN_2O$: C, 56.01%; H, 6.04%; N, 6.22%; I, 28.18%. Found: C, 55.85%; H, 5.85%; N, 6.04%; I, 28.21%.

Infrared Absorption Spectrum (KBr) $\nu_{max}cm^{-1}$: 1705.

Nuclear Magnetic Resonance Spectrum [$(CD_3)_2SO$] δ ppm: 8.15-8.40 (1H, multiplet).

Mass Spectrum (m/e): 308 (—$CH_3I$).

Compound No. 105 as shown in Table 2 was prepared by the same procedures as in Example 22.

Compound No. 105, melting at 266°-268° C. (with decomposition).

EXAMPLE 23

1,2,2aβ,3α,4,4a,11,11aβ,11bβ,11cα-Decahydro-10-oxo-10H-cyclopenta[d,e]indolo[3,2,1-i,j]quinoline-3β-carboxylic acid (Compound No. 244)

A solution of 2.953 g of 1,2,2aβ,3α,11,11aβ,11bβ,1-1cα-octahydro-10-oxo-10H-cyclopental[d,e]indolo[3,2,1-i,j]quinoline-3β-carboxylic acid (prepared as described in Example 3) in 50 ml of dioxane was hydrogenated by bubbling hydrogen through the solution in the presence of 0.5 g of platinum oxide. After the hydrogenation reaction was complete, the reaction mixture was filtered, and the filtrate was condensed by evaporation under reduced pressure. The residue was purified by silica gel column chromatography using a 9:1 by volume mixture of methylene chloride and ethanol as eluent, and the product was recrystallized from ethanol to give 0.782 g of the title compound as a colorless crystalline powder melting at 252°-257° C. (with decomposition).

Elemental Analysis: Calculated for $C_{18}H_{19}NO_3$: C, 72.71%; H, 6.44%; N, 4.71%; Found: C, 72.85%; H, 6.44%; N, 4.62%.

Infrared Absorption Spectrum (KBr) $\nu_{max}cm^{-1}$: 1730, 1700.

Nuclear Magnetic Resonance Spectrum [$(CD_3)_2SO$] δ ppm: 7.88 (1H, doublet, J=8 Hz).

Mass Spectrum (m/e): 297 (M+).

Compounds No. 245 and 246 as shown in Table 9 were prepared by the same procedures as described in Example 23.

Compound No. 245, melting at 173°-175° C.

Compound No. 246 hydrochloride, melting at 310° C. (with decomposition).

EXAMPLE 24

Methyl 1,2,3,3aβ,4α,5,11,12,12aβ,12bβ-decahydro-12aβ-methyl-11-oxobenzo[d,e]indolo[3,2,1-i,j]quinoline-4β-carboxylate (Compound No. 163)

A mixture of 6.1 g of methyl (E)-3-[1-(1-methyl-2-cyclohexen-1-yl)acetyl-1H-indol-3-yl]acrylate (Compound No. P-20, prepared following the procedures described in Preparation 2) and 60 ml of mesitylene was heated under reflux for 9.5 hours. To the mixture was added 0.8 ml of 15% w/v ethanolic hydrogen chloride, and the mixture was heated under reflux for 30 minutes. The reaction mixture was then condensed by evaporation under reduced pressure. The resulting residue was purified by silica gel column chromatography, using a 1:1 by volume mixture of ethyl acetate and hexane as eluent, and the product was recrystallized from diisopropyl ether, to give 5.1 g of the title compound as pale yellow prisms melting at 163°-166° C.

Elemental Analysis: Calculated for $C_{28}H_{29}NO_4$: C, 75.82%; H, 6.59%; N, 3.16%. Found: C, 75.94%; H, 6.71%; N, 3.18%.

Infrared Absorption Spectrum (KBr) $\nu_{max}cm^{-1}$: 1730, 1690.

Nuclear Magnetic Resonance Spectrum ($CDCl_3$) δ ppm: 8.17 (1H, doublet, J=9 Hz).

Mass Spectrum (m/e): 443 (M+).

Compounds No. 164-170 as shown in Table 5 were prepared by the same procedure as described in Example 24.

Compound No. 164, melting at 163°-165° C.
Compound No. 165, melting at 196°-197° C.
Compound No. 166, melting at 172°-173° C.
Compound No. 167, melting at 150°-152° C.
Compound No. 168, melting at 122°-124° C.
Compound No. 169, melting at 157°-159° C.
Compound No. 170, melting at 196°-197° C.

EXAMPLE 25

7-Benzyloxy-4β-benzyloxycarbonylamino-2,3,3aβ,-4α,5,12,12aβ,12bβ-octahydro-12aβ-phenethylbenzo[d,e]indolo[3,2,1-i,j]quinolin-11(1H)-one (Compound No. 188).

To a suspension of 7.02 of 7-benzyloxy-1,2,3,3aβ,-4α,5,11,12,12aβ,12bβ-decahydro-11-oxo-12aβ-phenethylbenzo[d,e]indolo[3,2,1-i,j]quinoline-4β-carboxylic acid (Compound No. 176—prepared following the procedures described in Example 3) in 100 ml of acetone were added 2.3 ml of triethylamine, whilst ice-cooling, and then 1.9 ml of ethyl chloroformate was added dropwise thereto, and the mixture was stirred for 30 minutes. The reaction mixture was then poured into ice-water, and extracted with methylene chloride. The extract was dried over anhydrous magnesium sulfate, and the solvent was removed by evaporation under reduced pressure. The resulting residue was dissolved in 100 ml of toluene and this solution was heated under reflux for one hour. 10 ml of benzyl alcohol were then added to the mixture, and the resulting solution was heated under reflux for 7 hours. The reaction mixture was condensed by evaporation under reduced pressure. The residue was recrystallized from dioxane, to give 6.58 g of the title compound as colorless needles melting at 177°–180° C.

Elemental Analysis: Calculated for $C_{41}H_{40}N_2O_4$ $\frac{1}{2}H_2O$: C, 77.70%; H, 6.52%; N, 4.42%. Found: C, 77.58%; H, 6.70%; N, 3.87%.

Infrared Absorption Spectrum (KBr) $\nu_{max}$cm$^{-1}$: 1730, 1695.

Nuclear Magnetic Resonance Spectrum (CDCl$_3$) $\delta$ ppm: 8.32 (1H, doublet, J=9 Hz).

Compounds No. 183–187 and 189–195 as shown in Table 5 were prepared by the same procedures as described in Example 25.

Compound No. 183, melting at 207°–208° C.
Compound No. 184, melting at 181°–183° C.
Compound No. 185, melting at 192°–194° C.
Compound No. 186, melting at 158°–159° C.
Compound No. 187, melting at 144°–147° C.
Compound No. 189, melting at 191°–193° C.
Compound No. 190, melting at 206°–207° C.
Compound No. 191, melting at 164°–172° C.
Compound No. 192, melting at 170°–175° C.
Compound No. 193, melting at 184°–186° C.
Compound No. 194, melting at 216°–217° C.
Compound No. 195, melting at 217°–218° C.

EXAMPLE 26

Allyl 7-benzyloxy-12a$\beta$-ethyl-1,2,3,3a$\beta$,4$\alpha$,5,11,12,-12a$\beta$,12b$\beta$-decahydro-11-oxobenzo[d,e]indolo[3,2,1-i,j]quinoline-4$\beta$-carboxylate (Compound No. 216)

24 g of allyl (E)-3-[5-benzyloxy-1-(1-ethyl-2-cyclohexen-1-yl)acetyl-1H-indol-3-yl]acrylate (Compound No. P-25—prepared as described in Preparation 4) were heated under reflux in 200 ml of mesitylene for 12 hours. To the mixture were then added 20 ml of 15% w/v ethanolic hydrogen chloride, and the reaction mixture was heated under reflux for 30 minutes. The mixture was then condensed by evaporation under reduced pressure, and the residue was purified by silica gel column chromatography using a 1:1 by volume mixture of ethyl acetate and hexane as eluent. The product was recrystallized from a mixture of ethyl acetate and diisopropyl ether, to give 21 g of the title compound as colorless needles melting at 144°–145° C.

Elemental Analysis: Calculated for $C_{31}H_{33}NO_4$: C, 76.99%; H, 6.88%; N, 2.90%. Found: C, 76.93%; H, 6.80%; N, 2.81%.

Infrared Absorption Spectrum (KBr) $\nu_{max}$cm$^{-1}$: 1735, 1695.

Nuclear Magnetic Resonance Spectrum (CDCl$_3$) $\delta$ ppm: 8.30 (1H, doublet, J=10 Hz).

Mass Spectrum (m/e): 483 (M+).

EXAMPLE 27

7-Benzyloxy-12a$\beta$-ethyl-1,2,3,3a$\beta$,4$\alpha$,5,11,12,-12a$\beta$,12b$\beta$-decahydro-11-oxobenzo[d,e]indolo[3,2,1-i,j]quinoline-4$\beta$-carboxylic acid (Compound No. 172)

4 g of allyl 7-benzyloxy-12a$\beta$-ethyl-1,2,3,3a$\beta$,-4$\alpha$,5,11,12,12a$\beta$,12b$\beta$-decahydro-11-oxobenzo[d,e]indolo[3,2,1-i,j]quinoline-4$\beta$-carboxylate (Compound No. 216—prepared as described in Example 26) and 3.02 g of potassium 2-ethylhexanoate were dissolved in a mixture of 70 ml of ethyl acetate and 30 ml of chloroform. To the solution were added 95 mg of triphenylphosphine and 95 mg of tetrakis(triphenylphosphine)palladium(O) under a nitrogen atmosphere. The reaction mixture was then stirred for 8 hours at room temperature. Diethyl ether was then added to the reaction mixture and the crystalline substance which separated was collected by filtration and washed with ethyl acetate. The crystals thus obtained were dissolved in water and washed with diethyl ether. The aqueous solution was acidified by the addition of a saturated aqueous solution of citric acid, and the crystalline substance which separated was collected by filtration, washed with water and recrystallized from a mixture of dioxane and diisopropyl ether, to give 2.4 g of the title compound as colorless powdery crystals melting at 240°–242° C.

Elemental Analysis: Calculated for $C_{28}H_{29}NO_4$: C, 75.82%; H, 6.59%; N, 3.16%. Found: C, 75.61%; H, 6.54%; N, 3.08%.

Infrared Absorption Spectrum (KBr) $\nu_{max}$cm$^{-1}$: 1728, 1698.

Nuclear Magnetic Resonance Spectrum [(CD$_3$)$_2$SO] $\delta$ ppm: 8.17 (1H, doublet, J=9 Hz).

Mass Spectrum (m/e): 443 (M+).

EXAMPLE 28

7-Benzyloxy-4$\beta$-benzyloxycarbonylamino-12a$\beta$-ethyl-2,3,3a$\beta$,4$\alpha$,5,12,12a$\beta$,12b$\beta$-octahydrobenzo-[d,e]indolo[3,2,1-i,j]quinolin-11(H)-one (Compound No. 184)

2.22 g of 7-benzyloxy-12a$\beta$-ethyl-1,2,3,3a$\beta$,-4$\alpha$,5,11,12,12a$\beta$,12b$\beta$-decahydro-11-oxobenzo[d,e]indolo[3,2,1-i,j]quinoline-4$\beta$-carboxylic acid (Compound No. 172—prepared as described in Example 27) were suspended in 50 ml of acetone. To the suspension was added 0.8 ml of triethylamine, whilst ice-cooling. 0.7 ml of ethyl chloroformate was then added dropwise thereto, and the mixture was stirred for 30 minutes. The reaction mixture was then poured into ice-water and extracted with methylene chloride. The extract was dried over anhydrous magnesium sulfate, and the solvent was distilled off under reduced pressure. The residue was dissolved in 20 ml of xylene and the solution was heated under reflux for 1 hour. To the solution were then added 5 ml of benzyl alcohol, and the reaction mixture was heated under reflux for 5 hours, and then condensed by evaporation under reduced pressure. The residue was purified by silica gel column chromatography, using a 1:4 by volume mixture of ethyl acetate and hexane as eluent, and the product was recrystallized from a mixture of ethyl acetate and diisopropyl ether, to give 1.78 g of the title compound as colorless prisms melting at 181°–183° C.

Elemental Analysis: Calculated for $C_{35}H_{36}N_2O_4$: C, 76.62%; H, 6.61%, N, 5.11%. Found: C, 76.92%; H, 6.78%; N, 4.90%.

Infrared Absorption Spectrum (KBr) $\nu_{max}cm^{-1}$: 1713, 1687.

Nuclear Magnetic Resonance Spectrum (CDCl$_3$) δ ppm: 8.28 (1H, doublet, J=10 Hz).

EXAMPLE 29

4β-Amino-12aβ-ethyl-7-hydroxy-2,3,3aβ,4α,5,12,-12aβ,12bβ-octahydrobenzo[d,e]indolo[3,2,1-i,j]quinolin-11(1H)-one hemihydrate (hemihydrate of Compound No. 197)

5.05 g of 7-benzyloxy-4β-benzyloxycarbonylamino-12aβ-ethyl-2,3,3aβ,4α,5,12,12aβ,12bβ-octahydrobenzo[d,e]indolo[3,2,1-i,j]quinolin-11(1H)-one (Compound No. 184—prepared as described in Example 28) were dissolved in 50 ml of N,N-dimethylformamide, and 1.5 g of a 10% w/w palladium-on-carbon catalyst was subsequently added to the resulting solution. Gaseous hydrogen was bubbled through the solution until no more was absorbed. The solids were then filtered off and the filtrate was condensed by evaporation under reduced pressure. The residue was recrystallized from dioxane to give 1.93 g of the title compound as colorless powdery crystals melting at 270°–273° C. (with decomposition).

Elemental Analysis: Calculated for $C_{20}H_{24}N_2O_2$ ½$H_2O$: C, 72.04%; H, 7.56%; N, 8.40%. Found: C, 72.39% H, 7.31%; N, 8.06%.

Infrared Absorption Spectrum (KBr) $\nu_{max}cm^{-1}$: 3330, 3270, 1690.

Nuclear Magnetic Resonance Spectrum [(CD$_3$)$_2$SO] δ ppm: 8.04 (1H, doublet, J=9 Hz).

Mass Spectrum (m/e): 324 (M+).

EXAMPLE 30

12aβ-Ethyl-2,3,3aβ,4,5,12,12aβ,12bβ-octahydrobenzo[d,e]indolo[3,2,1-i,j]quinolin-11(1H)-one (Compound No. 209)

To a suspension of 3.54 g of 12aβ-ethyl-11-oxo-1,2,3,3aβ,4α,5,11,12,12aβ,12bβ-decahydrobenzo[d,e]indolo[3,2,1-i,j]quinoline-4β-carboxylic acid (Compound No. 73—prepared following the procedures described in Example 3) in 20 ml of methylene chloride was added 1.4 ml of oxalyl chloride, and the mixture was heated under reflux for 2 hours. The reaction mixture was then condensed by evaporation under reduced pressure. The residue was dissolved in 20 ml of methylene chloride and the solution was added, with ice-cooling, to a solution of 1.47 g of N-hydroxy-2-pyridinethione in 1.8 ml of triethylamine. The mixture was stirred for 1 hour, after which it was washed with water and dried over anhydrous magnesium sulfate. It was then condensed by evaporation under reduced pressure. The residue was dissolved in 50 ml of toluene. To the solution were added 4.2 ml of tributyltin hydride under a nitrogen atmosphere, and the mixture was stirred at a temperature between 80° and 90° C. for 2 hours. It was then washed, in turn, with a 1N aqueous solution of hydrochloric acid, with a saturated aqueous solution of sodium hydrogen carbonate and with a saturated aqueous solution of sodium chloride, and dried over anhydrous magnesium sulfate. The solvent was then removed by evaporation under reduced pressure. The residue was purified by silica gel column chromatography using a 1:4 by volume mixture of ethyl acetate and hexane, and the product was recrystallized from ethyl acetate, to give 1.24 g of the title compound as colorless prisms melting at 187°–189° C.

Elemental Analysis: Calculated for $C_{20}H_{23}NO$: C, 81.87%; H, 7.90%; N, 4.77%. Found: C, 81.43%; H, 7.85%; N, 4.69%.

Infrared Absorption Spectrum (KBr) $\nu_{max}cm^{-1}$: 1695.

Nuclear Magnetic Resonance Spectrum (CDCl$_3$) δ ppm: 8.43 (1H, multiplet).

Mass Spectrum (m/e): 293 (M+).

EXAMPLE 31

7-Benzyloxy-12aβ-ethyl-4β-[2-(1-pyrrolidinyl)ethylcarbamoyl]-2,3,3aβ,4α,5,12,12aβ,12bβ-octahydrobenzo[d,e]indolo[3,2,1-i,j]quinolin-11(1H)-one (Compound No. 159)

1.33 g of 7-benzyloxy-12aβ-ethyl-11-oxo-1,2,3,3aβ,-4α,5,11,12,12aβ,12bβ-decahydrobenzo[d,e]indolo[3,2,1-i,j]quinoline-4β-carboxylic acid (Compound No. 172—prepared as described in Example 27) were dissolved, under a stream of nitrogen, in 10 ml of N,N-dimethylformamide, and then 0.46 ml of triethylamine and 0.54 g of diethyl phosphorocyanidate, followed by 0.38 g of 1-(2-aminoethyl)pyrrolidine were added to the resulting solution. The mixture was stirred at room temperature for 5 hours, after which it was poured into ice-water. A saturated aqueous solution of sodium hydrogen carbonate was added, and the resulting mixture was extracted with methylene chloride. The extract was dried over anhydrous magnesium sulfate, and then concentrated by evaporation under reduced pressure. The residue was purified by silica gel column chromatography, using a 1:1 by volume mixture of ethyl acetate and ethanol as eluent, to give 1 g of the title compound as crystals melting at 165°–170° C.

Nuclear Magnetic Resonance Spectrum (CDCl$_3$) δ ppm: 8.17 (1H, doublet, J=10 Hz).

EXAMPLE 32

7-Hydroxy-12aβ-ethyl-4β-[2-(1-pyrrolidinyl)ethylcarbamoyl]-2,3,3aβ,4α,5,12,12aβ,12bβ-octahydrobenzo[d,e]indolo[3,2,1-i,j]quinolin-11(1H)-one (Compound No. 161)

1 g of 7-benzyloxy-12aβ-ethyl-4β-[2-(1-pyrrolidinyl)ethylcarbamoyl]-2,3,3aβ,4α,5,12,12aβ,12bβ-octahydrobenzo[d,e]indolo[3,2,1-i,j]quinolin-11(1H)-one (Compound No. 159—prepared as described in Example 31) was dissolved in 20 ml of N,N-dimethylformamide. To the resulting solution was added 0.5 g of a 10% w/w palladium-on-carbon catalyst, and hydrogen gas was bubbled through the solution for 30 minutes, until absorption of hydrogen ceased. At this time, the reaction mixture was filtered to remove insolubles, and the filtrate was concentrated by evaporation under reduced pressure. The residue was purified by silica gel column chromatography, using 5% v/v triethylamine in ethanol as eluent, to give 0.369 g of the title compound as amorphous crystals.

Elemental Analysis: Calculated for $C_{27}H_{35}N_3O_3 \cdot \frac{4}{1}H_2O$: C, 62.17%; H, 8.31%; N, 8.06%.

Found: C, 63.00%; H, 7.98%; N, 7.85%.

Nuclear Magnetic Resonance Spectrum (CD$_3$OD) δppm: 8.08 (1H, doublet, J=9 Hz).

Mass Spectrum (m/e): 449 (M+).

EXAMPLE 33

7-Benzyloxy-12aβ-ethyl-4β-{3-[2-(1-pyrrolidinyl)ethyl]carbazoyl}-2,3,3aβ,4α,5,12,12aβ,12bβ-octahydrobenzo[d,e]indolo[3,2,1-i,j]quinolin-11(1H)-one (Compound No. 160)

1.33 g of 7-benzyloxy-12aβ-ethyl-11-oxo-1,2,3,3aβ,-4α,5,11,12,12aβ12bβ-decahydrobenzo[d,e]indolo[3,2,1-i,j]quinoline-4β-carboxylic acid (Compound No. 172—prepared as described in Example No. 27), 0.46 ml of triethylamine and 0.54 g of diethyl phosphorocyanidate were dissolved in 10 ml of N,N-dimethylformamide, and then 0.43 g of 1-(2-hydrazinoethyl)pyrrolidine were added to the resulting solution. The mixture was then stirred at room temperature for 5 hours, after which the mixture was poured into ice-water, and a saturated aqueous solution of sodium hydrogen carbonate was added. The resulting mixture was extracted with methylene chloride, and the extract was dried over anhydrous magnesium sulfate and concentrated by evaporation under reduced pressure. The residue was purified by silica gel column chromatography, using ethyl acetate, ethanol and then 3% v/v triethylamine in ethanol as eluents, to give 1.1 g of the title compound as crystals melting at 174°–177° C.

Nuclear Magnetic Resonance Spectrum (CDCl$_3$) δppm: 8.28 (1H, doublet, J=10 Hz).

EXAMPLE 34

7-Hydroxy-12aβ-ethyl-4β-{3-[2-(1-pyrrolidinyl)ethyl]carbazoyl}-2,3,3aβ,4α,5,12,12aβ,12bβ-octahydrobenzo[d,e]indolo[3,2,1-i,j]quinolin-11(1H)-one hemihydrate (hemihydrate of Compound No. 146)

1.1 g of 7-benzyloxy-12aβ-ethyl-4β-{3-[2-(1-pyrrolidinyl)ethyl]carbazoyl}-2,3,3aβ,4α,5,12,12aβ,12bβ-octahydrobenzo[d,e]indolo[3,2,1-i,j]quinolin-11(1H)-one (Compound No. 160—prepared as described in Example 33) was dissolved in 20 ml of N,N-dimethylformamide, and then 0.5 g of a 10% w/w palladium-on-carbon catalyst was added. Gaseous hydrogen was bubbled through the solution for 1 hour, until absorption of hydrogen ceased. At this time, the reaction mixture was filtered to remove solids, and the filtrate was concentrated by evaporation under reduced pressure. The residue was purified by silica gel column chromatography, using 5% v/v triethylamine in ethanol as eluent, to give 0.486 g of the title compound as amorphous crystals.

Elemental Analysis: Calculated for $C_{27}H_{36}N_4O_3 \cdot \frac{1}{2}H_2O$: C, 68.47%; H, 7.87%; N, 11.83%. Found: C, 68.39%; H, 7.55%; N, 11.68%.

Nuclear Magnetic Resonance Spectrum (CD$_3$OD) δppm: 8.08 (1H, doublet, J=9 Hz).

Mass Spectrum (m/e): 464 (M+).

Other compounds of the invention which have been prepared by various of the processes illustrated in the above Examples are:

Compound No. 112, melting at 304°–305° C. (with decomposition)

Compound No. 146, a colorless amorphous powder

Compound No. 155, melting at 220°–222° C.

Compound No. 156 hemihydrate, melting at 232°–234° C. (with decomposition)

Compound No. 157, melting at 208°–209° C.

Compound No. 159, melting at 140°–170° C.

Compound No. 160, melting at 174°–177° C.

Compound No. 161, a colorless amorphous powder

Compound No. 162, melting at 288°–290° C. (with decomposition)

Compound No. 208, melting at 267°–269° C. (with decomposition)

Compound No. 215, an oil

Compound No. 216, melting at 144°–145° C.

Compound No. 217, melting at 99°–101° C.

Compound No. 218, melting at 147°–148° C.

Compound No. 219, melting at 112°–115° C.

Compound No. 220, melting at 170°–171° C.

Compound No. 221, melting at 129°–130° C.

We claim:

1. A compound of formula (I):

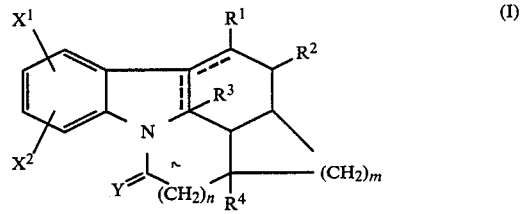

in which:

the dotted lines represent one single carbon-carbon bond and one double carbon-carbon bond or two single carbon-carbon bonds;

m is an integer from 2 to 7;

n is an integer from 1 to 3;

Y represents 2 hydrogen atoms or an oxo group;

$R^1$ represents a hydrogen atom or a $C_1$–$C_6$ alkyl group;

$R^2$ represents a hydrogen atom, a carboxy group, a group of formula —NHCOOR$^b$ in which R$^b$ represents a $C_1$–$C_6$ alkyl group, a substituted $C_1$–$C_6$ alkyl group, an aralkyl group wherein the aryl part is $C_6$–$C_{10}$ carbocyclic aryl and the alkyl part is $C_1$–$C_6$ alkyl, a substituted aralkyl group wherein the aryl part is $C_6$–$C_{10}$ carbocyclic aryl and the alkyl part is $C_1$–$C_6$ alkyl, a $C_3$–$C_6$ alkenyl group, a $C_3$–$C_6$ haloalkenyl group, a $C_3$–$C_{10}$ cycloalkyl group or a substituted $C_3$–$C_{10}$ cycloalkyl group, a group of formula —NR$_2$, a quaternary ammonium group of formula —N$^+$(R')$_3$, a group of formula —CONR$_2$, a group of formula —NHNR$_2$, a group of formula —NHCONR$_2$, an aminoalkanoylamino group wherein the alkanoyl part is $C_2$–$C_7$ alkanoyl, a group of formula —CO.NH.NR$_2$ or a group of formula —CO.NH.N=CHR";

the two atoms or groups represented by R are independently selected from the group consisting of hydrogen atoms, C$_1$-C$_6$ alkyl groups, substituted C$_1$-C$_6$ alkyl groups, aralkyl groups where the aryl part is C$_6$-C$_{10}$ carbocyclic aryl and the alkyl part is C$_1$-C$_6$ alkyl, substituted aralkyl groups where the aryl part is C$_6$-C$_{10}$ carbocyclic aryl and the alkyl part is C$_1$-C$_6$ alkyl, heterocyclic groups and substituted heterocyclic groups; or the two symbols R, together with the nitrogen atom to which they are attached, represent a nitrogenous heterocyclic group;

the three groups represented by R' are independently selected from the group consisting of C$_1$-C$_6$ alkyl groups, substituted C$_1$-C$_6$ alkyl groups, aralkyl groups where the aryl part is C$_6$-C$_{10}$ carbocyclic aryl and the alkyl part is C$_1$-C$_6$ alkyl and substituted aralkyl groups where the aryl part is C$_6$-C$_{10}$ carbocyclic aryl and the alkyl part is C$_1$-C$_6$ alkyl;

R" represents a C$_1$-C$_5$ alkyl group or a phenyl group;

R$^3$ represents a hydrogen atom, a C$_1$-C$_3$ alkyl group or a substituted C$_1$-C$_3$ alkyl group;

R$^4$ represents a hydrogen atom, a C$_1$-C$_6$ alkyl group, a C$_3$-C$_6$ alkenyl group, a C$_3$-C$_6$ alkynyl group, an aralkyl group wherein the aryl part is a C$_6$-C$_{10}$ carbocyclic aryl group and the alkyl part is C$_1$-C$_6$ alkyl, or the phenyl group;

X$^1$ and X$^2$ are independently selected from the group consisting of hydrogen atoms, C$_1$-C$_6$ alkyl groups, substituted C$_1$-C$_6$ alkyl groups, C$_1$-C$_6$ alkoxy groups, aralkyloxy groups wherein the aryl part is a C$_6$-C$_{10}$ carbocyclic aryl group and the alkyl part is a C$_1$-C$_6$ alkyl group, hydroxy groups, halogen atoms, trifluoromethyl groups, nitro groups, amino groups, aminoalkanoylamino groups wherein the alkanoyl part is C$_2$-C$_7$ alkanoyl, mono- and di-alkylaminoalkanoylamino groups wherein the alkanoyl part is C$_2$-C$_7$ alkanoyl and the or each alkyl part is C$_1$-C$_6$ alkyl and is substituted or unsubstituted, C$_2$-C$_7$ alkanoyloxy groups, carboxy groups, carbamoyl groups, mono- and di-alkylcarbamoyl groups where the or each alkyl part is C$_1$-C$_6$ alkyl and cyano groups;

the substituents on said alkyl, cycloalkyl, alkoxy, aralkyl and heterocyclic groups are from 1 to 2 substituents selected from the group consisting of halogen atoms, cyano groups, nitro groups, hydroxy groups, C$_1$-C$_4$ alkoxy groups, mercapto groups, C$_1$-C$_4$ alkylthio groups, C$_1$-C$_6$ alkanoyl groups, carboxy groups, alkoxycarbonyl groups where the alkoxy part is C$_1$-C$_4$ alkoxy, amino groups, C$_1$-C$_4$ alkylamino groups, dialkylamino groups where each alkyl part is C$_1$-C$_4$ alkyl, carbamoyl groups, alkylcarbamoyl groups where the alkyl part is C$_1$-C$_4$ alkyl, dialkylcarbamoyl groups where each alkyl part is C$_1$-C$_4$ alkyl, and, only as substituents on substituted alkyl and alkoxy groups, C$_3$-C$_{10}$ cycloalkyl groups, substituted C$_3$-C$_{10}$ cycloalkyl groups, heterocyclic groups and substituted heterocyclic groups, and, only as substituents on cycloalkyl groups and substituted aryl parts of aralkyl groups, C$_1$-C$_4$ alkyl groups and substituted C$_1$-C$_4$ alkyl groups, and, only as substituents on substituted heterocyclic groups, C$_1$-C$_4$ alkyl groups, substituted C$_1$-C$_4$ alkyl groups, C$_6$-C$_{10}$ carbocyclic aryl groups, substituted C$_6$-C$_{10}$ carbocyclic aryl groups, arylalkenoyl groups wherein the aryl part is C$_6$-C$_{10}$ carbocyclic aryl and the alkenoyl part is C$_3$-C$_6$ alkenoyl and substituted arylalkenoyl wherein the aryl part is substituted C$_6$-C$_6$ carbocyclic aryl and the alkenoyl part is C$_3$-C$_6$ alkenoyl;

said heterocyclic groups being selected from the group consisting of pyrrolidinyl, morpholinyl, piperidinoyl and piperazinyl;

said nitrogenous heterocyclic group being selected from the group consisting of: N-(2-cyclohexylethyl)carbamoyl, N-[2-(1-pyrrolidinyl)ethyl]carbamoyl, N-(2-piperidinoethyl)carbamoyl, N-(2-morpholinoethyl)carbamoyl, N-(3-morpholinopropyl)carbamoyl, N-(4-morpholinobutyl)carbamoyl, N-[2-(4-methyl-1-piperazinyl)ethyl]carbamoyl, N-[2-(4-phenyl-1-piperazinyl)ethyl]carbamoyl, N-[2-(4-ethoxycarbonyl-1-piperazinyl)ethyl]carbamoyl, N-benzylcarbamoyl, N-4-methylbenzylcarbamoyl, N-2-chlorobenzylcarbamoyl, N-4-chlorobenzylcarbamoyl, N-2-methoxybenzylcarbamoyl, N-4-methoxybenzylcarbamoyl, N-3,4-dimethoxybenzylcarbamoyl, N-phenethylcarbamoyl, N-4-methylphenethylcarbamoyl, N-4-chlorophenethylcarbamoyl, N-4-methoxyphenethylcarbamoyl, N-3,4-dimethoxyphenethylcarbamoyl, N-3,4,5-trimethoxyphenethylcarbamoyl, N-3-phenylpropylcarbamoyl, N-4-phenylbutylcarbamoyl, N-furfurylcarbamoyl, N-(2-pyridylmethyl)carbamoyl, N-(4-pyridylmethyl)carbamoyl, N-(2-pyrid-2-ylethyl)carbamoyl, N-cyclopentylcarbamoyl, N-cyclohexylcarbamoyl, N-phenylcarbamoyl, N-4-tolylcarbamoyl, N-4-chlorophenylcarbamoyl, N-4-methoxyphenylcarbamoyl, N-2-pyridylcarbamoyl, N-2-furylcarbamoyl, N-morpholinocarbamoyl, N-piperidinocarbamoyl and N-piperazinylcarbamoyl groups; and heterocyclic-carbonyl groups, selected from the group consisting of 1-pyrrolidinylcarbonyl, piperidinocarbonyl, 4-methyl-1-piperazinylcarbonyl and 4-phenyl-1-piperazinylcarbonyl groups, or a pharmaceutically acceptable salt or ester thereof.

2. A compound as claimed in claim 1, having the formula (IV):

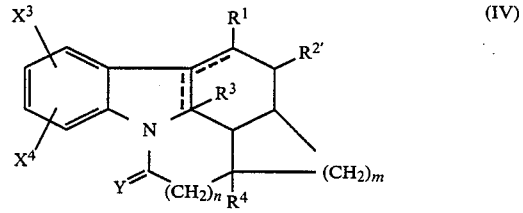

wherein R$^1$, R$^3$, R$^4$, Y, n, m and the dotted lines are as in claim 1;

R$^{2'}$ represents any one of the groups or atoms defined for R$^2$ or a group of formula COOR$^a$ wherein R$^a$ represents a C$_1$-C$_6$ alkyl group, a substituted C$_1$-C$_6$ alkyl group, an aralkyl group wherein the aryl part is C$_6$-C$_{10}$ carbocyclic aryl and is substituted or unsubstituted and the alkyl part is C$_1$-C$_6$ alkyl, a C$_3$-C$_6$ alkenyl group, a C$_3$-C$_6$ haloalkenyl group, a C$_3$-C$_{10}$ cycloalkyl group or a C$_3$-C$_{10}$ cycloalkyl group having from 1 to 5 C$_1$-C$_4$ alkyl substituents; and $X^3$ and $X^4$ are independently selected from the group consisting of the groups and atoms defined for $X^1$ and $X^2$ and groups of formula $COOR^a$ in which $R^a$ is as defined above, or a pharmaceutically acceptable salt thereof.

3. A compound as claimed in claim 2, in which:

m is 2 or 3;

n is 1;

Y represents an oxo group;

$R^1$ represents a hydrogen atom;

$R^{2'}$ represents a group of formula $COOR^a$, in which $R^a$ represents an aminoalkyl group, or $R^{2'}$ represents a group of formula $-NR_2$, in which the two groups represented by R are independently selected from the group consisting of hydrogen atoms and $C_1-C_4$ alkyl groups, an aminoalkanoylamino group, in which the alkanoyl part is a $C_2-C_7$ alkanoyl group, a group of formula $-CO.NH.NR_2$, in which the two groups represented by R are independently selected from the group consisting of $C_1-C_6$ alkyl groups, or the two groups represented by R together with the nitrogen atom to which they are attached represent a nitrogenous heterocyclic group, or a group of formula $-CO.NHNHR$, in which R represents a $C_1-C_6$ aminoalkyl group, a phenyl group, an aralkyl group in which the aryl part is $C_6-C_{10}$ carbocyclic aryl and the alkyl part is $C_1-C_4$ alkyl, a heterocyclic group, a hydrogen atom, a $C_1-C_4$ alkyl group or a $C_1-C_4$ hydroxyalkyl group;

$R^3$ represents a hydrogen atom;

$R^4$ represents a hydrogen atom, a $C_1-C_4$ alkyl group or an aralkyl group in which the aryl part is $C_6-C_{10}$ carbocyclic aryl and the alkyl part is $C_1-C_4$ alkyl; and $X^3$ and $X^4$ are independently selected from the group consisting of hydrogen atoms and hydroxy groups.

4. A compound as claimed in claim 1, having the formula (V):

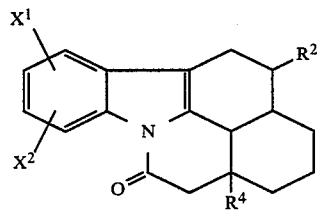

(V)

(in which:

$R^2$ represents a 2-(1-piperazinyl)ethoxycarbonyl group, a 2-(1-piperazinyl)ethoxycarbonyl group having an alkyl, phenyl, substituted phenyl or alkoxycarbonyl substituent at the 4-position of the piperazinyl group, an amino group, a dimethylamino group, an aminoacetamido group, an aminoacetamido group having one or two $C_1-C_4$ alkyl substituents on the amino group, a carbamoyl group having a single dimethylamino, morpholino, piperidino, 1-pyrrolidinyl or 4-methyl-1-piperazinyl substituent, a carbazoyl group or a carbazoyl group having on the 3-nitrogen atom a substituent selected from the group consisting of methyl, 2-hydroxyethyl, phenyl, benzyl, pyridyl, 2-(1-pyrrolidinyl)ethyl, 2-piperidinoethyl, 2-morpholinoethyl and 2-(4-methyl-1-piperazinyl)ethyl substituents;

$R^4$ represents a hydrogen atom or a methyl, ethyl, propyl, isopropyl, butyl, 4-methoxyphenethyl, 3,4-dimethoxyphenethyl or 3,4,5-trimethoxyphenethyl group; and $X^1$ and $X^2$ are independently selected from the group consisting of hydrogen atoms and hydroxy groups at the 6-, 7- and 8-positions.

5. A compound as claimed in claim 4, wherein either both $X^1$ and $X^2$ represent hydrogen atoms, or $X^2$ represents a hydrogen atom and $X^1$ represents a 6-hydroxy or 7-hydroxy group or $X^1$ represents a 7-hydroxy group and $X^2$ represents an 8-hydroxy group.

6. A compound of formula (I-5):

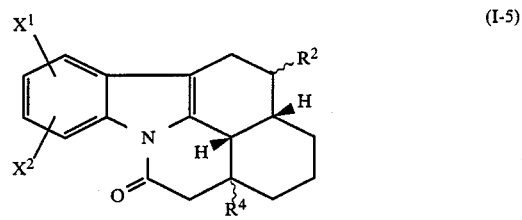

(I-5)

wherein $X^1$, $X^2$, $R^2$ and $R^4$ are as defined below:

| Cpd No | $X^1$ | $X^2$ | $R^2$ | $R^4$ |
|---|---|---|---|---|
| 107 | 7-OH | H | $NH_2(\beta)$ | $H(\beta)$ |
| 111 | 6-OH | H | $NH_2(\beta)$ | $H(\beta)$ |
| 112 | 6-OH | H | $NH_2(\beta)$ | $Me(\beta)$ |
| 113 | 7-OH | 8-OH | $NH_2(\beta)$ | $Me(\beta)$ |
| 114 | 7-OH | H | $NH_2(\alpha)$ | $Et(\beta)$ |
| 115 | 6-OH | H | $NH_2(\beta)$ | $Pr(\beta)$ |
| 116 | 7-OH | 8-OH | $NH_2(\beta)$ | $Pr(\beta)$ |
| 117 | 6-OH | H | $NH_2(\beta)$ | $iPr(\beta)$ |
| 118 | 6-OH | H | $NH_2(\beta)$ | 4-OMe—PhEt($\beta$) |
| 119 | 7-OH | H | $NH_2(\beta)$ | 4-OMe—PhEt($\beta$) |
| 120 | 6-OH | H | $NH_2(\beta)$ | 3,4-diOMe—PhEt($\beta$) |
| 121 | 7-OH | H | $NH_2(\beta)$ | 3,4-diOMe—PhEt($\beta$) |
| 122 | 6-OH | H | $NH_2(\beta)$ | 3,4,5-triOMe—PhEt($\beta$) |
| 123 | 6-OH | H | $NMe_2(\beta)$ | $Me(\beta)$ |
| 124 | 7-OH | H | $NMe_2(\beta)$ | $Me(\beta)$ |
| 125 | 6-OH | H | $NMe_2(\beta)$ | $Et(\beta)$ |
| 126 | 7-OH | H | $NMe_2(\beta)$ | $Et(\beta)$ |

-continued

| Cpd No | $X^1$ | $X^2$ | $R^2$ | $R^4$ |
|---|---|---|---|---|
| 127 | 6-OH | H | NMe$_2$($\beta$) | 3,4-diOMe—PhEt($\beta$) |
| 128 | 7-OH | H | NMe$_2$($\beta$) | 3,4-diOMe—PhEt($\beta$) |
| 129 | 6-OH | H | NMe$_2$($\beta$) | 4-OMe—PhEt($\beta$) |
| 130 | 7-OH | H | NMe$_2$($\beta$) | 4-OMe—PhEt($\beta$) |
| 131 | 6-OH | H | NHCOCH$_2$NEt$_2$($\beta$) | Et($\beta$) |
| 132 | 7-OH | H | NHCOCH$_2$NEt$_2$($\beta$) | Et($\beta$) |
| 133 | 6-OH | H | CONHNMe$_2$($\beta$) | Et($\beta$) |
| 134 | 7-OH | H | CONHNMe$_2$($\beta$) | Et($\beta$) |
| 135 | 6-OH | H | CONHNMe$_2$($\beta$) | 4-OMe—PhEt($\beta$) |
| 136 | 6-OH | H | CONHNMe$_2$($\beta$) | 3,4-diOMePhEt($\beta$) |
| 137 | 6-OH | H | CONHNH$_2$($\beta$) | Et($\beta$) |
| 138 | 7-OH | H | CONHNH$_2$($\beta$) | Et($\beta$) |
| 139 | 6-OH | H | CONHNH$_2$($\beta$) | 3,4-diOMe—PhEt($\beta$) |
| 140 | 6-OH | H | COO(4-MePip—Et)($\beta$) | Et($\beta$) |
| 141 | 6-OH | H | OH—Et—NHNHCO—($\beta$) | Et($\beta$) |
| 142 | 7-OH | H | OH—Et—NHNHCO—($\beta$) | Et($\beta$) |
| 143 | 6-OH | H | OH—Et—NHNHCO—($\beta$) | 3,4-diOMe—PhEt($\beta$) |
| 144 | 6-OH | H | CONHNHPh($\beta$) | Et($\beta$) |
| 145 | 6-OH | H | CONHNH(Prl—Et)($\beta$) | Me($\beta$) |
| 146 | 7-OH | H | CONHNH(Prl—Et)($\beta$) | Et($\beta$) |
| 147 | 6-OH | H | CONHNH(Prl—Et)($\beta$) | 3,4-diOMe—PhEt($\beta$) |
| 148 | 6-OH | H | CONHNH(Pid—Et)($\beta$) | Me($\beta$) |
| 149 | 6-OH | H | CONHNH(Pid—Et)($\beta$) | 4-OMe—PhEt($\beta$) |
| 150 | 6-OH | H | CONHNH(Pid—Et)($\beta$) | 3,4-diOMe—PhEt($\beta$) |
| 151 | 6-OH | H | CONHNH(4-MePip—Et)($\beta$) | Et($\beta$) |
| 152 | 6-OH | H | CONHNH(4-MePip—Et)($\beta$) | 3,4-diOMe—PhEt($\beta$) |
| 153 | 6-OH | H | CONHNHMe($\beta$) | Et($\beta$) |
| 154 | 6-OH | H | CONHNHMe($\beta$) | 3,4-diOMe—PhEt($\beta$) |
| 196 | 7-OH | H | NH$_2$($\beta$) | Me($\beta$) |
| 197 | 7-OH | H | NH$_2$($\beta$) | Et($\beta$) |
| 198 | 7-OH | H | NH$_2$($\beta$) | Pr($\beta$) |
| 199 | 7-OH | H | NH$_2$($\beta$) | iPr($\beta$) |
| 204 | 6-OH | H | NH$_2$($\beta$) | Et($\beta$) |
| 205 | 6-OH | H | NH$_2$($\alpha$) | Et($\beta$) |
| 207 | 7-OH | 8-OH | NH$_2$($\beta$) | Et($\beta$) | wherein:
 All=allyl;
 Brn=2-bornyl;
 Bu=butyl;
 Bz=benzyl;
 Cin=cinnamoyl;
 Et=ethyl;
 iPr=isopropyl;
 Me=methyl;
 Mor=morpholino;
 mTo=m-tolyl;
 Ph=phenyl;
 Pid=piperidino;
 Pip=1-piperazinyl;
 Pr=propyl;
 Prl=1-pyrrolidinyl.

7. A pharmaceutical composition comprising an anti-arrhythmic effective amount of an anti-arrhythmic compound in admixture with a pharmaceutically acceptable carrier or diluent, wherein the anti-arrhythmic compound is selected from the group consisting of compounds of formula (I):

in which:

the dotted lines represent one single carbon-carbon bond and one double carbon-carbon bond or two single carbon-carbon bonds;
m is an integer from 2 to 7;
n is an integer from 1 to 3;
Y represents 2 hydrogen atoms or an oxo group;
$R^1$ represents a hydrogen atom or a $C_1$-$C_6$ alkyl group;
$R^2$ represents a hydrogen atom, a carboxy group, a group of formula —NHCOOR$^b$ in which R$^b$ represents a $C_1$-$C_6$ alkyl group, a substituted $C_1$-$C_6$ alkyl group, an aralkyl group wherein the aryl part is $C_6$-$C_{10}$ carbocyclic aryl and the alkyl part is $C_1$-$C_6$ alkyl, a substituted aralkyl group wherein the aryl part is $C_6$-$C_{10}$ carbocyclic aryl and the alkyl part is $C_1$-$C_6$ alkyl, a $C_3$-$C_6$ alkenyl group, a $C_3$-$C_6$ haloalkenyl group, a $C_3$-$C_{10}$ cycloalkyl group or a substituted $C_3$-$C_{10}$ cycloalkyl group, a group of formula —NR$_2$, a quaternary ammonium group of formula —N$^+$(R')$_3$, a group of formula —CONR$_2$, a group of formula —NHNR$_2$, a group of formula —NHCONR$_2$, an aminoalkanoylamino group wherein the alkanoyl part is $C_2$-$C_7$ alkanoyl, a group of formula —CO.NH.NR$_2$ or a group of formula —CO.NH.N=CHR'';
the two atoms or groups represented by R are independently selected from the group consisting of hydrogen atoms, $C_1$-$C_6$ alkyl groups, substituted $C_1$-$C_6$ alkyl groups, aralkyl groups where the aryl part is $C_6$-$C_{10}$ carbocyclic aryl and the alkyl part is $C_1$-$C_6$ alkyl, substituted aralkyl groups where the aryl part is $C_6$-$C_{10}$ carbocyclic aryl and the alkyl part is $C_1$-$C_6$ alkyl, heterocyclic groups and substituted heterocyclic groups;

or the two symbols R, together with the nitrogen atom to which they are attached, represent a nitrogenous heterocyclic group;

the three groups represented by R' are independently selected from the group consisting of $C_1$–$C_6$ alkyl groups, substituted $C_1$–$C_6$ alkyl groups, aralkyl groups where the aryl part is $C_6$–$C_{10}$ carbocyclic aryl and the alkyl part is $C_1$–$C_6$ alkyl and substituted aralkyl groups where the aryl part is $C_6$–$C_{10}$ carbocyclic aryl and the alkyl part is $C_1$–$C_6$ alkyl;

R" represents a $C_1$–$C_6$ alkyl group or a phenyl group;

$R^3$ represents a hydrogen atom, a $C_1$–$C_3$ alkyl group or a substituted $C_1$–$C_3$ alkyl group;

$R^4$ represents a hydrogen atom, a $C_1$–$C_6$ alkyl group, a $C_3$–$C_6$ alkenyl group, a $C_3$–$C_6$ alkynyl group, an aralkyl group wherein the aryl part is a $C_6$–$C_{10}$ carbocyclic aryl group and the alkyl part is $C_1$–$C_6$ alkyl, or the phenyl group;

$X^1$ and $X^2$ are independently selected from the group consisting of hydrogen atoms, $C_1$–$C_6$ alkyl groups, substituted $C_1$–$C_6$ alkyl groups, $C_1$–$C_6$ alkoxy groups, aralkyloxy groups wherein the aryl part is a $C_6$–$C_{10}$ carbocyclic aryl group and the alkyl part is a $C_1$–$C_6$ alkyl group, hydroxy groups, halogen atoms, trifluoromethyl groups, nitro groups, amino groups, aminoalkanoylamino groups wherein the alkanoyl part is $C_2$–$C_7$ alkanoyl, mono- and dialkylaminoalkanoylamino groups wherein the alkanoyl part is $C_2$–$C_7$ alkanoyl and the or each alkyl part is $C_1$–$C_6$ alkyl and is substituted or unsubstituted, $C_2$–$C_7$ alkanoyloxy groups, carboxy groups, carbamoyl groups, mono- and di-alkylcarbamoyl groups where the or each alkyl part is $C_1$–$C_6$ alkyl and cyano groups;

the substituents on said alkyl, cycloalkyl, alkoxy, aralkyl and heterocyclic groups are from 1 to 2 substituents selected from the group consisting of halogen atoms, cyano groups, nitro groups, hydroxy groups, $C_1$–$C_4$ alkoxy groups, mercapto groups, $C_1$–$C_4$ alkylthio groups, $C_1$–$C_6$ alkanoyl groups, carboxy groups, alkoxycarbonyl groups where the alkoxy part is $C_1$–$C_4$ alkoxy, amino groups, $C_1$–$C_4$ alkylamino groups, dialkylamino groups where each alkyl part is $C_1$–$C_4$ alkyl, carbamoyl groups, alkylcarbamoyl groups where the alkyl part is $C_1$–$C_4$ alkyl, dialkylcarbamoyl groups where each alkyl part is $C_1$–$C_4$ alkyl, and, only as substituents on substituted alkyl and alkoxy groups, $C_3$–$C_{10}$ cycloalkyl groups, substituted $C_1$–$C_{10}$ cycloalkyl groups, heterocyclic groups and substituted heterocyclic groups, and, only as substituents on cycloalkyl groups and substituted aryl parts of aralkyl groups, $C_1$–$C_4$ alkyl groups and substituted $C_1$–$C_4$ alkyl groups, and, only as substituents on substituted heterocyclic groups, $C_1$–$C_4$ alkyl groups, substituted $C_1$–$C_4$ alkyl groups, $C_6$–$C_{10}$ carbocyclic aryl groups, substituted $C_6$–$C_{10}$ carbocyclic aryl groups, arylalkenoyl groups wherein the aryl part is $C_6$–$C_{10}$ carbocyclic aryl and the alkenoyl part is $C_3$–$C_6$ alkenoyl and substituted arylalkenoyl wherein the aryl part is substituted $C_6$–$C_6$ carbocyclic aryl and the alkenoyl part is $C_3$–$C_6$ alkenoyl;

said heterocyclic groups being selected from the group consisting of pyrrolidinyl, morpholinyl, piperidinoyl and piperazinyl;

said nitrogenous heterocyclic group being selected from the group consisting of: N-(2-cyclohexylethyl)carbamoyl, N-[2-(1-pyrrolidinyl)ethyl]carbamoyl, N-(2-piperidinoethyl)carbamoyl, N-(2-morpholinoethyl)carbamoyl, N-(3-morpholinopropyl)carbamoyl, N-(4-morpholinobutyl)carbamoyl, N-[2-(4-methyl-1-piperazinyl)ethyl]carbamoyl, N-[2-(4-phenyl-1-piperazinyl)ethyl]carbamoyl, N-[2-(4-ethoxycarbonyl-1-piperazinyl)ethyl]carbamoyl, N-benzylcarbamoyl, N-4-methylbenzylcarbamoyl, N-2-chlorobenzylcarbamoyl, N-4-chlorobenzylcarbamoyl, N-2-methoxybenzylcarbamoyl, N-4-methoxybenzylcarbamoyl, N-3,4-dimethoxybenzylcarbamoyl, N-phenethylcarbamoyl, N-4-methylphenethylcarbamoyl, N-4-chlorophenethylcarbamoyl, N-4-methoxyphenethylcarbamoyl, N-3,4-dimethoxyphenethylcarbamoyl, N-3,4,5-trimethoxyphenethylcarbamoyl, N-3-phenylpropylcarbamoyl, N-4-phenylbutylarbamoyl, N-furfurylcarbamoyl, N-(2-pyridylmethyl)carbamoyl, N-(4-pyridylmethyl)carbamoyl, N-(2-pyrid-2-ylethyl)carbamoyl, N-cyclopentylcarbamoyl, N-cyclohexylcarbamoyl, N-phenylcarbamoyl, N-4-tolylcarbamoyl, N-4-chlorophenylcarbamoyl, N-4-methoxyphenylcarbamoyl, N-2-pyridylcarbamoyl, N-2-furylcarbamoyl, N-morpholinocarbamoyl, N-piperidinocarbamoyl and N-piperazinylcarbamoyl groups; and heterocyclic-carbonyl groups, selected from the group consisting of 1-pyrrolidinylcarbonyl, piperidinocarbonyl, 4-methyl-1-piperazinylcarbonyl and 4-phenyl-1-piperazinylcarbonyl groups, or a pharmaceutically acceptable salt or ester thereof.

8. A composition as claimed in claim 7, wherein said anti-arrhythmic compound has the formula (IV):

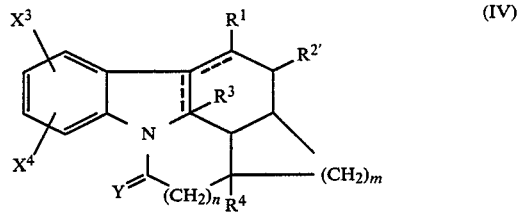

(IV)

wherein $R^1$, $R^3$, $R^4$, Y, n, m and the dotted lines are as in claim 7;

$R^{2'}$ represents any one of the groups or atoms defined for $R^2$ or a group of formula $COOR^a$ wherein $R^a$ represents a $C_1$–$C_6$ alkyl group, a substituted $C_{1-C6}$ alkyl group, an aralkyl group wherein the aryl part is $C_6$–$C_{10}$ carbocyclic aryl and is substituted or unsubstituted and the alkyl part is $C_1$–$C_6$ alkyl, a $C_3$–$C_6$ alkenyl group, a $C_3$–$C_6$ haloalkenyl group, a $C_3$–$C_{10}$ cycloalkyl group or a $C_3$–$C_{10}$ cycloalkyl group having from 1 to 5 $C_1$–$C_4$ alkyl substituents; and $X^3$ and $X^4$ are independently selected from the group consisting of the groups and atoms defined for $X^1$ and $X^2$ and groups of formula $COOR^a$ in which $R^a$ is as defined above, or is a salt thereof.

9. A composition as claimed in claim 8, in which:
m is 2 or 3;
n is 1;
Y represents an oxo group;
$R^1$ represents a hydrogen atom;

R2' represents a group of formula COOR$^a$, in which R$^a$ represents an aminoalkyl group, or R2' represents a group of formula —NR$_2$, in which the two groups represented by R are independently selected from the group consisting of hydrogen atoms and C$_1$-C$_4$ alkyl groups, an aminoalkanoylamino group, in which the alkanoyl part is a C$_2$-C$_7$ alkanoyl group, a group of formula —CO.NH.NR$_2$, in which the two groups represented by R are independently selected from the group consisting of C$_1$-C$_6$ alkyl groups, or the two groups represented by R together with the nitrogen atom to which they are attached represent a nitrogenous heterocyclic group, or a group of formula —CO.NHNHR, in which R represents a C$_1$-C$_6$ aminoalkyl group, a phenyl group, an aralkyl group in which the aryl part is C$_6$-C$_{10}$ carbocyclic aryl and the alkyl part is C$_1$-C$_4$ alkyl, a heterocyclic group, a hydrogen atom, a C$_1$-C$_4$ alkyl group or a C$_1$-C$_4$ hydroxyalkyl group;

R$^3$ represents a hydrogen atom;

R$^4$ represents a hydrogen atom, a C$_1$-C$_4$ alkyl group or an aralkyl group in which the aryl part is C$_6$-C$_{10}$ carbocyclic aryl and the alkyl part is C$_1$-C$_4$ alkyl; and X$^3$ and X$^4$ are independently selected from the group consisting of hydrogen atoms and hydroxy groups.

10. A composition as claimed in claim 7, wherein said anti-arrhythmic compound has the formula (V):

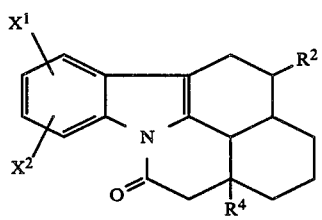

(V)

(in which:
R$^2$ represents a 2-(1-piperazinyl)ethoxycarbonyl group, a 2-(1-piperazinyl)ethoxycarbonyl group having an alkyl, phenyl, substituted phenyl or alkoxycarbonyl substituent at the 4-position of the piperazinyl group, an amino group, a dimethylamino group, an aminoacetamido group, an aminoacetamido group having one or two C$_1$-C$_4$ alkyl substituents on the amino group, a carbamoyl group having a single dimethylamino, morpholino, piperidino, 1-pyrrolidinyl or 4-methyl-1-piperazinyl substituent, a carbazoyl group or a carbazoyl group having on the 3-nitrogen atom a substituent selected from the group consisting of methyl, 2-hydroxyethyl, phenyl, benzyl, pyridyl, 2-(1-pyrrolidinyl)ethyl, 2-piperidinoethyl, 2-morpholinoethyl and 2-(4-methyl-1-piperazinyl)ethyl substituents;

R$^4$ represents a hydrogen atom or a methyl, ethyl, propyl, isopropyl, butyl, 4-methoxyphenethyl, 3,4-dimethoxyphenethyl or 3,4,5-trimethoxyphenethyl group; and X$^1$ and X$^2$ are independently selected from the group consisting of hydrogen atoms and hydroxy groups at the 6-, 7- and 8-positions.

11. A composition as claimed in claim 10, wherein either both X$^1$ and X$^2$ represents hydrogen atom, or X$^2$ represents a hydrogen atom and X$^1$ represents a 6-hydroxy or 7-hydroxy group or X$^1$ represents a 7-hydroxy group and X$^2$ represents an 8-hydroxy group.

12. A composition as claimed in claim 7 wherein said compound has the formula (I-5):

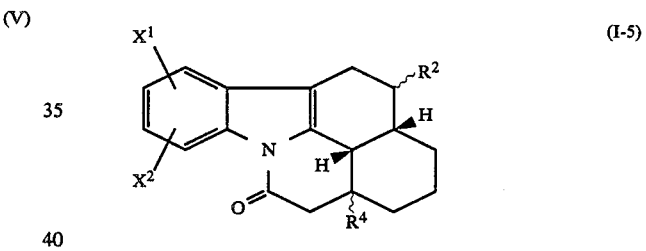

(I-5)

wherein X$^1$, X$^2$, R$^2$ and R$^4$ are as defined below:

| Cpd No | X$^1$ | X$^2$ | R$^2$ | R$^4$ |
|---|---|---|---|---|
| 107 | 7-OH | H | NH$_2$($\beta$) | H($\beta$) |
| 111 | 6-OH | H | NH$_2$($\beta$) | H($\beta$) |
| 112 | 6-OH | H | NH$_2$($\beta$) | Me($\beta$) |
| 113 | 7-OH | 8-OH | NH$_2$($\beta$) | Me($\beta$) |
| 114 | 7-OH | H | NH$_2$($\alpha$) | Et($\beta$) |
| 115 | 6-OH | H | NH$_2$($\beta$) | Pr($\beta$) |
| 116 | 7-OH | 8-OH | NH$_2$($\beta$) | Pr($\beta$) |
| 117 | 6-OH | H | NH$_2$($\beta$) | iPr($\beta$) |
| 118 | 6-OH | H | NH$_2$($\beta$) | 4-OMe—PhEt($\beta$) |
| 119 | 7-OH | H | NH$_2$($\beta$) | 4-OMe—PhEt($\beta$) |
| 120 | 6-OH | H | NH$_2$($\beta$) | 3,4-diOMe—PhEt($\beta$) |
| 121 | 7-OH | H | NH$_2$($\beta$) | 3,4-diOMe—PhEt($\beta$) |
| 122 | 6-OH | H | NH$_2$($\beta$) | 3,4,5-triOMe—PhEt($\beta$) |
| 123 | 6-OH | H | NMe$_2$($\beta$) | Me($\beta$) |
| 124 | 7-OH | H | NMe$_2$($\beta$) | Me($\beta$) |
| 125 | 6-OH | H | NMe$_2$($\beta$) | Et($\beta$) |
| 126 | 7-OH | H | NMe$_2$($\beta$) | Et($\beta$) |
| 127 | 6-OH | H | NMe$_2$($\beta$) | 3,4-diOMe—PhEt($\beta$) |
| 128 | 7-OH | H | NMe$_2$($\beta$) | 3,4-diOMe—PhEt($\beta$) |
| 129 | 6-OH | H | NMe$_2$($\beta$) | 4-OMe—PhEt($\beta$) |
| 130 | 7-OH | H | NMe$_2$($\beta$) | 4-OMe—PhEt($\beta$) |
| 131 | 6-OH | H | NHCOCH$_2$NEt$_2$($\beta$) | Et($\beta$) |
| 132 | 7-OH | H | NHCOCH$_2$NEt$_2$($\beta$) | Et($\beta$) |
| 133 | 6-OH | H | CONHNMe$_2$($\beta$) | Et($\beta$) |
| 134 | 7-OH | H | CONHNMe$_2$($\beta$) | Et($\beta$) |
| 135 | 6-OH | H | CONHNMe$_2$($\beta$) | 4-OMe—PhEt($\beta$) |
| 136 | 6-OH | H | CONHNMe$_2$($\beta$) | 3,4-diOMePhEt($\beta$) |

-continued

| Cpd No | X¹ | X² | R² | R⁴ |
|---|---|---|---|---|
| 137 | 6-OH | H | CONHNH₂(β) | Et(β) |
| 138 | 7-OH | H | CONHNH₂(β) | Et(β) |
| 139 | 6-OH | H | CONHNH₂(β) | 3,4-diOMe—PhEt(β) |
| 140 | 6-OH | H | COO(4-MePip—Et)(β) | Et(β) |
| 141 | 6-OH | H | OH—Et—NHNHCO—(β) | Et(β) |
| 142 | 7-OH | H | OH—Et—NHNHCO—(β) | Et(β) |
| 143 | 6-OH | H | OH—Et—NHNHCO—(β) | 3,4-diOMe—PhEt(β) |
| 144 | 6-OH | H | CONHNHPh(β) | Et(β) |
| 145 | 6-OH | H | CONHNH(Prl—Et)(β) | Me(β) |
| 146 | 7-OH | H | CONHNH(Prl—Et)(β) | Et(β) |
| 147 | 6-OH | H | CONHNH(Prl—Et)(β) | 3,4-diOMe—PhEt(β) |
| 148 | 6-OH | H | CONHNH(Pid—Et)(β) | Me(β) |
| 149 | 6-OH | H | CONHNH(Pid—Et)(β) | 4-OMe—PhEt(β) |
| 150 | 6-OH | H | CONHNH(Pid—Et)(β) | 3,4-diOMe—PhEt(β) |
| 151 | 6-OH | H | CONHNH(4-MePip—Et)(β) | Et(β) |
| 152 | 6-OH | H | CONHNH(4-MePip—Et)(β) | 3,4-diOMe—PhEt(β) |
| 153 | 6-OH | H | CONHNHMe(β) | Et(β) |
| 154 | 6-OH | H | CONHNHMe(β) | 3,4-diOMe—PhEt(β) |
| 196 | 7-OH | H | NH₂(β) | Me(β) |
| 197 | 7-OH | H | NH₂(β) | Et(β) |
| 198 | 7-OH | H | NH₂(β) | Pr(β) |
| 199 | 7-OH | H | NH₂(β) | iPr(β) |
| 204 | 6-OH | H | NH₂(β) | Et(β) |
| 205 | 6-OH | H | NH₂(β) | Et(β) |
| 207 | 7-OH | 8-OH | NH₂(α) | Et(β) | wherein:
All=allyl;
Brn=2-bornyl;
Bu=butyl;
Bz=benzyl;
Cin=cinnamoyl;
Et=ethyl;
iPr=isopropyl;
Me=methyl;
Mor=morpholino;
mTo=m-tolyl;
Ph=phenyl;
Pid=piperidino;
Pip=1-piperazinyl;
Pr=propyl;
Prl=1-pyrrolidinyl.

13. A method of treating arrhythmia in a mammal by administering to said mammal an anti-arrhythmic effective amount of a compound selected from the group consisting of compounds of formula (I):

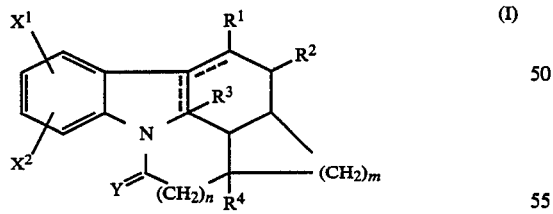

in which:
the dotted lines represent one single carbon-carbon bond and one double carbon-carbon bond or two single carbon-carbon bonds;
m is an integer from 2 to 7;
n is an integer from 1 to 3;
Y represents 2 hydrogen atoms or an oxo group;
$R^1$ represents a hydrogen atom or a $C_1$-$C_6$ alkyl group;
$R^2$ represents a hydrogen atom, a carboxy group, a group of formula —NHCOOR$^b$ in which R$^b$ represents a $C_1$-$C_6$ alkyl group, a substituted $C_1$-$C_6$ alkyl group, an aralkyl group wherein the aryl part is $C_6$-$C_{10}$ carbocyclic aryl and the alkyl part is $C_1$-$C_6$ alkyl, a substituted aralkyl group wherein the aryl part is $C_6$-$C_{10}$ carbocyclic aryl and the alkyl part is $C_1$-$C_6$ alkyl, a $C_3$-$C_6$ alkenyl group, a $C_3$-$C_6$ haloalkenyl group, a $C_3$-$C_{10}$ cycloalkyl group or a substituted $C_3$-$C_{10}$ cycloalkyl group, a group of formula —NR₂, a quaternary ammonium group of formula —N⁺(R')₃, a group of formula —CONR₂, a group of formula —NHNR₂, a group of formula —NHCONR₂, an aminoalkanoylamino group wherein the alkanoyl part is $C_2$-$C_7$ alkanoyl, a group of formula —CO.NH.NR₂ or a group of formula —CO.NH.N=CHR'';
$R^4$ represents a hydrogen atom, a $C_1$-$C_6$ alkyl group, a $C_3$-$C_6$ alkenyl group, a $C_3$-$C_6$ alkynyl group, an aralkyl group wherein the aryl part is a $C_6$-$C_{10}$ carbocyclic aryl group and the alkyl part is $C_1$-$C_6$ alkyl, or the phenyl group;
$X^1$ and $X^2$ are independently selected from the group consisting of hydrogen atoms, $C_1$-$C_6$ alkyl groups, substituted $C_1$-$C_6$ alkyl groups, $C_1$-$C_6$ alkoxy groups, aralkyloxy groups wherein the aryl part is a $C_6$-$C_{10}$ carbocyclic aryl group and the alkyl part is a $C_1$-$C_6$ alkyl group, hydroxy groups, halogen atoms, trifluoromethyl groups, nitro groups, amino groups, aminoalkanoylamino groups wherein the alkanoyl part is $C_2$-$C_7$ alkanoyl, mono- and di-alkylaminoalkanoylamino groups wherein the alkanoyl part is $C_2$-$C_7$ alkanoyl and the or each alkyl part is $C_1$-$C_6$ alkyl and is substituted or unsubstituted, $C_2$-$C_7$ alkanoyloxy groups, carboxy groups, carbamoyl groups, mono- and di-alkylcarbamoyl groups where the or each alkyl part is $C_1$-$C_6$ alkyl and cyano groups;
the substituents on said alkyl, cycloalkyl, alkoxy, aralkyl and heterocyclic groups are from 1 to 2 substituents selected from the group consisting of halogen atoms, cyano groups, nitro groups, hydroxy groups, $C_1$-$C_4$ alkoxy groups, mercapto groups, $C_1$-$C_4$ alkylthio groups, $C_1$-$C_6$ alkanoyl groups, carboxy groups, alkoxycarbonyl groups where the alkoxy part is C₁–C₄ alkoxy, amino groups, C₁–C₄ alkylamino groups, dialkylamino groups where each alkyl part is C₁–C₄ alkyl, carbamoyl groups, alkylcarbamoyl groups where the alkyl part is C₁–C₄ alkyl, dialkylcarbamoyl groups where each alkyl part is C₁–C₄ alkyl, and, only as substituents on substituted alkyl and alkoxy groups, C₃–C₁₀ cycloalkyl groups, substituted C₃–C₁₀ cycloalkyl groups, heterocyclic groups and substituted heterocyclic groups, and, only as substituents on cycloalkyl groups and substituted aryl parts of aralkyl groups, C₁–C₄ alkyl groups and substituted C₁–C₄ alkyl groups, and, only as substituents on substituted heterocyclic groups, C₁–C₄ alkyl groups, substituted C₁–C₄ alkyl groups, C₆–C₁₀ carbocyclic aryl groups, substituted C₆–C₁₀ carbocyclic aryl groups, arylalkenoyl groups wherein the aryl part is C₆–C₁₀ carbocyclic aryl and the alkenoyl part is C₃–C₆ alkenoyl and substituted arylalkenoyl wherein the aryl part is substituted C₆–C₆ carbocyclic aryl and the alkenoyl part is C₃–C₆ alkenoyl;

said heterocyclic groups being selected from the group consisting of pyrrolidinyl, morpholinyl, piperidinoyl and piperazinyl;

said nitrogenous heterocyclic group being seledcted from the group consisting of: N-(2-cyclohexylethyl)carbamoyl, N-[2-(1-pyrrolidinyl)ethyl]carbamoyl, N-(2-piperidinoethyl)carbamoyl, N-(2-morpholinoethyl)carbamoyl, N-(3-morpholinopropyl)carbamoyl, N-(4-morpholinobutyl)carbamoyl, N-[2-(4-methyl-1-piperazinyl)ethyl]carbamoyl, N-[2-(4-phenyl-1-piperazinyl)ethyl]carbamoyl, N-[2-(4-ethoxycarbonyl-1-piperazinyl)ethyl]carbamoyl, N-benzylcarbamoyl, N-4-methylbenzylcarbamoyl, N-2-chlorobenzylcarbamoyl, N-4-chlorobenzylcarbamoyl, N-2-methoxybenzylcarbamoyl, N-4-methoxybenzylcarbamoyl, N-3,4-dimethoxybenzylcarbamoyl, N-phenethylcarbamoyl, N-4-methylphenethylcarbamoyl, N-4-chlorophenethylcarbamoyl, N-4-methoxyphenethylcarbamoyl, N-3,4-dimethoxyphenethylcarbamoyl, N-3,4,5-trimethoxyphenethylcarbamoyl, N-3-phenylpropylcarbamoyl, N-4-phenylbutylcarbamoyl, N-furfurylcarbamoyl, N-(2-pyridylmethyl)carbamoyl, N-(4-pyridylmethyl)carbamoyl, N-2-pyrid-2-ylethyl)carbamoyl, N-cyclopentylcarbamoyl, N-cyclohexylcarbamoyl, N-phenylcarbamoyl, N-4-tolylcarbamoyl, N-4-chlorophenylcarbamoyl, N-4-methoxyphenylcarbamoyl, N-2-pyridylcarbamoyl, N-2-furylcarbamoyl, N-morpholinocarbamoyl, N-piperidinocarbamoyl and N-piperazinylcarbamoyl groups; and heterocylcic-carbonyl groups, selected from the group consisting of 1-pyrrolidinylcarbonyl, piperidinocarbonyl, 4-methyl-1-piperazinylcarbonyl and 4-phenyl-1-piperazinylcarbonyl groups, or a pharmaceutically acceptable salt or ester thereof.

14. A method as claimed in claim 13, wherein said anti-arrhythmic compound has the formula (IV):

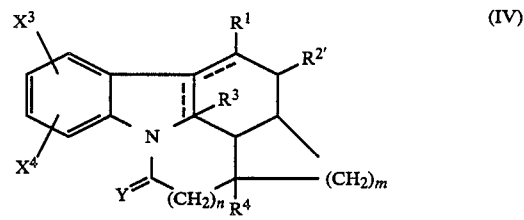

(IV)

wherein R¹, R³, R⁴, Y, n, m and the dotted lines are as in claim 7;

R²' represents any one of the groups or atoms defined for R² or a group of formula COORᵃ wherein Rᵃ represents a C₁–C₆ alkyl group, a substituted C₁–C₆ alkyl group, an aralkyl group wherein the aryl part is C₆–C₁₀ carbocyclic aryl and is substituted or unsubstituted and the alkyl part is C₁–C₆ alkyl, a C₃–C₆ alkenyl group, a C₃–C₆ haloalkenyl group, a C₃–C₁₀ cycloalkyl group or a C₃–C₁₀ cycloalkyl group having from 1 to 5 C₁–C₄ alkyl substituents; and X³ and X⁴ are independently selected from the group consisting of the groups and atoms defined for X¹ and X² and groups of formula COORᵃ in which Rᵃ is as defined above, or is a salt thereof.

15. A method as claimed in claim 14, in which:

m is 2 or 3;

n is 1;

Y represents an oxo group;

R¹ represents a hydrogen atom;

R²' represents a group of formula COORᵃ, in which Rᵃ represents an aminoalkyl group, or R²' represents a group of formula —NR₂, in which the two groups represented by R are independently selected from the group consisting of hydrogen atoms and C₁–C₄ alkyl groups, an aminoalkanoylamino group, in which the alkanoyl part is a C₂–C₇ alkanoyl group, a group of formula —CO.NH.NR₂, in which the two groups represented by R are independently selected from the group consisting of C₁–C₆ alkyl groups, or the two groups represented by R together with the nitrogen atom to which they are attached represent a nitrogenous heterocyclic group, or a group of formula —CO.NHNHR, in which R represents a C₁–C₆ aminoalkyl group, a phenyl group, an aralkyl group in which the aryl part is C₆–C₁₀ carbocyclic aryl and the alkyl part is C₁–C₄ alkyl, a heterocyclic group, a hydrogen atom, a C₁–C₄ alkyl group or a C₁–C₄ hydroxyalkyl group;

R³ repesents a hydrogen atom;

R⁴ represents a hydrogen atom, a C₁–C₄ alkyl group or an aralkyl group in which the aryl part is C₆–C₁₀ carbocyclic aryl and the alkyl part is C₁–C₄ alkyl; and X³ and X⁴ are independently selected from the group consisting of hydrogen atoms and hydroxy groups.

16. A method as claimed in claim 13, wherein said anti-arrhythmic compound has the formula (V):

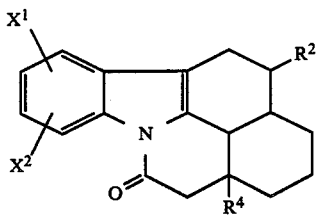

(in which:

R[2] represents a 2-(1-piperazinyl)ethoxycarbonyl group, a 2-(1-piperazinyl)ethoxycarbonyl group having an alkyl, phenyl, substituted phenyl or alkoxycarbonyl substituent at the 4-position of the piperazinyl group, an amino group, a dimethylamino group, an aminoacetamido group, an aminoacetamido group having one or two $C_1$–$C_4$ alkyl substituents on the amino group, a carbamoyl group having a single dimethylamino, morpholino, piperidino, 1-pyrrolidinyl or 4-methyl-1-piperazinyl substituent, a carbazoyl group or a carbazoyl group having on the 3-nitrogen atom a substituent selected from the group consisting of methyl, 2-hydroxyethyl, phenyl, benzyl, pyridyl, 2-(1-pyrrolidinyl)ethyl, 2-piperidinoethyl, 2-morpholinoethyl and 2-(4-methyl-1-piperazinyl)ethyl substituents;

R[4] represents a hydrogen atom or a methyl, ethyl, propyl, isopropyl, butyl, 4-methoxyphenethyl, 3,4-dimethoxyphenethyl or 3,4,5-trimethoxyphenethyl group; and X[1] and X[2] are independently selected from the group consisting of hydrogen atoms and hydroxy groups at the 6-, 7- and 8-positions.

17. A method as claimed in claim 16, wherein either both X[1] and X[2] represent hydrogen atoms, or X[2] represents a hydrogen atom and X[1] represents a 6-hydroxy or 7-hydroxy group or X[1] represents a 7-hydroxy group and X[2] represents an 8-hydroxy group.

18. A method as claimed in claim 1, wherein said compound has the formula (I-5):

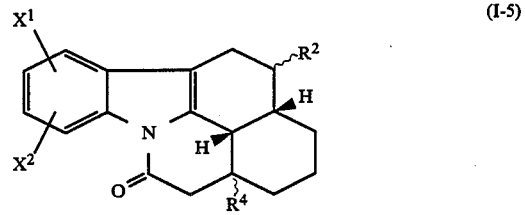

wherein X[1], X[2], R[2] and R[4] are as defined below:

| Cpd No | X[1] | X[2] | R[2] | R[4] |
|---|---|---|---|---|
| 107 | 7-OH | H | NH$_2$($\beta$) | H($\beta$) |
| 111 | 6-OH | H | NH$_2$($\beta$) | H($\beta$) |
| 112 | 6-OH | H | NH$_2$($\beta$) | Me($\beta$) |
| 113 | 7-OH | 8-OH | NH$_2$($\beta$) | Me($\beta$) |
| 114 | 7-OH | H | NH$_2$($\alpha$) | Et($\beta$) |
| 115 | 6-OH | H | NH$_2$($\beta$) | Pr($\beta$) |
| 116 | 7-OH | 8-OH | NH$_2$($\beta$) | Pr($\beta$) |
| 117 | 6-OH | H | NH$_2$($\beta$) | iPr($\beta$) |
| 118 | 6-OH | H | NH$_2$($\beta$) | 4-OMe—PhEt($\beta$) |
| 119 | 7-OH | H | NH$_2$($\beta$) | 4-OMe—PhEt($\beta$) |
| 120 | 6-OH | H | NH$_2$($\beta$) | 3,4-diOMe—PhEt($\beta$) |
| 121 | 7-OH | H | NH$_2$($\beta$) | 3,4-diOMe—PhEt($\beta$) |
| 122 | 6-OH | H | NH$_2$($\beta$) | 3,4,5-triOMe—PhEt($\beta$) |
| 123 | 6-OH | H | NMe$_2$($\beta$) | Me($\beta$) |
| 124 | 7-OH | H | NMe$_2$($\beta$) | Me($\beta$) |
| 125 | 6-OH | H | NMe$_2$($\beta$) | Et($\beta$) |
| 126 | 7-OH | H | NMe$_2$($\beta$) | Et($\beta$) |
| 127 | 6-OH | H | NMe$_2$($\beta$) | 3,4-diOMe—PhEt($\beta$) |
| 128 | 7-OH | H | NMe$_2$($\beta$) | 3,4-diOMe—PhEt($\beta$) |
| 129 | 6-OH | H | NMe$_2$($\beta$) | 4-OMe—PhEt($\beta$) |
| 130 | 7-OH | H | NMe$_2$($\beta$) | 4-OMe—PhEt($\beta$) |
| 131 | 6-OH | H | NHCOCH$_2$NEt$_2$($\beta$) | Et($\beta$) |
| 132 | 7-OH | H | NHCOCH$_2$NEt$_2$($\beta$) | Et($\beta$) |
| 133 | 6-OH | H | CONHNMe$_2$($\beta$) | Et($\beta$) |
| 134 | 7-OH | H | CONHNMe$_2$($\beta$) | Et($\beta$) |
| 135 | 6-OH | H | CONHNMe$_2$($\beta$) | 4-OMe—PhEt($\beta$) |
| 136 | 6-OH | H | CONHNMe$_2$($\beta$) | 3,4-diOMePhEt($\beta$) |
| 137 | 6-OH | H | CONHNH$_2$($\beta$) | Et($\beta$) |
| 138 | 7-OH | H | CONHNH$_2$($\beta$) | Et($\beta$) |
| 139 | 6-OH | H | CONHNH$_2$($\beta$) | 3,4-diOMe—PhEt($\beta$) |
| 140 | 6-OH | H | COO(4-MePip—Et)($\beta$) | Et($\beta$) |
| 141 | 6-OH | H | OH—Et—NHNHCO—($\beta$) | Et($\beta$) |
| 142 | 7-OH | H | OH—Et—NHNHCO—($\beta$) | Et($\beta$) |
| 143 | 6-OH | H | OH—Et—NHNHCO—($\beta$) | 3,4-diOMe—PhEt($\beta$) |
| 144 | 6-OH | H | CONHNHPh($\beta$) | Et($\beta$) |
| 145 | 6-OH | H | CONHNH(Prl—Et)($\beta$) | Me($\beta$) |
| 146 | 7-OH | H | CONHNH(Prl—Et)($\beta$) | Et($\beta$) |
| 147 | 6-OH | H | CONHNH(Prl—Et)($\beta$) | 3 4-diOMe—PhEt($\beta$) |
| 148 | 6-OH | H | CONHNH(Pid—Et)($\beta$) | Me($\beta$) |
| 149 | 6-OH | H | CONHNH(Pid—Et)($\beta$) | 4-OMe—PhEt($\beta$) |
| 150 | 6-OH | H | CONHNH(Pid—Et)($\beta$) | 3,4-diOMe—PhEt($\beta$) |
| 151 | 6-OH | H | CONHNH(4-MePip—Et)($\beta$) | Et($\beta$) |
| 152 | 6-OH | H | CONHNH(4-MePip—Et)($\beta$) | 3,4-diOMe—PhEt($\beta$) |
| 153 | 6-OH | H | CONHNHMe($\beta$) | Et($\beta$) |

-continued

| Cpd No | X¹ | X² | R² | R⁴ |
|---|---|---|---|---|
| 154 | 6-OH | H | CONHNHMe(β) | 3,4-diOMe—PhEt(β) |
| 196 | 7-OH | H | NH₂(β) | Me(β) |
| 197 | 7-OH | H | NH₂(β) | Et(β) |
| 198 | 7-OH | H | NH₂(β) | Pr(β) |
| 199 | 7-OH | H | NH₂(β) | iPr(β) |
| 204 | 6-OH | H | NH₂(β) | Et(β) |
| 205 | 6-OH | H | NH₂(α) | Et(β) |
| 207 | 7-OH | 8-OH | NH₂(β) | Et(β) | wherein:
All=allyl;
Brn=2-bornyl;
Bu=butyl;
Bz=benzyl;
Cin=cinnamoyl;
Et=ethyl;
iPr=isopropyl;
Me=methyl;
Mor=morpholino;
mTo=m-tolyl;
Ph=phenyl;
Pid=piperidino;
Pip=1-piperazinyl;
Pr=propyl;
Prl=1-pyrrolidinyl.

19. A compound of formula (I-5):

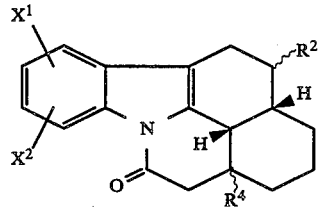

(I-5)

wherein

X¹ is 6—OH or 7—OH;
X² is H;
R² is NH₂ and
R⁴ is H or C₁-C₆ alkyl.

20. The compound of claim 19 wherein X¹ is 7—OH, R² is NH₂ (β) and R⁴ is H(β).

21. The compound of claim 19 wherein X¹ is 6—OH; R² is NH₂(β) and R⁴ is H(β).

22. The compound of claim 19 wherein C¹ is 6—OH, R² is NH₂(β) and R⁴ is Me(β).

23. The compound of claim 19 wherein X¹ is 7—OH, R² is NH₂(β) and R⁴ is Et(β).

24. The compound of claim 19 wherein X¹ is 6—OH, R² is NH₂(β) and R⁴ is Pr(β).

25. The compound of claim 19 wherein X¹ is 6—OH, R² is NH₂(β) and R⁴ is iPr(β).

26. The compound of claim 19 wherein X¹ is 7—OH, R² is NH₂(β) and R⁴ is Me(β).

27. The compound of claim 19 wherein X¹ is 7—OH, R² is NH₂(β) and R⁴ is Et(β).

28. The compound of claim 19 wherein X¹ is 7—OH, R² is NH₂(β) and R⁴ is Pr(β).

29. The compound of claim 19 wherein X¹ is 7—OH, R² is NH₂(β) and R⁴ is iPr(β).

30. The compound of claim 19 wherein X¹ is 6—OH, R² is NH₂(β) and R⁴ is Et(β).

* * * * *

UNITED STATES PATENT AND TRADEMARK OFFICE
CERTIFICATE OF CORRECTION

PATENT NO. : 4,716,162

DATED : December 29, 1987

INVENTOR(S) : TOMITA et al

It is certified that error appears in the above-identified patent and that said Letters Patent is hereby corrected as shown below:

Column 9, line 56, " R' " should read -- R" --.

Column 40, line 67, " 1$\overline{\text{H}}$ " should read -- 1$\underline{\text{H}}$ --.

Column 41, line 45, " 619 g " should read -- 619 mg --.

Column 69, line 49 (claim 7), " $C_1-C_{10}$ " should read -- $C_3-C_{10}$ --.

Column 73, next to last line of the table,

"205 6-OH  H  $NH_2(\beta)$ "should read --205 6-OH  H  $NH_2$(a)--.

Column 73, last line of the table,

"207 7-OH  8-OH  $NH_2$(a)" should read --207 7-OH  8-OH  $NH_2(\beta)$--.

Colum 74, line 40 (claim 13), after "=CHR";", insert the following:

--the two atoms or groups represented by R are independently selected from the group consisting of hydrogen atoms, $C_1-C_6$ alkyl groups, substituted $C_1-C_6$ alkyl groups, aralkyl groups where the aryl part is $C_6-C_{10}$ carbocyclic aryl and the alkyl part is $C_1-C_6$ alkyl, substituted aralkyl groups where the aryl

UNITED STATES PATENT AND TRADEMARK OFFICE
CERTIFICATE OF CORRECTION

PATENT NO. : 4,716,162                                    Page 2 of 3

DATED : December 29, 1987

INVENTOR(S) : TOMITA et al

It is certified that error appears in the above-identified patent and that said Letters Patent is hereby corrected as shown below:

part is $C_6$-$C_{10}$ carbocyclic aryl and the alkyl part is $C_1$-$C_6$ alkyl, heterocyclic groups and substituted heterocyclic groups;

or the two symbols R, together with the nitrogen atom to which they are attached, represent a nitrogenous heterocyclic group;

the three groups represented by R' are independently selected from the group consisting of $C_1$-$C_6$ alkyl groups, substituted $C_1$-$C_6$ alkyl groups, aralkyl groups where the aryl part is $C_6$-$C_{10}$ carbocyclic aryl and the alkyl part is $C_1$-$C_6$ alkyl and substituted aralkyl groups where the aryl part is $C_6$-$C_{10}$ carbocyclic aryl and the alkyl part is $C_1$-$C_6$ alkyl;

R" represents a $C_1$-$C_5$ alkyl group or a phenyl group;

UNITED STATES PATENT AND TRADEMARK OFFICE
CERTIFICATE OF CORRECTION

PATENT NO.   : 4,716,162  
DATED        : December 29, 1987  
INVENTOR(S)  : TOMITA et al It is certified that error appears in the above-identified patent and that said Letters Patent is hereby corrected as shown below:

$R^3$ represents a hydrogen atom, a $C_1$-$C_3$ alkyl group or a substituted $C_1$-$C_3$ alkyl group; --.

Signed and Sealed this

Third Day of November, 1992

Attest:

DOUGLAS B. COMER

*Attesting Officer*      *Acting Commissioner of Patents and Trademarks*